(12) United States Patent
Brady et al.

(10) Patent No.: US 10,472,656 B2
(45) Date of Patent: Nov. 12, 2019

(54) METHOD FOR FERMENTING SUGARS USING GENETICALLY ENGINEERED YEAST

(71) Applicant: CARGILL, INCORPORATED, Wayzata, MN (US)

(72) Inventors: Keith M. Brady, Eden Prairie, MN (US); Christopher K. Miller, Andover, MN (US)

(73) Assignee: CARGILL, INCORPORATED, Wayzata, MA (US)

(*) Notice: Subject to any disclaimer, the term of this patent is extended or adjusted under 35 U.S.C. 154(b) by 0 days.

(21) Appl. No.: 15/318,907

(22) PCT Filed: Jun. 18, 2015

(86) PCT No.: PCT/US2015/036460
§ 371 (c)(1),
(2) Date: Dec. 14, 2016

(87) PCT Pub. No.: WO2015/195934
PCT Pub. Date: Dec. 23, 2015

(65) Prior Publication Data
US 2017/0130251 A1    May 11, 2017

Related U.S. Application Data

(60) Provisional application No. 62/013,996, filed on Jun. 18, 2014.

(51) Int. Cl.
| | | |
|---|---|---|
| C12P 19/02 | (2006.01) | |
| C12P 7/02 | (2006.01) | |
| C12P 7/10 | (2006.01) | |
| C12P 7/56 | (2006.01) | |
| C12P 7/64 | (2006.01) | |
| C12P 13/04 | (2006.01) | |
| C12N 15/81 | (2006.01) | |
| C12P 7/40 | (2006.01) | |

(52) U.S. Cl.
CPC ............ *C12P 19/02* (2013.01); *C12N 15/815* (2013.01); *C12P 7/02* (2013.01); *C12P 7/40* (2013.01); *C12P 7/56* (2013.01); *C12P 7/6409* (2013.01); *C12P 7/6436* (2013.01); *C12P 13/04* (2013.01)

(58) Field of Classification Search
None
See application file for complete search history.

(56) References Cited

U.S. PATENT DOCUMENTS

2011/0003347 A1* 1/2011 Takeshita ............ C12N 9/1205
435/106

FOREIGN PATENT DOCUMENTS

| EP | 2241632 A1 | 10/2010 |
|---|---|---|
| WO | 2008/155665 A2 | 12/2008 |
| WO | WO 2009/088049 A1 * | 7/2009 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Porro et al. (Development of Metabolically Engineered *Saccharomyces cerevisiae* Cells for the Production of Lactic Acid., Biotechnol. Prog. 1995, 11, 294-298).*
Osorio-Cadavid et al. (Detection and identification of wild yeasts in Champu's, a fermented Colombian maize beverage. Food Microbiology 25 (2008) 771-777).*
Beschkov et al. (A kinetic model for the hydrolysis and synthesis of maltose, isomaltose and maltotriose., Biotechnol and Bioengineering (1984), vol. XXVI, p. 22-26).*
International Search Report from International Application No. PCT/US2015/036460, dated Dec. 12, 2015 (8 pages).
Written Opinion from International Application No. PCT/US2015/036460, dated Dec. 12, 2015 (10 pages).
Boles et al., "The molecular genetics of hexose transport in yeasts", FEMS Microbiology Reviews, vol. 21, No. 1, 1997, pp. 85-111.
Smit et al., "The Thr 505 and Ser 557 residues of the AGT1-encoded [alpha]-glucoside transporter are critical for maltotriose transport in *Saccharomyces cerevisiae*", Journal of Applied Microbiology, vol. 104, No. 4, Apr. 1, 2008, pp. 1103-1111.

(Continued)

*Primary Examiner* — Iqbal H Chowdhury

(57) ABSTRACT

A fermentation process for fermenting a starch hydrolysate containing 60-98 weight percent of glucose based on total carbohydrate and 0.3-5% weight percent of isomaltose based on total carbohydrate to a non-ethanol fermentation product is carried out. The method comprises: a) forming a fermentation broth containing the starch hydrolysate and a genetically modified microorganism containing i) an exogenous gene encoding transporter capable of transporting isomaltose ii) an exogenous gene encoding an enzyme capable of converting isomaltose to glucose; and b) fermenting the starch hydrolysate in the fermentation broth to produce a non-ethanol fermentation product. This fermentation process may be carried out as a single step fermentation or a batch process. The genetically modified microorganism may contain an exogenous gene encoding an enzyme that catalyzes the formation of a product other than ethanol.

18 Claims, 1 Drawing Sheet
Specification includes a Sequence Listing.

(56) References Cited

OTHER PUBLICATIONS

Teste et al., "Characterization of a new multigene family encoding ismatases in the yeast *Saccharomyces cerevisiae*, the IMA family", Journal of Biological Chemistry, vol. 285, No. 35, Aug. 27, 2010, pp. 26815-26824.

Badotti et al., "Switching the mode of sucrose utilization by *Saccharomyces cerevisiae*", Microbial Cell Factories, vol. 7, No. 1, Feb. 27, 2008, p. 4.

Han et al., "Characterization of AGT1 encoding a general alpha-glucoside transporter from *Saccharomyces*", Molecular Microbiology, vol. 17, No. 6, Jan. 1, 1995, pp. 1093-1107.

* cited by examiner

SEQUENCE LISTING

```
<160> NUMBER OF SEQ ID NOS: 25

<210> SEQ ID NO 1
<211> LENGTH: 993
<212> TYPE: DNA
<213> ORGANISM: Artificial Sequence
<220> FEATURE:
<223> OTHER INFORMATION: Cyb2a 5' Flank

<400> SEQUENCE: 1
aacagtatcg atgaaaggtg tacgactttta taagagggct tttctcgtag ctctttcaaa      60
tagtatctca ttgtatacta agatagtttg tatttgtgtg tgtgtgtcag tgtaagtgtt     120
agtatacttg ttttcctctt tccctagag ttggtggtgt gttttgttgg aacgtacatt     180
agatgcataa tgcgtgacac cgccatgatg gttgtattct accaatgaga catggccgtt     240
gatcctgctg tgtgggtcat gagacatcac ctcttggggg ggattctcct ataattggca     300
ccgtgtatgc ctcaaccact aacttccacc ctataactga atatattaca taagcaaatc     360
tactttttgt ttgtgttgat cgccatcgtt gaaattcgcg caacttctgg tggctcaacg     420
ctgctgttct atcggtatcc taagagatgt ctttgccctg agtctagggt aaactatcca     480
ccttcgttgc tgtttgacta gacagctact aactttaggg tagtaaatga ataacggctc     540
gctctcatga tcacttctct acatcaccct aacaagtgta ttatttttt ttcaagtggg      600 tgttgctgtt ggtgctagcc ttagtgccct cgttaatagt tgaacaaaca ctggcatttg     660
gagtataatg aaaagggatc actaccccc gcttcctgtt ccgcttctcc cttccggaaa      720
aaccacccac cctttctttt cccccactaa tgtatgaatt tttccgttcc caggggaatg     780
gcccacttgg ttctctgtta acccacacaa ttttgacgca tcccacacac ctttttttt     840 tctaccccac actttcccctt gaaaaatctc caatttgaac tggcaattt cacccccccac   900 cacttgcatt cattagtgag tcaatccatc ccgcggtcgg agattcggaa tccacctact    960
ggtaatctgt aatctatatt cccgctgacc ctt                                 993

<210> SEQ ID NO 2
<211> LENGTH: 690
<212> TYPE: DNA
<213> ORGANISM: Artificial Sequence
<220> FEATURE:
<223> OTHER INFORMATION: Cyb2a 3' Flank

<400> SEQUENCE: 2
tagatactgc tcctcctcca atcgaattat tagctgaaac tgttccaact ttgaagagat      60
```

```
tgggtaaatt aagaccagat tttgaaattt taattgacgg tggtgtcaaa agaggtaccg      120
atattttgaa agcagtcgca atcggtggcc aagatgtcag agtttcagtt ggtatgggta      180
gacctttctt atatgccaac tcttgctatg gtgaagcagg tgttagaaaa ttaattcaaa      240
atctaaagga tgaattagaa atggatatga gattgttggg tgtcactaaa atggaccagc      300
tatcttcgaa acatgtcgat actaaacgtt tgattggtag agatgcgatc aactatttgt      360
atgataatgt atacagccca atcgaaaccg ttaaattcaa caatgaagat tgattgttgg      420
aaatatatta ttcataaagg cgaaaacatt cccttggtat tttattccaa atttatgata      480
catagacgta ttttttatat ataaagttat attattaatg attcaagaaa aagttcaaat      540
aaactaatgg atcaacctat ttcgacccct tcttcattgc tacttcttcc ttaagcaaca      600
gatgattaag tagatactgt ttttttagcc aatagtatct cgccgaggag ttatacttga      660
ctagctcttg ctcaagaatc ttcctaagac                                      690

<210> SEQ ID NO 3
<211> LENGTH: 572
<212> TYPE: DNA
<213> ORGANISM: Artificial Sequence
<220> FEATURE:
<223> OTHER INFORMATION: Cyb2b 5' Flank

<400> SEQUENCE: 3
agatgtatcc gtttggaatc tcatgacttt tggtgtgtgg tctgtgtctt cccagttatc       60
tacttgagtg attatgatcc agttttcacc attggttaca taccaaacag agaacttata      120
cgcaccagaa cgccttttgt gtcttttgt ttctcaagta tttctatcag tttccttcat      180
gtatcccggg actccattgt cctcggtagt gcctaccaat ttaatgtttg actccttgcg      240
ttttctcctg tcgcggacaa acggtgcggc tcccccgatg attcacgtaa taagccggag      300
tcaaccacag aggtcccta tgactcaaca aggcctcgta gaaactcggc ttctcggaga      360
aagagtcttt tctttttcac tggaaaatat ttttttttcc tttatattct tttgaaccaa      420
aatgtggcta ctataaaagt gccttttatt cccagctttt ctagcatgat tgagtcacct      480
tccacaatga gtcttcttta ttgttagtat tgtgaatatt atccgtgcag ttttcaagaa      540
cgtaaatcaa cagcagtgat aataccttca aa                                   572

<210> SEQ ID NO 4
<211> LENGTH: 499
<212> TYPE: DNA
<213> ORGANISM: Artificial Sequence
<220> FEATURE:
<223> OTHER INFORMATION: Cyb2b 3' Flank

<400> SEQUENCE: 4
tctgatattt gctaaattga atgaacctt accatgccac atctatagac atcaaaacca        60
ttttcaattt gtcgatatct tttgcatatc aaagtaatac caagcatgtt caaaagaaa      120 agaaagcata actttaatac tctattcgaa acattccgat ccacaacaca ttagtctttt      180
taggcccgtt gttcatcttt ctattacttt attcctaact gtatttttat aattccgggt      240
ttataaaaga ttaaactaat atagcgcatt ctttttgggg acaaacatac ataacgagc       300 tcattcatac atcgcttttc agttcgactg gtgtttcgga tgcctctttt tctaaggagc      360
tagattctgg ccccacacta gtctttgaac tcgttgctcc ttaccaccc ttaccaccag       420 ccttacttgt aggttttca gtagcatact ctgcgtgttt gactaaattc ccttccttaa       480
```
ctttgtgcca gcttggcca                                                   499

<210> SEQ ID NO 5
<211> LENGTH: 6517
<212> TYPE: DNA
<213> ORGANISM: Artificial Sequence
<220> FEATURE:
<223> OTHER INFORMATION: pVL3 integration fragment

<400> SEQUENCE: 5

```
cccgccatga tggttgtatt ctaccaatga gacatggccg ctgatcctgt tgtgtgggtc     60
atgggacatc acctcttggg gaggattctc ctataattgg caccgtgtat gcctcaacca    120
ctaacttcca ccctataact gaatatatta cataagcaaa tctactttt gtttgtgttg    180
atcgccatcg ttgaaattcg cgcaacttct ggtggctcaa cgctgctgtt ctatcggtat    240
cctaagagat gtctttgccc tgagtctagg gtaaactatc caccttcgtt gctgtttgac    300
tagacagcta ctaactttac ggtagtaaat gaataacggc tcgctctcat gatcacttct    360
ctacatcacc ctaacaagtg tattattttt tttcaggtgg gtgttgctgt tggtgctagc    420
cttagtgccc tcgttaatag ttgaacaaac actggcattt ggagtataat gaaaagggat    480
cactacccc cgcttcctgt tccgcttctc ccttccggaa aaaccaccca cccttctctt    540
tccccccacta atgtatgaat ttttccgttc caggggaat ggcccacttg gttctctgtt    600
aacccacaca attttgacgc atcccacaca ccttttttt tttctacccc cacttttccc    660
ttgaaaaatc tccaatttga actggcaatt tcacccccc accacttgca ttcattagtg    720
agtcaatcca tcccgcggtc ggagattcgg aatccaccta ctggtaatct gtaatctata    780
ttcccgctga cccttgtcga cttgctgcaa cggcaacatc aatgtccacg tttacacacc    840
tacatttata tctatattta tatttatatt tatttattta tgctacttag cttctatagt    900
tagttaatgc actcacgata ttcaaaattg acaccttca actactccct actattgtct    960
actactgtct actactcctc tttactatag ctgctcccaa taggctccac caataggctc   1020
tgtcaataca ttttgcgccg ccacctttca ggttgtgtca ctcctgaagg accatattgg   1080
gtaatcgtgc aatttctgga agagagtccg cgagaagtga ggcccccact gtaaatcctc   1140
gagggggcat ggagtatggg gcatggagga tggaggatgg ggggggggag aaaataggta   1200
gcgaaaggac ccgctatcac cccacccgga gaactcgttg ccgggaagtc atatttcgac   1260
actccgggga gtctataaaa ggcgggtttc gtcttttgcc agttgatgtt gctgagagga   1320
cttgtttgcc gtttcttccg atttaacagt atagaatcaa ccactgttaa ttatacacgt   1380
tatactaaca caacaaaaac aaaaacaacg acaacaacaa caacctgcag gatgaaaaac   1440
atcatttcat tagtttctaa gaagaaggct gcatccaaaa atgaagataa aaacatctct   1500
gaatcttcaa gagatatcgt taatcaacaa gaggttttca ataccgaaga tttcgaggaa   1560
ggcaaaaagg actctgcatt cgagttagat cacttggagt ttactaccaa ctccgcacaa   1620
ttaggcgact ctgatgagga caacgaaaac gtcattaacg aaatgaacgc aacagacgat   1680
gcaaacgaag caaactctga agagaaatcc atgaccttga agcaagcatt gttgaagtat   1740
cctaaagccg cattatggtc tatttagtc tccactactt ggtcatgga aggttacgac   1800
actgctttgt tatccgcatt atacgcttta ccagttttc aacgtaagtt tggtacattg   1860
aatggtaaag gttcctatga gattacatcc caatggcaga ttggtcttaa catgtgcgtc   1920
ttgtgtggtg aaatgattgg tttacaaatc accacctata tggttgagtt tatgggtaac   1980
agatacacta tgatcaccgc tttaggtctt ttgactgctt acattttcat tttgtactat   2040
```

```
tgtaagtcct tagccatgat tgctgttggt caaattttgt ccgccatccc ttggggttgt    2100
tttcaatctt tggctgttac ctatgcttct gaagtctgcc cattagcact tagatactat    2160
atgacttcct attctaacat tgctggttg ttcggccaaa tcttcgcatc tggtatcatg     2220
aaaaactcac aagagaactt aggcaattcc gatcttggtt acaaacttcc atttgcttta    2280
cagtggattt ggcctgcccc acttatgatt ggtattttct ttgctccaga atctccttgg    2340
tggcttgtta aaaagatag agttgcagaa gctagaaagt cattatccag aattttgtct     2400
ggtaagggcg ctgaaaagga tattcaagtt gatcttacct aaagcagat tgaattaact     2460 attgaaaagg aaagattatt agcttctaag tctggttcat tctttaactg tttcaagggt    2520
gttaatggtc gtagaaccag attagcatgt ttaacctggg ttgcccaaaa ctcctccggt    2580
gcagttttgt taggttattc tacttacttt ttcgaaagag ctggtatggc aacagacaag    2640
gctttcacat tctcattaat ccagtactgt ttgggtcttg caggcacctt atgttcatgg    2700
gttatttcag gtagagtcgg tagatggact atcttgactt atggtcttgc ttttcaaatg    2760
gtctgtttgt tcattatcgg tggtatgggt tttggttctg gttcctctgc ttccaatggt    2820
gctggtggct tattgttggc attatccttt ttctacaatg caggcatcgg tgctgttgtc    2880
tattgtattg tcgccgaaat tccttcagca gaattgagaa ccaagactat tgttttggct    2940
agaatctgtt acaatttgat ggccgttatc aatgctattt tgaccccata catgttgaac    3000
gtttctgact ggaactgggg tgctaagaca ggcttgtatt ggggtggttt cactgcagtt    3060
actttggctt gggttattat cgacttacca gaaaccactg gtagaacatt ctctgaaatc    3120
aatgaattat tcaaccaagg tgttccagct cgtaagttcg catctactgt cgtcgatcca    3180
ttcggtaagg gtaagaccca acatgattcc ttggccgatg aatccatctc tcaatcttca    3240
tccattaagc aaagagaatt gaatgcagca gataagtgtt aacctgcagg cacgtccgac    3300
ggcggcccac gggtcccagg cctcggagat ccgtccccct tttcctttgt cgatatcatg    3360
taattagtta tgtcacgctt acattcacgc cctcccccca catccgctct aaccgaaaag    3420
gaaggagtta gacaacctga agtctaggtc cctatttatt tttttatagt tatgttagta    3480
ttaagaacgt tatttatatt tcaaatttt ctttttttc tgtacagacg cgtgtacgca     3540
tgtaacatta tactgaaaac cttgcttgag aaggttttgg gacgctcgaa ggctttaatt    3600
tgcaagctac tagtttcttt ccccctctca agctggcgtg aaatgcaacc ttacggcgtc    3660
tacgttacta caaggtccag aaagtgtagg tattgctact attttttattt tttattggtt   3720 ctggagaaat gcagacagtc aatgaacaca actgtctcaa tatgcatcta tgcacatgca    3780
cacacacaca catcacaggt acccctacaa agagaggtct cttgataatg tttcattacc    3840
acgtggcatc cccccccccc ccccaataa acaagtggcc gagttcccct gttgcagagg     3900
aggacaaaaa aaccgctggt gttggtacca ttatgcagca actagcacaa caaacaaccg    3960
acccagacat acaaatcaac aacacttcgc caaagacacc ctttccaggg aggatccact    4020
cccaacgtct ctccataatg tctctgttgg cccatgtctc tgtcgttgac accgtaacca    4080
caccaaccaa cccgtccatt gtactgggat ggtcgtccat agacacctct ccaacgggga    4140
acacctcatt cgtaaaccgc caaggttacc gttcctcctg actcgcccg ttgttgatgc      4200 tgcgcacctg tggttgccca acatggttgt atatcgtgta accacaccaa cacatgtgca    4260
gcacatgtgt ttaaaagagt gtcatggagg tggatcatga tggaagtgga ctttaccact    4320
tgggaactgt ctccactccc gggaagaaaa gacccggcgt atcacgcggt tgcctcaatg    4380
```

```
gggcaatttg gaaggagaaa tatagggaaa atcacgtcgc tctcggacgg ggaagagttc    4440
cagactatga gggggggggg tggtatataa agacaggaga tgtccacccc cagagagagg    4500
aagaagttgg aactttagaa gagagagata actttcccca gtgtccatca atacacaacc    4560
aaacacaaac tctatattta cacatataac cccctccaac caaacacata tgactatttc    4620
tgatcatcca gaaacagaac caaagtggtg gaaagaggcc acaatctatc aaatttaccc    4680
agcaagtttt aaagactcca ataacgatgg ctggggtgat ttaaaaggta tcacttccaa    4740
gttgcagtat attaaagatc ttggcgttga tgctatttgg gtttgtccgt tttatgactc    4800
tcctcaacaa gatatggggt atgatatatc taactacgaa aaggtctggc ccacatacgg    4860
taccaacgag gactgttttg agctaattga caagactcat aagctgggta tgaaattcat    4920
caccgatttg gttatcaacc actgttctac agaacacgaa tggttcaaag agagcagatc    4980
ctcgaagacc aatccgaagc gtgactggtt cttctggaga cctcctaaag gttatgacgc    5040
cgaaggcaag ccaattcctc caaacaattg gaaatctttc tttggtggtt cagcttggac    5100
ttttgatgaa actacaaatg aattttacct ccgtttgttt gcgagtcgtc aagttgactt    5160
gaattgggag aatgaagact gcagaagggc aatctttgaa agtgctgttg gattttggct    5220
ggaccatggt gtagatggtt ttagaatcga taccgctggt ttgtattcga aacgtcctgg    5280
tttaccagat tccccaattt ttgacaaaac ctcgaaatta caacatccaa attggggggtc    5340 tcacaatggt cctaggattc atgaatatca tcaagaacta cacagattta tgaaaaacag    5400
ggtgaaagat ggtagagaaa taatgacagt cggtgaagtt gcccatggaa gtgataatgc    5460
tttatacacc agtgcagcta gatacgaagt cagcgaagtt ttctccttca cgcacgttga    5520
agttggtacc tcgccatttt tccgttataa catagtgccc ttcaccttga aacaatggaa    5580
agaagccatt gcatcgaact tttttgttcat taacggtact gatagttggg ctaccaccta    5640
catcgagaat cacgatcaag cccggtcaat tacgagattt gctgacgatt cgccaaagta    5700
ccgtaaaata tctggtaagc tgttaacatt gctagaatgt tcattgacag gtacgttgta    5760
tgtctatcaa ggtcaggaga taggccagat caatttcaag gaatggccta ttgaaaagta    5820
tgaggacgtt gatgtgaaaa acaactacga gattatcaaa aaaagttttg gtaaaaactc    5880
gaaggaaatg aaggattttt ttaaaggaat cgccctactt tctagagatc attcgagaac    5940
tcccatgcca tggacgaaag ataagcccaa tgctggattt actggcccag atgttaaacc    6000 ttggttttc ttgaatgaat cttttgagca aggaatcaat gttgagcagg aatccagaga    6060
tgatgactca gttctcaatt tttggaaaag ggccttgcaa gccagaaaga aatataagga    6120
gcttatgatt tatggttacg atttccaatt cattgattta gacagtgacc agatctttag    6180
cttcactaaa gagtacgaag acaagacgct gtttgctgct ttgaatttca gtggcgaaga    6240
aattgaattc agcctcccaa gagaaggtgc ttctttatct tttattcttg gaaattatga    6300
tgatactgac gtttcctcca gagttttgaa accatgggaa ggtagaatct acctcgtcaa    6360
ataacctgca ggttgttgga aatatattat tcataaaggc gaaaacattc ccttggtatt    6420
ttattccaaa tttatgatac atagacgtat ttttttatata taaagttata ttattaatga    6480
ttcaagaaaa agttcaaata aactaatgga tcgggcc                             6517
```

<210> SEQ ID NO 6
<211> LENGTH: 584
<212> TYPE: PRT
<213> ORGANISM: Saccharomyces cerevisiae

<400> SEQUENCE: 6

```
Met Thr Ile Ser Asp His Pro Glu Thr Glu Pro Lys Trp Trp Lys Glu
1               5                   10                  15

Ala Thr Ile Tyr Gln Ile Tyr Pro Ala Ser Phe Lys Asp Ser Asn Asn
                20                  25                  30

Asp Gly Trp Gly Asp Leu Lys Gly Ile Thr Ser Lys Leu Gln Tyr Ile
            35                  40                  45

Lys Asp Leu Gly Val Asp Ala Ile Trp Val Cys Pro Phe Tyr Asp Ser
        50                  55                  60

Pro Gln Gln Asp Met Gly Tyr Asp Ile Ser Asn Tyr Glu Lys Val Trp
65                  70                  75                  80

Pro Thr Tyr Gly Thr Asn Glu Asp Cys Phe Glu Leu Ile Asp Lys Thr
                85                  90                  95

His Lys Leu Gly Met Lys Phe Ile Thr Asp Leu Val Ile Asn His Cys
                100                 105                 110

Ser Thr Glu His Glu Trp Phe Lys Glu Ser Arg Ser Ser Lys Thr Asn
            115                 120                 125

Pro Lys Arg Asp Trp Phe Phe Trp Arg Pro Pro Lys Gly Tyr Asp Ala
        130                 135                 140

Glu Gly Lys Pro Ile Pro Pro Asn Asn Trp Lys Ser Phe Phe Gly Gly
145                 150                 155                 160

Ser Ala Trp Thr Phe Asp Glu Thr Thr Asn Glu Phe Tyr Leu Arg Leu
                165                 170                 175

Phe Ala Ser Arg Gln Val Asp Leu Asn Trp Glu Asn Glu Asp Cys Arg
                180                 185                 190

Arg Ala Ile Phe Glu Ser Ala Val Gly Phe Trp Leu Asp His Gly Val
            195                 200                 205

Asp Gly Phe Arg Ile Asp Thr Ala Gly Leu Tyr Ser Lys Arg Pro Gly
        210                 215                 220

Leu Pro Asp Ser Pro Ile Phe Asp Lys Thr Ser Lys Leu Gln His Pro
225                 230                 235                 240

Asn Trp Gly Ser His Asn Gly Pro Arg Ile His Glu Tyr His Gln Glu
                245                 250                 255

Leu His Arg Phe Met Lys Asn Arg Val Lys Asp Gly Arg Glu Ile Met
                260                 265                 270

Thr Val Gly Glu Val Ala His Gly Ser Asp Asn Ala Leu Tyr Thr Ser
            275                 280                 285

Ala Ala Arg Tyr Glu Val Ser Glu Val Phe Ser Phe Thr His Val Glu
        290                 295                 300

Val Gly Thr Ser Pro Phe Phe Arg Tyr Asn Ile Val Pro Phe Thr Leu
305                 310                 315                 320

Lys Gln Trp Lys Glu Ala Ile Ala Ser Asn Phe Leu Phe Ile Asn Gly
                325                 330                 335

Thr Asp Ser Trp Ala Thr Thr Tyr Ile Glu Asn His Asp Gln Ala Arg
                340                 345                 350

Ser Ile Thr Arg Phe Ala Asp Asp Ser Pro Lys Tyr Arg Lys Ile Ser
            355                 360                 365

Gly Lys Leu Leu Thr Leu Leu Glu Cys Ser Leu Thr Gly Thr Leu Tyr
        370                 375                 380

Val Tyr Gln Gly Gln Glu Ile Gly Gln Ile Asn Phe Lys Glu Trp Pro
385                 390                 395                 400

Ile Glu Lys Tyr Glu Asp Val Asp Val Lys Asn Asn Tyr Glu Ile Ile
                405                 410                 415
```

```
Lys Lys Ser Phe Gly Lys Asn Ser Glu Met Lys Asp Phe Lys
            420                 425                 430

Gly Ile Ala Leu Leu Ser Arg Asp His Ser Arg Thr Pro Met Pro Trp
        435                 440                 445

Thr Lys Asp Lys Pro Asn Ala Gly Phe Thr Gly Pro Asp Val Lys Pro
        450                 455                 460

Trp Phe Phe Leu Asn Glu Ser Phe Glu Gln Gly Ile Asn Val Glu Gln
465                 470                 475                 480

Glu Ser Arg Asp Asp Ser Val Leu Asn Phe Trp Lys Arg Ala Leu
                485                 490                 495

Gln Ala Arg Lys Lys Tyr Lys Glu Leu Met Ile Tyr Gly Tyr Asp Phe
            500                 505                 510

Gln Phe Ile Asp Leu Asp Ser Asp Gln Ile Phe Ser Phe Thr Lys Glu
            515                 520                 525

Tyr Glu Asp Lys Thr Leu Phe Ala Ala Leu Asn Phe Ser Gly Glu Glu
        530                 535                 540

Ile Glu Phe Ser Leu Pro Arg Glu Gly Ala Ser Leu Ser Phe Ile Leu
545                 550                 555                 560

Gly Asn Tyr Asp Asp Thr Asp Val Ser Ser Arg Val Leu Lys Pro Trp
                565                 570                 575

Glu Gly Arg Ile Tyr Leu Val Lys
            580

<210> SEQ ID NO 7
<211> LENGTH: 616
<212> TYPE: PRT
<213> ORGANISM: Saccharomyces cerevisiae

<400> SEQUENCE: 7

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Leu Asn
    130                 135                 140

Gly Lys Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205
```

```
Met Ile Ala Val Gly Gln Ile Leu Ser Ala Ile Pro Trp Gly Cys Phe
    210                 215                 220
Gln Ser Leu Ala Val Thr Tyr Ala Ser Glu Val Cys Pro Leu Ala Leu
225                 230                 235                 240
Arg Tyr Tyr Met Thr Ser Tyr Ser Asn Ile Cys Trp Leu Phe Gly Gln
                245                 250                 255
Ile Phe Ala Ser Gly Ile Met Lys Asn Ser Gln Glu Asn Leu Gly Asn
            260                 265                 270
Ser Asp Leu Gly Tyr Lys Leu Pro Phe Ala Leu Gln Trp Ile Trp Pro
        275                 280                 285
Ala Pro Leu Met Ile Gly Ile Phe Phe Ala Pro Glu Ser Pro Trp Trp
    290                 295                 300
Leu Val Arg Lys Asp Arg Val Ala Glu Ala Arg Lys Ser Leu Ser Arg
305                 310                 315                 320
Ile Leu Ser Gly Lys Gly Ala Glu Lys Asp Ile Gln Val Asp Leu Thr
                325                 330                 335
Leu Lys Gln Ile Glu Leu Thr Ile Glu Lys Glu Arg Leu Leu Ala Ser
            340                 345                 350
Lys Ser Gly Ser Phe Phe Asn Cys Phe Lys Gly Val Asn Gly Arg Arg
        355                 360                 365
Thr Arg Leu Ala Cys Leu Thr Trp Val Ala Gln Asn Ser Ser Gly Ala
    370                 375                 380
Val Leu Leu Gly Tyr Ser Thr Tyr Phe Phe Glu Arg Ala Gly Met Ala
385                 390                 395                 400
Thr Asp Lys Ala Phe Thr Phe Ser Leu Ile Gln Tyr Cys Leu Gly Leu
                405                 410                 415
Ala Gly Thr Leu Cys Ser Trp Val Ile Ser Gly Arg Val Gly Arg Trp
            420                 425                 430
Thr Ile Leu Thr Tyr Gly Leu Ala Phe Gln Met Val Cys Leu Phe Ile
        435                 440                 445
Ile Gly Gly Met Gly Phe Gly Ser Gly Ser Ser Ala Ser Asn Gly Ala
    450                 455                 460
Gly Gly Leu Leu Leu Ala Leu Ser Phe Phe Tyr Asn Ala Gly Ile Gly
465                 470                 475                 480
Ala Val Val Tyr Cys Ile Val Ala Glu Ile Pro Ser Ala Glu Leu Arg
                485                 490                 495
Thr Lys Thr Ile Val Leu Ala Arg Ile Cys Tyr Asn Leu Met Ala Val
            500                 505                 510
Ile Asn Ala Ile Leu Thr Pro Tyr Met Leu Asn Val Ser Asp Trp Asn
        515                 520                 525
Trp Gly Ala Lys Thr Gly Leu Tyr Trp Gly Gly Phe Thr Ala Val Thr
    530                 535                 540
Leu Ala Trp Val Ile Ile Asp Leu Pro Glu Thr Thr Gly Arg Thr Phe
545                 550                 555                 560
Ser Glu Ile Asn Glu Leu Phe Asn Gln Gly Val Pro Ala Arg Lys Phe
                565                 570                 575
Ala Ser Thr Val Val Asp Pro Phe Gly Lys Gly Lys Thr Gln His Asp
            580                 585                 590
Ser Leu Ala Asp Glu Ser Ile Ser Gln Ser Ser Ile Lys Gln Arg
        595                 600                 605
Glu Leu Asn Ala Ala Asp Lys Cys
    610                 615
```

<210> SEQ ID NO 8
<211> LENGTH: 5906
<212> TYPE: DNA
<213> ORGANISM: Artificial Sequence
<220> FEATURE:
<223> OTHER INFORMATION: pVL13 integration fragment

<400> SEQUENCE: 8

| | | | | | |
|---|---|---|---|---|---|
| aaacctcggt | agtgcctacc | aatttaatgt | ttgactcctt | gcgttttctc | ctgtcgcgga | 60 |
| caaacggtgc | ggctcccccg | atgattcacg | taataagccg | gagtcaacca | cagaggtccc | 120 |
| ctatgactca | acaaggcctc | gtagaaactc | ggcttctcgg | agaaagagtc | ttttcttttt | 180 |
| cactggaaaa | tattttttt | tcctttatat | tcttttgaac | caaaatgtgg | ctactataaa | 240 |
| agtgccttta | ttccccagct | tttctagcat | gattgagtca | ccttccacaa | tgagtcttct | 300 |
| ttattgttag | tattgtgaat | attatccgtg | cagttttcaa | gaacgtaaat | caacagcagt | 360 |
| gataatacct | tcaaacatat | ggataacttc | gtataatgta | tgctatacga | agttatgctg | 420 |
| caacggcaac | atcaatgtcc | acgttacac  | acctacattt | atatctatat | ttatatttat | 480 |
| atttatttat | ttatgctact | tagcttctat | agttagttaa | tgcactcacg | atattcaaaa | 540 |
| ttgacaccct | tcaactactc | cctactattg | tctactactg | tctactactc | ctctttacta | 600 |
| tagctgctcc | caataggctc | caccaatagg | ctctgtcaat | acattttgcg | ccgccacctt | 660 |
| tcaggttgtg | tcactcctga | aggaccatat | tgggtaatcg | tgcaatttct | ggaagagagt | 720 |
| gccgcgagaa | gtgaggcccc | cactgtaaat | cctcgagggg | gcatggagta | tggggcatgg | 780 |
| aggatggagg | atggggggggg | ggggggaaaa | taggtagcga | aaggaccgc  | tatcacccca | 840 |
| cccggagaac | tcgttgccgg | gaagtcatat | ttcgacactc | cggggagtct | ataaaaggcg | 900 |
| ggttttgtct | tttgccagtt | gatgttgctg | agaggacttg | tttgccgttt | cttccgattt | 960 |
| aacagtatag | aatcaaccac | tgttaattat | acacgttata | ctaacacaac | aaaaacaaaa | 1020 |
| acaacgacaa | caacaacaac | aatgtttgct | ttctactttc | tcaccgcatg | caccactttg | 1080 |
| aagggtgttt | tcggagtttc | tccgagttac | aatggtcttg | gtctcacccc | acagatgggt | 1140 |
| tgggacagct | ggaatacgtt | tgcctgcgat | gtcagtgaac | agctactcct | agacactgct | 1200 |
| gatagaattt | ctgacttggg | gctaaaggat | atgggttaca | agtatgtcat | cctagatgac | 1260 |
| tgttggtcta | gcgcaggga  | ttccgacggt | ttcctcgttg | cagacaagca | caaatttccc | 1320 |
| aacggtatgg | gccatgttgc | agaccacctg | cataataaca | gctttctttt | cggtatgtat | 1380 |
| tcgtctgctg | gtgagtacac | ctgtgctggg | taccctgggt | ctctggggcg | tgaggaagaa | 1440 |
| gatgctcaat | tctttgcaaa | taaccgcgtt | gactacttga | agtatgataa | ttgttacaat | 1500 |
| aaaggtcaat | ttggtacacc | agacgtttct | taccaccgtt | acaaggccat | gtcagatgct | 1560 |
| ttgaataaaa | ctggtaggcc | tatttttctat | tctctatgta | actggggtca | ggatttgaca | 1620 |
| ttttactggg | gctctggtat | cgccaattct | tggagaatga | gcggagatat | tactgctgag | 1680 |
| ttcacccgtc | cagatagcag | atgtcccctgt | gacggtgacg | aatatgattg | caagtacgcc | 1740 |
| ggtttccatt | gttctattat | gaatattctt | aacaaggcag | ctccaatggg | gcaaaatgca | 1800 |
| ggtgttggtg | gttggaacga | tctggacaat | ctagaggtcg | gagtcggtaa | tttgactgac | 1860 |
| gatgaggaaa | aggcccattt | ctctatgtgg | gcaatggtaa | agtccccact | tatcattggt | 1920 |
| gccgacgtga | atcacttaaa | ggcatccttcg | tactcgatct | acagtcaagc | ctctgtcatc | 1980 |
| gcaattaatc | aagatccaaa | gggtattcca | gccacaagag | tctggagata | ttatgtttca | 2040 |
| gacaccgatg | aatatggaca | aggtgaaatt | caaatgtgga | gtggtccgct | tgacaatggt | 2100 |

```
gaccaagtgg ttgctttatt gaatggagga agcgtagcaa gaccaatgaa cacgaccttg    2160
gaagagattt tctttgacag caatttgggt tcaaaggaac tgacatcgac ttgggatatt    2220
tacgacttat gggccaacag agttgacaac tctacggcgt ctgctatcct tgaacagaat    2280
aaggcagcca ccggtattct ctacaatgct acagagcagt cttataaaga cggtttgtct    2340
aagaatgata caagactgtt tggccagaaa attggtagtc tttctccaaa tgctatactt    2400
aacacaactg ttccagctca tggtatcgcc ttctataggt tgagaccctc ggcttaagct    2460
caatgttgag caaagcagga cgagaaaaaa aaaataatg attgttaaga agttcatgaa    2520
aaaaaaaagg aaaaatactc aaatacttat aacagagtga ttaaataata acggcagta    2580 taccctatca ggtattgaga tagttttatt tttgtaggta tataatctga agcctttgaa    2640
ctattttctc gtatatatca tggagtatac attgcattag caacattgca tactagttca    2700
taacttcgta taatgtatgc tatacgaagt tattaattaa caagggcgaa ttctgcagat    2760
atccatcaca ctggcggccg ctcgagcatg catctagagg gcccaattcg ccctatagtg    2820
aggccggccg tccaggagtc catcggttcc tgtcagatgg gatactcttg acgtggaaaa    2880
ttcaaacaga aaaaaaccc ccaataatga aaaataatac tacgttatat ccgtggtatc    2940
ctctatcgta tcgtatcgta gcgtatcgta ccgtaccgta tcacagtata gtctaatatt    3000
ccgtatctta ttgtatccta tcctattcga tcctattgta tttctgtgca ccattttaat    3060
ttctattgct ataatgtcct tattagttgc cactgtgagg tgaccaatgg acgagggcga    3120
gccgttcaga agccgcgaag ggtgttcttc ccatgaattt cttaaggagg gcggctcagc    3180
tccgagagtg aggcgagacg tctcggttag cgtatccccc ttcctcggct tttacaaatg    3240
atgcgctctt aatagtgtgt cgttatcctt ttggcattga cggggagggg aaattgattg    3300
agcgcatcca tattttggcg gactgctgag gacaatggtg gttttccgg gtggcgtggg    3360 ctacaaatga tacgatggtt ttttctttt cggagaaggc gtataaaaag gacacggaga    3420
acccatttat tctaataaca gttgagcttc tttaattatt tgttaatata atattctatt    3480
attatatatt tcttcccaa taaaacaaaa taaaacaaaa cacagcaaaa cacaaaaatt    3540
ctagacgcac gcgtatgact atctcttctg ctcacccaga aactgaacca aagtggtgga    3600
aagaggcaac tttttaccaa atctacccag cttcattcaa ggactccaat gatgatggtt    3660
ggggtgatat gaaaggtatt gcttccaaat tagaatacat taaggaatta ggtgccgatg    3720
ctatttggat ttctccattc tatgattctc cacaagacga tatgggttat gacatcgcta    3780
actatgaaaa ggtttggcca acctatggca ctaatgagga ctgttttgca ttaattgaga    3840
aaacccacaa gttgggcatg aagttcatta ctgatcttgt cattaatcat tgttcatccg    3900
aacatgaatg gttcaaggaa tccagatcct ccaaaactaa tccaaaagga gattggtttt    3960
tctggagacc acctaagggt tatgatgctg aaggtaagcc aattccacca aacaattgga    4020
agtcttactt tggtggttcc gcatggacct tcgacgaaaa gacccaagag ttttacttga    4080
gattattctg ctccacccaa ccagatttga actgggaaaa tgaagattgt agaaaagcaa    4140
tctacgaatc tgcagttggc tattggttag atcacggtgt tgatggtttc agaattgatg    4200
ttggttcact ttactcaaag gttgttggtt tgccagatgc accagttgtt gataaaaact    4260
ctacatggca atcttctgac ccatacactc ttaatggtcc tagaatccat gaatttcatc    4320
aagagatgaa ccagttcatt agaaatagag ttaaggatgg tagagaaatt atgaccgttg    4380
gtgaaatgca acatgcatct gatgaaacta agagattata cacatcagcc tcccgtcacg    4440
```

```
aattgtctga attattcaac ttttcacaca cagacgttgg cacatcccca ttattccgtt    4500
ataacttggt tccattcgaa ttgaaggact ggaaaatcgc attggcagaa ttgtttagat    4560
atatcaatgg tactgattgt tggtctacca tctacttgga aaaccacgac caaccaagat    4620
ccatcactag attcggtgat gactctccta aaaccgtgt catttctggt aagttacttt     4680
ctgtcttatt atccgcctta accggtactt tgtacgtcta tcaaggccag gaattgggtc    4740
aaattaactt taagaattgg ccagtcgaaa agtatgaaga tgtcgaaatc agaaacaact    4800
acaatgcaat taaggaggaa catggtgaaa attcagagga aatgaaaaag ttttttggaag   4860 ctattgctct tatttccaga gatcacgcta gaaccccaat gcaatggtca agagaggaac    4920
ctaacgctgg tttctctggt ccttccgcca agccttggtt ttacttaaac gactccttca    4980
gagaaggtat taacgttgaa gatgaaatta aggacccaaa ttccgtcctt aacttctgga    5040
aggaagcatt gaagtttaga aaggcccata aggatattac cgtttatggt tatgactttg    5100
agtttatcga tttggataac aaaaagttat tctcattcac taaaaagtat aacaacaaga    5160
ccttattcgc tgctttaaac ttctcttctg atgctactga tttcaaaatt cctaatgacg    5220
attcctcttt caagttggag tttggtaact acccaaagaa ggaagttgac gcatcttctc    5280
gtacattgaa gccttgggaa ggtagaatct acatctccga gtaacctgca ggtttgccag    5340
cttactatcc ttcttgaaaa tatgcactct atatcttttta gttcttaatt gcaacacata    5400
gatttgctgt ataacgaatt ttatgctatt ttttaaattt ggagttcagt gataaaagtg    5460
tcacagcgaa tttcctcaca tgtagggacc gaattgttta caagttctct gtaccaccat    5520
ggagacatca aaaattgaaa atctatggaa agatatggac ggtagcaaca agaatatagc    5580
acgagccggc gctagcgagc tcgtctgata tttgctaaat tgaaatgaac cttaccatgc    5640
cacatctata gacatcaaaa ccattttcaa tttgtcgata tcttttgcat atcaaagtaa    5700
taccaagcat gttcaaaaag aaaagaaagc ataactttaa tactctattc gaaacattcc    5760
gatccacaac acattagtct ttttaggccc gttgttcatc tttctattac tttattccta    5820
actgtatttt tataattccg ggtttataaa agattaaact aatatagcgc attcttttg     5880 ggtacaaaca tacataacgg aggttt                                         5906
```

<210> SEQ ID NO 9
<211> LENGTH: 589
<212> TYPE: PRT
<213> ORGANISM: Saccharomyces cerevisiae

<400> SEQUENCE: 9

```
Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ala Ser Lys Leu Glu Tyr
        35                  40                  45

Ile Lys Glu Leu Gly Ala Asp Ala Ile Trp Ile Ser Pro Phe Tyr Asp
    50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110
```

```
Cys Ser Ser Glu His Glu Trp Phe Lys Glu Ser Arg Ser Lys Thr
        115                 120                 125

Asn Pro Lys Arg Asp Trp Phe Trp Arg Pro Pro Lys Gly Tyr Asp
130                 135                 140

Ala Glu Gly Lys Pro Ile Pro Pro Asn Asn Trp Lys Ser Tyr Phe Gly
145                 150                 155                 160

Gly Ser Ala Trp Thr Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
    210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Arg Leu
        275                 280                 285

Tyr Thr Ser Ala Ser Arg His Glu Leu Ser Glu Leu Phe Asn Phe Ser
    290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
    370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
        435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
```

```
                530              535              540
Ser Asp Ala Thr Asp Phe Lys Ile Pro Asn Asp Asp Ser Ser Phe Lys
545                 550              555                 560

Leu Glu Phe Gly Asn Tyr Pro Lys Lys Glu Val Asp Ala Ser Ser Arg
                565              570              575

Thr Leu Lys Pro Trp Glu Gly Arg Ile Tyr Ile Ser Glu
            580              585

<210> SEQ ID NO 10
<211> LENGTH: 6367
<212> TYPE: DNA
<213> ORGANISM: Artificial Sequence
<220> FEATURE:
<223> OTHER INFORMATION: pVL16 integration fragment

<400> SEQUENCE: 10
aaacctcggt agtgcctacc aatttaatgt ttgactcctt gcgttttctc ctgtcgcgga      60
caaacggtgc ggctccccg atgattcacg taataagccg gagtcaacca cagaggtccc     120
ctatgactca acaaggcctc gtagaaactc ggcttctcgg agaaagagtc ttttcttttt     180
cactggaaaa tattttttt tcctttatat tcttttgaac caaaatgtgg ctactataaa      240
agtgccttta ttccccagct tttctagcat gattgagtca ccttccacaa tgagtcttct     300
ttattgttag tattgtgaat attatccgtg cagttttcaa gaacgtaaat caacagcagt     360
gataatacct tcaaacatat gataacttcg tataatgtat gctatacgaa gttatgttgg     420
tggtgtgttt tgttggaacg tacattagat gcataatgcg tgacaccgcc atgatggttg     480
tattctacca atgagacatg gccgctgatc ctgttgtgtg ggtcatggga catcacctct     540
tgggggggat tctcctataa ttggcaccgt gtatgcctca accactaact tccaccctat     600
aactgaatat attacataag caaatctact ttttgtttgt gttgatcgcc atcgttgaaa     660
ttcgcgcaac ttctggtggc tcaacgctgc tgttctatcg gtatcctaag agatgtcttt     720
gccctgagtc tagggtaaac tatccacctt cgttgctgtt tgactagaca gctactaact     780
ttacggtagt aaatgaataa cggctcgctc tcatgatcac ttctctacat caccctaaca     840
agtgtattat ttttttttca ggtgggtgtt gctgttggtg ctagccttag tgccctcgtt     900
aatagttgaa caaacactgg catttggagt ataatgaaaa gggatcacta ccccccgctt     960
cctgttccgc ttctcccttc cggaaaaacc acccaccctt tctttccccc cactaatgta    1020
tgaattttc cgttcccagg ggaatggccc acttggttct ctgttaaccc acacaatttt     1080
gacgcatccc acacaccttt tttttttcta ccccacactt tcccttgaaa atctccaat     1140
ttgaactggc aattttcacc ccccaccact tgcattcatt agtgagtcaa tccatcccgc    1200
ggtcggagat tcggaatcca cctactggta atctgtaatc tatattcccg ctgaccctt     1260
ataaatgaac tattgtcgtc aattgcggta gtgctccaac aaattgtaag gaccttcttt    1320
aacctttcg attcaatcca tctccacata aacctagttg cacacaatgt tactcagatc     1380
actaaactct tctgctcgtt gtgtcaaaca aacaaccaga acaaaggtta ggtatctcag    1440
ccacgtcagt ggtgcaagca tggcgaaacc tacattgaag aacaactcga gagaatccaa    1500
caaatccaga aactatctaa ttgctgctgt gacagcattg ctgtatcaa ctcaattgg      1560
agttgccgta catgtgaagg accccttgta taacgatgct accggcagtg attctccgag    1620
aagtatatct gttgacgagt ttgtcaagca taattcacaa aacgactgtt ggattgcaat    1680
caatggcaag gtttatgatt tcactgattt tattccaaac catccaggtg gggtacctcc    1740
```

```
attagttaat catgctggtt atgatggtac taaactttat gagaaattgc atccaaaagg    1800
tacaattgag aaattcttgc caaaggataa gtttctgggt gtgttagatg gtgaagcgcc    1860
aaaattggaa gcagactatt tggtggacga tgatgaacaa gagagactgg attatttgaa    1920
caacttacct cctttgtcat ctattcagaa tgtttatgat ttcgaatact tggccaagaa    1980
gattttacct aaagatgcct gggcatatta ttcttgtggt gccgatgatg aaatcacaat    2040
gagagaaaac cattatgctt atcaaagagt ttatttcaga ccaagaattt gtgttgatgt    2100
caaggaagtt gatacttctt atgaaatgtt aggcactaaa acctctgttc cttttttatgt   2160
atctgccacc gctttggcta aattaggcca tcctgatggt gaatgctcaa ttgctagagg    2220
cgctggtaag gaaggtgtcg ttcaaatgat ttcgacccct tcctcaatgt cattagatga    2280
aattgccgct gctagaattc caggtgcaac ccaatggttc caattataca ttaatgagga    2340
tagaaatgtc gctaaaggtc tggtcaaaca tgcagaagac ttgggtatga aggctatctt    2400
tataactgtt gatgctcctt ctctaggtaa cagagaaaag gataaaagat taaagtttgt    2460
taatgacacc gatgtcgatt tgggtgattc cgcagatcga aacagtggtg cttcaaaggc    2520
actatcttcg ttcattgatg cttctgtctc ttggaatgac gtcaaagcgg tcaagtcgtg    2580
gactaaattg cctgtcttag ttaaaggtgt tcaaacagtt gaagacgtta ttgaagctta    2640
cgatgctggt tgtcaaggtg ttgttttgtc aaaccacggt ggtaggcaac tagatactgc    2700
tcctcctcca atcgaattat tagctgaaac tgttccaact ttgaagagat tgggtaaatt    2760
aagaccagat tttgaaattt taattgacgg tggtgtcaaa agaggtaccg atattttgaa    2820
agcagtcgca atcggtggcc aagatgtcag agtttcagtt ggtatgggta gaccttctt    2880
atatgccaac tcttgctatg gtgaagcagg tgttagaaaa ttaattcaaa atctaaagga    2940
tgaattagaa atggatatga gattgttggg tgtcactaaa atggaccagc tatcttcgaa    3000
acatgtcgat actaaacgtt tgattggtag agatgcgatc aactatttgt atgataatgt    3060
atacagccca atcgaaaccg ttaaattcaa caatgaagat tgattgttgg aaatatatta    3120
ttcataaagg cgaaaacatt cccttggtat tttattccaa atttatgata catagacgta    3180
tttttttatat ataagttat attattaatg attcaagaaa aagttcaaat aaactaatgg    3240
atcaaccata acttcgtata atgtatgcta tacgaagtta tagatctgcc gtccaggagt    3300
ccatcggttc ctgtcagatg ggatactctt gacgtggaaa attcaaacag aaaaaaaacc    3360
cccaataatg aaaaataata ctacgtttata tccgtggtat cctctatcgt atcgtatcgt    3420
agcgtatcgt accgtaccgt atcacagtat agtctaatat tccgtatctt attgtatcct    3480
atcctattcg atcctattgt atttctgtgc accatttttaa tttctattgc tataatgtcc    3540
ttattagttg ccactgtgag gtgaccaatg gacgagggcg agccgttcag aagccgcgaa    3600
gggtgttctt cccatgaatt tcttaaggag ggcggctcag ctccgagagt gaggcgagac    3660
gtctcggtta gcgtatcccc cttcctcggc ttttacaaat gatgcgctct taatagtgtg    3720
tcgttatcct tttggcattg acgggggagg gaaattgatt gagcgcatcc atattttggc    3780
ggactgctga ggacaatggt ggttttttccg ggtggcgtgg gctacaaatg atacgatggt    3840
tttttctttt tcggagaagg cgtataaaaa ggacacggag aacccattta ttctaataac    3900
agttgagctt ctttaattat ttgttaatat aatattctat tattatatat tttcttccca    3960
ataaacaaa ataaaacaaa acacagcaaa acacaaaaat tctagacgca cgcgtatgac    4020
tatctcttct gctcacccag aaactgaacc aaagtggtgg aaagaggcaa ctttttacca    4080
aatctaccca gcttcattca aggactccaa tgatgatggt tggggtgata tgaaaggtat    4140
```

```
tgcttccaaa ttagaataca ttaaggaatt aggtgccgat gctatttgga tttctccatt    4200
ctatgattct ccacaagacg atatgggtta tgacatcgct aactatgaaa aggtttggcc    4260
aacctatggc actaatgagg actgttttgc attaattgag aaacccaca agttgggcat     4320
gaagttcatt actgatcttg tcattaatca ttgttcatcc gaacatgaat ggttcaagga    4380
atccagatcc tccaaaacta atccaaaaag agattggttt ttctggagac cacctaaggg    4440
ttatgatgct gaaggtaagc caattccacc aaacaattgg aagtcttact ttggtggttc    4500
cgcatggacc ttcgacgaaa agacccaaga gttttacttg agattattct gctccaccca    4560
accagatttg aactgggaaa atgaagattg tagaaaagca atctacgaat ctgcagttgg    4620
ctattggtta gatcacggtg ttgatggttt cagaattgat gttggttcac tttactcaaa    4680
ggttgttggt ttgccagatg caccagttgt tgataaaaac tctacatggc aatcttctga    4740
cccatacact cttaatggtc ctagaatcca tgaatttcat caagagatga accagttcat    4800
tagaaataga gttaaggatg gtagagaaat tatgaccgtt ggtgaaatgc aacatgcatc    4860
tgatgaaact aagagattat acacatcagc ctcccgtcac gaattgtctg aattattcaa    4920
cttttcacac acagacgttg gcacatcccc attattccgt tataacttgg ttccattcga    4980
attgaaggac tggaaaatcg cattggcaga attgttttaga tatatcaatg gtactgattg    5040
ttggtctacc atctacttgg aaaaccacga ccaaccaaga tccatcacta gattcggtga    5100
tgactctcct aaaaaccgtg tcatttctgg taagttactt tctgtcttat tatccgcctt    5160
aaccggtact ttgtacgtct atcaaggcca ggaattgggt caaattaact ttaagaattg    5220
gccagtcgaa aagtatgaag atgtcgaaat cagaaacaac tacaatgcaa ttaaggagga    5280
acatggtgaa aattcagagg aaatgaaaaa gttttttggaa gctattgctc ttatttccag    5340
agatcacgct agaaccccaa tgcaatggtc aagagaggaa cctaacgctg gtttctctgg    5400
tccttccgcc aagccttggt tttacttaaa cgactccttc agagaaggta ttaacgttga    5460
agatgaaatt aaggacccaa attccgtcct taacttctgg aaggaagcat tgaagtttag    5520
aaaggcccat aaggatatta ccgtttatgg ttatgacttt gagtttatcg atttggataa    5580
caaaaagtta ttctcattca ctaaaaagta taacaacaag accttattcg ctgctttaaa    5640
cttctcttct gatgctactg atttcaaaat tcctaatgac gattcctctt tcaagttgga    5700
gtttggtaac tacccaaaga aggaagttga cgcatcttct cgtacattga gccttgggga    5760
aggtagaatc tacatctccg agtaacctgc aggtttgcca gcttactatc cttcttgaaa    5820
atatgcactc tatatctttt agttcttaat tgcaacacat agatttgctg tataacgaat    5880
tttatgctat ttttttaaatt tggagttcag tgataaaagt gtcacagcga atttcctcac    5940
atgtagggac cgaattgttt acaagttctc tgtaccacca tggagacatc aaaaattgaa    6000
aatctatgga agatatgga cggtagcaac aagaatatag cacgagccgg cgctagcgag     6060
ctcgtctgat atttgctaaa ttgaaatgaa ccttaccatg ccacatctat agacatcaaa    6120
accattttca atttgtcgat atcttttgca tatcaaagta ataccaagca tgttcaaaaa    6180
gaaaagaaag cataacttta atactctatt cgaaacattc cgatccacaa cacattagtc    6240
tttttaggcc cgttgttcat ctttctatta ctttattcct aactgtattt ttataattcc    6300
gggtttataa aagattaaac taatatagcg cattcttttt gggtacaaac atacataacg    6360
gaggttt                                                               6367
```

<210> SEQ ID NO 11

```
<211> LENGTH: 9630
<212> TYPE: DNA
<213> ORGANISM: Artificial Sequence
<220> FEATURE:
<223> OTHER INFORMATION: pVB32 plasmid
<220> FEATURE:
<221> NAME/KEY: misc_feature
<222> LOCATION: (5897)..(5897)
<223> OTHER INFORMATION: n is a, c, g, or t
<220> FEATURE:
<221> NAME/KEY: misc_feature
<222> LOCATION: (6283)..(6283)
<223> OTHER INFORMATION: n is a, c, g, or t
<220> FEATURE:
<221> NAME/KEY: misc_feature
<222> LOCATION: (6314)..(6314)
<223> OTHER INFORMATION: n is a, c, g, or t
<220> FEATURE:
<221> NAME/KEY: misc_feature
<222> LOCATION: (6343)..(6343)
<223> OTHER INFORMATION: n is a, c, g, or t
<220> FEATURE:
<221> NAME/KEY: misc_feature
<222> LOCATION: (6347)..(6347)
<223> OTHER INFORMATION: n is a, c, g, or t
<220> FEATURE:
<221> NAME/KEY: misc_feature
<222> LOCATION: (6371)..(6371)
<223> OTHER INFORMATION: n is a, c, g, or t
<220> FEATURE:
<221> NAME/KEY: misc_feature
<222> LOCATION: (6525)..(6525)
<223> OTHER INFORMATION: n is a, c, g, or t
<220> FEATURE:
<221> NAME/KEY: misc_feature
<222> LOCATION: (6543)..(6543)
<223> OTHER INFORMATION: n is a, c, g, or t
<220> FEATURE:
<221> NAME/KEY: misc_feature
<222> LOCATION: (7386)..(7386)
<223> OTHER INFORMATION: n is a, c, g, or t
<220> FEATURE:
<221> NAME/KEY: misc_feature
<222> LOCATION: (7397)..(7397)
<223> OTHER INFORMATION: n is a, c, g, or t

<400> SEQUENCE: 11
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgatta gggtgatggt tcacgtagtg     240
ggccatcgcc ctgatagacg gttttttcgcc ctttgacgtt ggagtccacg ttctttaata     300
gtggactctt gttccaaact ggaacaacac tcaaccctat ctcggtctat tcttttgatt     360
tataagggat tttgccgatt tcggcctatt ggttaaaaaa tgagctgatt taacaaaaat     420
ttaacgcgaa ttttaacaaa atattaacgc ttacaatttc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tggtcgagga     660
gtccatcggt tcctgtcaga tgggatactc ttgacgtgga aaattcaaac agaaaaaaaa     720
ccccaataat gaaaataac actacgttat atccgtggta tcctctatcg tatcgtatcg     780
tagcgtatcg tagcgtaccg tatcacagta tagtctaata ttccgtatct tattgtatcc     840
tatcctattc gatcctattg tatttcagtg caccatttta atttctattg ctataatgtc     900
cttattagtt gccactgtga ggtgaccaat ggacgagggc gagccgttca gaagccgcga     960
```

```
agggtgttct tcccatgaat ttcttaagga gggcggctca gctccgagag tgaggcgaga   1020
cgtctcggtc agcgtatccc ccttcctcgg cttttacaaa tgatgcgctc ttaatagtgt   1080
gtcgttatcc ttttggcatt gacggggag  ggaaattgat tgagcgcatc catattttg    1140 cggactgctg aggacaatgg tggttttcc  gggtggcgtg ggctacaaat gatacgatgg   1200
ttttttcttt tcggagaag  gcgtataaaa aggacacgga gaacccattt attctaaaaa   1260
cagttgagct tctttaatta tttttgata  taatattcta ttattatata ttttcttccc   1320
aataaaacaa aataaaacaa aacacagcaa aacacaaaaa ggatccatgt ctaatttact   1380
tactgttcac caaaacttgc ctgcattacc agttgacgca acctccgatg aagtcagaaa   1440
gaaccttatg gatatgttta gagatagaca agctttctcc gaacatactt ggaaaatgtt   1500
attatccgtt tgtagatcct gggccgcttg gtgtaaactt aacaatagaa aatggtttcc   1560
tgctgaacca gaagacgtca gagattactt actttactta caagctagag gtttggctgt   1620
taaaactatc caacaacact taggtcaatt gaatatgtta cacagaagat ccggtttacc   1680
aagaccatcc gattccaacg cagtttccct tgttatgaga agaattagaa aagaaaatgt   1740
tgacgctggt gaaagagcta aacaagcatt agcatttgaa agaaccgatt tcgatcaagt   1800
tagatcctta atggaaaatt ccgatagatg tcaagatatt agaaacttag ctttcttagg   1860
tattgcttac aacacattat taagaatcgc tgaaattgct agaattagag ttaaagatat   1920
ttcaagaacc gatggcggta gaatgttaat ccacattggc agaacaaaaa ccttagtctc   1980
cacagcaggc gtcgaaaaag cattatcatt aggtgttact aaattagttg aacgttggat   2040 ttccgttcc  ggtgttgcag atgacccaaa caactactta ttctgtcgtg ttagaaaaaa   2100
tggtgttgcc gctccttccg ctacctcaca attatccaca agagcattag aaggcatttt   2160
tgaagctacc cacagactta tttatggtgc aaaagacgat tccggtcaaa gatatttagc   2220
ttggtctggt cattccgcta gagttggtgc cgcaagagac atggcaagag ctggtgtttc   2280
tattcctgaa attatgcaag ccggtggttg gactaatgtt aacattgtta tgaactatat   2340
cagaaactta gattccgaaa caggtgctat ggttagatta cttgaagacg gtgattaagt   2400
taattaacat ctgaatgtaa aatgaacatt aaaatgaatt actaaacttt acgtctactt   2460
tacaatctat aaactttgtt taatcatata acgaaataca ctaatacaca atcctgtacg   2520
tatgtaatac ttttatccat caaggattga gaaaaaaag  taatgattcc ctgggccatt   2580
aaaacttaga ccccccaagct tggataggtc actctctatt ttcgtttctc ccttccctga   2640
tagaagggtg atatgtaatt aagaataata tataatttta taataaaaga attcggcaga   2700
tctggatcga tccccggggc tgcatgcaac ggcaacatca atgtccacgt ttacacacct   2760
acatttatat ctatatttat atttatattt atttatttat gctacttagc ttctatagtt   2820
agttaatgca ctcacgatat tcaaaattga caccccttcaa ctactcccta ctattgtcta   2880
ctactgtcta ctactcctct ttactatagc tgctcccaat aggctccacc aataggctct   2940
gtcaatacat tttgcgccgc cacctttcag gttgtgtcac tcctgaagga ccatattggg   3000
taatcgtgca atttctggaa gagagtgccg cgagaagtga ggcccccact gtaaatcctc   3060
gagggggcat ggagtatggg gcatggagga tggaggatgg gggggggggg ggaaaatagg   3120
tagcgaaagg accgctatc  accccacccg gagaactcgt tgccgggaag tcatatttcg   3180
acactccggg gagtctataa aaggcgggtt ttgtcttttg ccagttgatg ttgctgagag   3240
gacttgtttg ccgtttcttc cgatttaaca gtatagaatc aaccactgtt aattatacac   3300
```

-continued

```
gttatactaa cacaacaaaa acaaaaacaa cgacaacaac aacaacctgc aggaaatgct    3360
tttgcaagct ttccttttcc ttttggctgg ttttgcagcc aaaatatctg catcaatgac    3420
aaacgaaact agcgatagac ctttggtcca cttcacaccc aacaagggct ggatgaatga    3480
cccaaatggg ttgtggtacg atgaaaaaga tgccaaatgg catctgtact ttcaatacaa    3540
cccaaatgac accgtatggg gtacgccatt gttttgggc catgctactt ccgatgattt     3600
gactaattgg gaagatcaac ccattgctat cgctcccaag cgtaacgatt caggtgcttt    3660
ctctggctcc atggtggttg attacaacaa cacgagtggg tttttcaatg atactattga    3720
tccaagacaa agatgcgttg cgatttggac ttataacact cctgaaagtg aagagcaata    3780
cattagctat tctcttgatg gtggttacac ttttactgaa taccaaaaga ccctgtttt     3840 agctgccaac tccactcaat tcagagatcc aaaggtgttc tggtatgaac cttctcaaaa    3900
atggattatg acggctgcca atcacaaga ctacaaaatt gaaatttact cctctgatga     3960
cttgaagtcc tggaagctag aatctgcatt tgccaatgaa ggtttcttag gctaccaata    4020
cgaatgtcca ggtttgattg aagtcccaac tgagcaagat ccttccaaat cttattgggt    4080
catgtttatt tctatcaacc caggtgcacc tgctggcggt tccttcaacc aatattttgt    4140
tggatccttc aatggtactc attttgaagc gtttgacaat caatctagag tggtagattt    4200
tggtaaggac tactatgcct tgcaaacttt cttcaacact gacccaacct acggttcagc    4260
attaggtatt gcctgggctt caaactggga gtacagtgcc tttgtcccaa ctaacccatg    4320
gagatcatcc atgtctttgg tccgcaagtt ttctttgaac actgaatatc aagctaatcc    4380
agagactgaa ttgatcaatt tgaaagccga accaatattg aacattagta atgctggtcc    4440
ctggtctcgt tttgctacta acacaactct aactaaggcc aattcttaca atgtcgattt    4500
gagcaactcg actggtaccc tagagtttga gttggtttac gctgttaaca ccacacaaac    4560
catatccaaa tccgtctttg ccgacttatc actttggttc aagggtttag aagatcctga    4620
agaatatttg agaatggggtt ttgaagtcag tgcttcttcc ttcttttttgg accgtggtaa    4680 ctctaaggtc aagtttgtca aggagaaccc atatttcaca aacagaatgt ctgtcaacaa    4740
ccaaccattc aagtctgaga acgacctaag ttactataaa gtgtacggcc tactggatca    4800
aaacatcttg gaattgtact tcaacgatgg agatgtggtt tctacaaata cctacttcat    4860
gaccaccggt aacgctctag gatctgtgaa catgaccact ggtgtcgata atttgttcta    4920
cattgacaag ttccaagtaa gggaagtaaa atagcctgca ggcacgtccg acggcggccc    4980
acgggtccca ggcctcggag atccgtcccc cttttccttt gtcgatatca tgtaattagt    5040
tatgtcacgc ttacattcac gccctcccc cacatccgct ctaaccgaaa aggaaggagt     5100
tagacaacct gaagtctagg tccctattta ttttttttata gttatgttag tattaagaac    5160
gttatttata tttcaaattt ttctttttttt tctgtacaga cgcgtgtacg catgtaacat    5220
tatactgaaa accttgcttg agaaggtttt gggacgctcg aaggctttaa tttgcaagct    5280
gaattcccgg gccttaccgt cgacgaattt cagcattttc atttcaaggc gatattatgt    5340
ttcactaaac tcaggacagg aatatactaa gaataactac aacatacaca caacataagc    5400
caagatggat caacttaact accaagaaca acaacaattt caaagatcg ttgaacaaaa     5460 gcaaatggct gatttcatga ggctatgaat tcgcccttga tctgggtgta tactgcacaa    5520
cctcattgtt cgggaatttg attctcatct cacatacagg cctgtagtat tgcgccctct    5580
ccttctcctt ctccttctcc ttctccaaga gagacttctc tctcatcgcc ctcgtcatca    5640
atggctgctc gctgtattgt cgttggagca tctcccgata cttctgcaac tgtgataaac    5700
```

```
tcatctcagg tgacccatcc gattctgtat cggtgtctcc atctggggct acatctcggg   5760
ccagtctaga tttaaacttt gcagaacctt cactttgggg gatatacact agtgtctctc   5820
ccgtgactac atcaccgaca ccctcaactg taccattatt attgtcattg ttttcctcta   5880
agttctcgct ttggtcntca tccatctctc cttcgggtgc tgtatcactc ttgatgattt   5940
ctctaaccct aatacggaga ctgtgattgc ctgaaataat acccacatct ttcaacttct   6000
gatgaagtga atctccagag atgaccttca tcagcacttg cacatcaacc acatcaccct   6060
ccttttgagc atccctcatg attccataga ctacatcccg tagcgtctcc ttgttcttgt   6120
acttcttaac aacagtctcg ccacagacat ggccctgat  aatcacctcc tgtctctcct   6180
catggccatc ctggtcgcca ttgtcttcgt cgctcggctc aattgccaat gtagcaccct   6240
gtggaagatt gcttagtctg tatggaacag actcatcaac tcntttgcca ttatgcatta   6300
acttgtactt tcgnccttgg ctaagttgaa aatgtttaca tcnwtcntca agtacattgg   6360
acatgattgt ncctgcattg acatttgtcc ggtaagtcct aaacccactc gctagattca   6420
ctgtaggcat attcaatcac gttccgtttg aaaaaaagga aaccaattta ttatctccag   6480
aaatagttgg cgtcttgcat cttgtttggt cttgatcttt cgtgnttttt ttttttttctg   6540 tcnttttttt tctcctctct ccaacttttt gattttagt gtaccaaatc gcactgctta    6600
tccacattca tcataaagrg ggggggagaa gagggggcaga aaataaaagg ccatgtcacg   6660
tgcctgtgca tttatttgtg tgtgtgtcac gtgctcaaaa tgtcttttttt ttacgttttt    6720 aacattttcc ctttctgtag ttgaatccat ttgcatgagt cgtacatrat gtttgctgta   6780
tttacgttaa gacactaatt caaatgacaa acagctatta ttcttagcca ttaatgcatt   6840
tttgcaaatc tttaactgga tttaactatg gctaggtraa tttgttctgg acatcattgc   6900
cttgacttgt tttagtgccg atgtccttat cacttacact cgtaacacaa cacaacagca   6960
gctaatgttg ttgtgtatcg cttgacccct aataactgat tcttttttga tgaatgttaa   7020
gaagaaacaa acaaraaaat aaaatcaaaa caggcttctt ttgacctctt tcaagagaag   7080
gttttcttgg ttgtttcata taccaagatc tgaatatctt ctattattat acaaaccact   7140
gattatacaa atctattcat cgacagtatg arctacgaaa acacactgat aaaragagtc   7200
atttcttccc cttctttttc ttttttctttt tcttcttctt cttagtatcc ccatcttcat   7260
taactccacc aagtagatcc tctacacccc ccatggccgt taaaaaatgt tcacgaaaga   7320
aatccatatc attattctta ccatccatta aactgtttag atagatggtg atcatctccc   7380
ttgcantgtc tatatcntca acgtcgagta aatgcgacgc aatggtaccc agcttttgtt   7440 cccttagtg agggttaatt gcgcgcttgg cgtaatcatg gtcatagctg tttcctgtgt    7500
gaaattgtta tccgctcaca attccacaca acatacgagc cggaagcata aagtgtaaag   7560
cctggggtgc ctaatgagtg agctaactca cattaattgc gttgcgctca ctgcccgctt   7620
tccagtcggg aaacctgtcg tgccagctgc attaatgaat cggccaacgc gcggggagag   7680
gcggtttgcg tattgggcgc tcttccgctt cctcgctcac tgactcgctg cgctcggtcg   7740
ttcggctgcg gcgagcggta tcagctcact caaaggcggt aatacggtta tccacagaat   7800
caggggataa cgcaggaaag aacatgtgag caaaaggcca gcaaaggcc  aggaaccgta   7860 aaaaggccgc gttgctggcg ttttccata ggctccgccc ccctgacgag catcacaaaa    7920
atcgacgctc aagtcagagg tggcgaaacc cgacaggact ataaagatac caggcgtttc   7980
cccctggaag ctccctcgtg cgctctcctg ttccgaccct gccgcttacc ggatacctgt   8040
```

```
ccgcctttct cccttcggga agcgtggcgc tttctcatag ctcacgctgt aggtatctca    8100
gttcggtgta ggtcgttcgc tccaagctgg gctgtgtgca cgaaccccccc gttcagcccg   8160 accgctgcgc cttatccggt aactatcgtc ttgagtccaa cccggtaaga cacgacttat    8220
cgccactggc agcagccact ggtaacagga ttagcagagc gaggtatgta ggcggtgcta    8280
cagagttctt gaagtggtgg cctaactacg gctacactag aaggacagta tttggtatct    8340
gcgctctgct gaagccagtt accttcggaa aaagagttgg tagctcttga tccggcaaac    8400
aaaccaccgc tggtagcggt ggtttttttg tttgcaagca gcagattacg cgcagaaaaa    8460
aaggatctca agaagatcct ttgatctttt ctacggggtc tgacgctcag tggaacgaaa    8520
actcacgtta agggattttg gtcatgagat tatcaaaaag gatcttcacc tagatccttt    8580
taaattaaaa atgaagtttt aaatcaatct aaagtatata tgagtaaact tggtctgaca    8640
gttaccaatg cttaatcagt gaggcaccta tctcagcgat ctgtctattt cgttcatcca    8700
tagttgcctg actccccgtc gtgtagataa ctacgatacg ggagggctta ccatctggcc    8760
ccagtgctgc aatgataccg cgagacccac gctcaccggc tccagattta tcagcaataa    8820
accagccagc cggaagggcc gagcgcagaa gtggtcctgc aactttatcc gcctccatcc    8880
agtctattaa ttgttgccgg gaagctagag taagtagttc gccagttaat agtttgcgca    8940
acgttgttgc cattgctaca ggcatcgtgg tgtcacgctc gtcgtttggt atggcttcat    9000
tcagctccgg ttcccaacga tcaaggcgag ttacatgatc ccccatgttg tgcaaaaaag    9060
cggttagctc cttcggtcct ccgatcgttg tcagaagtaa gttggccgca gtgttatcac    9120
tcatggttat ggcagcactg cataattctc ttactgtcat gccatccgta agatgctttt    9180
ctgtgactgg tgagtactca accaagtcat tctgagaata gtgtatgcgg cgaccgagtt    9240
gctcttgccc ggcgtcaata cgggataata ccgcgccaca tagcagaact ttaaaagtgc    9300
tcatcattgg aaaacgttct tcggggcgaa aactctcaag gatcttaccg ctgttgagat    9360
ccagttcgat gtaacccact cgtgcaccca actgatcttc agcatctttt actttcacca    9420
gcgtttctgg gtgagcaaaa acaggaaggc aaaatgccgc aaaaaaggga ataagggcga    9480
cacggaaatg ttgaatactc atactcttcc ttttcaata ttattgaagc atttatcagg     9540
gttattgtct catgagcgga tacatatttg aatgtattta gaaaaataaa caaatagggg    9600
ttccgcgcac atttccccga aaagtgccac                                     9630

<210> SEQ ID NO 12
<211> LENGTH: 4738
<212> TYPE: DNA
<213> ORGANISM: Artificial Sequence
<220> FEATURE:
<223> OTHER INFORMATION: pMI454 integration fragment

<400> SEQUENCE: 12
catagttgaa caaacactgg catttggagt ataatgaaaa gggatcacta ccccccgctt      60
cctgttccgc ttctcccttc cggaaaaacc acccacccctt tcttttcccc cactaatgta   120 tgaattttc cgttcccagg ggaatggccc acttggttct ctgttaaccc acacaatttt     180
gacgcatccc acacaccttt ttttttctcta ccccacactt tcccttgaaa aatctccaat   240
ttgaactggc aattttcacc ccccaccact tgcattcatt agtgagtcaa tccatcccgc    300
ggtcggagat tcggaatcca cctactggta atctgtaatc tatattcccg ctgacccttt    360
ataaatgaac tattgtcgtc aattgcggta gtgctccaac aaattgtaag gaccttcttt    420
aaccttttcg attcaatcca tctccacata aacctagttg cacacacctg cagggtacgt    480
```

```
agcatgcact cgcaagctgt gccatcgccc aacggttaat tataagaaat caacatcagc    540
caacaactat tttcgtcccc ctcttttcag tggtaacgag caattacatt agtaagagac    600
tattttcttc agtgatttgt aattttttt cagtgatttg taattctttc tcgaaatatg    660
cgggcttaac ttatccggac attcactaca tgcaaggaaa aacgagaacc gcggagattt    720
cctcagtaag taacaatgat gatctttta cgcttcatca tcactttcca aagttctaag    780
ctataagttc aagcctagat acgctgaaaa actcctgacc aacaatgtaa agaaaacaat    840
tacaattgta aggttgaaaa catctaaaaa tgaaatattt tattgtacat gcacaccctg    900
atagtcattc tcttacttca tccctgaaag acgtggctgt acaagagttg gaatcgcaag    960
gtcatgaggt taaagttagt gatctttatg ctcaaaagtg aaggcctca atagaccgtg    1020 acgacttcga gcagcttttc gcaagaagag aggttaaaaa taccccaagc ttcttatgaa    1080
gcgtatgcca gaggagcatt aacaaaagac gtaaatcagg aacaggaaaa acttatttgg    1140
gcggactttg tcattttgtc gtttcctata tggtggtctt ctatgccggc tagtcgaccc    1200
cctcgagcga tctcgagatt tgctgcaacg gcaacatcaa tgtccacgtt acacaccta    1260 catttatatc tatatttata tttatattta tttatttatg ctacttagct tctatagtta    1320
gttaatgcac tcacgatatt caaaattgac acccttcaac tactccctac tattgtctac    1380
tactgtctac tactcctctt tactatagct gctcccaata ggctccacca ataggctctg    1440
tcaatacatt ttgcgccgcc acctttcagg ttgtgtcact cctgaaggac catattgggt    1500
aatcgtgcaa tttctggaag agagtgccgc gagaagtgag gcccccactg taaatcctcg    1560
agggggcatg gagtatgggg catggaggat ggaggatggg gggggggggg gaaaataggt    1620
agcgaaagga cccgctatca ccccacccgg agaactcgtt gccgggaagt catatttcga    1680
cactccgggg agtctataaa aggcgggttt tgtcttttgc cagttgatgt tgctgagagg    1740
acttgtttgc cgtttcttcc gatttaacag tatagaatca accactgtta attatacacg    1800
ttatactaac acaacaaaaa caaaaacaac gacaacaaca acaacaatgt ttgctttcta    1860 cttttctcacc gcatgcacca ctttgaaggg tgttttcgga gtttctccga gttacaatgg    1920
tcttggtctc accccacaga tgggttggga cagctggaat acgtttgcct gcgatgtcag    1980
tgaacagcta cttctagaca ctgctgatag aatttctgac ttggggctaa aggatatggg    2040
ttacaagtat gtcatcctag atgactgttg gtctagcggc agggattccg acggtttcct    2100
cgttgcagac aagcacaaat ttcccaacgg tatgggccat gttgcagacc acctgcataa    2160
taacagcttt cttttcggta tgtattcgtc tgctggtgag tacacctgtg ctgggtaccc    2220
tgggtctctg gggcgtgagg aagaagatgc tcaattcttt gcaaataacc gcgttgacta    2280
cttgaagtat gataattgtt acaataaagg tcaatttggt acaccagacg tttcttacca    2340
ccgttacaag gccatgtcag atgctttgaa taaaactggt aggcctattt tctattctct    2400
atgtaactgg ggtcaggatt tgacatttta ctggggctct ggtatcgcca attcttggag    2460
aatgagcgga gatattactg ctgagttcac ccgtccagat agcagatgtc cctgtgacgg    2520
tgacgaatat gattgcaagt acgccggttt ccattgttct attatgaata ttcttaacaa    2580
ggcagctcca atgggcaaa atgcaggtgt tggtggttgg aacgatctgg acaatctaga    2640
ggtcggagtc ggtaatttga ctgacgatga ggaaaaggcc catttctcta tgtgggcaat    2700
ggtaaagtcc ccacttatca ttggtgccga cgtgaatcac ttaaaggcat cttcgtactc    2760
gatctacagt caagcctctg tcatcgcaat taatcaagat ccaaagggta ttccagccac    2820
```

| | |
|---|---:|
| aagagtctgg agatatattg tttcagacac cgatgaatat ggacaaggtg aaattcaaat | 2880 |
| gtggagtggt ccgcttgaca atggtgacca agtggttgct ttattgaatg gaggaagcgt | 2940 |
| agcaagacca atgaacacga ccttggaaga gattttcttt gacagcaatt tgggttcaaa | 3000 |
| ggaactgaca tcgacttggg atatttacga cttatgggcc aacagagttg acaactctac | 3060 |
| ggcgtctgct atccttgaac agaataaggc agccaccggt attctctaca atgctacaga | 3120 |
| gcagtcttat aaagacggtt tgtctaagaa tgatacaaga ctgtttggcc agaaaattgg | 3180 |
| tagtctttct ccaaatgcta tacttaacac aactgttcca gctcatggta tcgccttcta | 3240 |
| taggttgaga ccctcggctt aagctcaatg ttgagcaaag caggacgaga aaaaaaaaaa | 3300 |
| taatgattgt taagaagttc atgaaaaaaa aaggaaaaa tactcaaata cttataacag | 3360 |
| agtgattaaa aataaacgg cagtataccc tatcaggtat tgagatagtt ttatttttgt | 3420 |
| aggtatataa tctgaagcct ttgaactatt ttctcgtata tatcatggag tatacattgc | 3480 |
| attagcaaca ttgcatacta gttctagagc ggccgatcca ctcgcaagct gtgccatcgc | 3540 |
| ccaacggtta attataagaa atcaacatca gccaacaact attttcgtcc ccctcttttc | 3600 |
| agtggtaacg agcaattaca ttagtaagag actattttct tcagtgattt gtaattttt | 3660 |
| ttcagtgatt tgtaattctt tctcgaaata tgcgggctta acttatccgg acattcacta | 3720 |
| catgcaagga aaaacgagaa ccgcggagat ttcctcagta agtaacaatg atgatctttt | 3780 |
| tacgcttcat catcactttc caaagttcta agctataagt tcaagcctag atcgctgaa | 3840 |
| aaactcctga ccaacaatgt aaagaaaaca attacaattg taaggttgaa aacatctaaa | 3900 |
| aatgaaatat tttattgtac atgcacaccc tgatagtcat tctcttactt catccctgaa | 3960 |
| agacgtggct gtacaagagt tggaatcgca aggtcatgag gttaaagtta gtgatcttta | 4020 |
| tgctcaaaag tggaaggcct caatagaccg tgacgacttc gagcagcttt cgcaagaaga | 4080 |
| gaggttaaaa ataccccaag cttcttatga agcgtatgcc agaggagcat taacaaaaga | 4140 |
| cgtaaatcag gaacaggaaa aacttatttg ggcggacttt gtcattttgt cgtttcctat | 4200 |
| atggtggtct tctatgccgg ctacccgggg atatctagtt agatagctcc tcctccaatc | 4260 |
| gaattattag ctgaaactgt tccaactttg aagagattgg gtaaattaag accagatttt | 4320 |
| gaaattttaa ttgacggtgg tgtcaaaaga ggtaccgata ttttgaaagc agtcgcaatc | 4380 |
| ggtggccaag atgtcagagt ttcagttggt atgggtagac ctttcttata tgccaactct | 4440 |
| tgctatggtg aagcaggtgt tagaaaatta attcaaaatc taaggatga attagaaatg | 4500 |
| gatatgagat tgttgggtgt cactaaaatg gaccagctat cttcgaaaca tgtcgatact | 4560 |
| aaacgtttga ttggtagaga tgcgatcaac tatttgtatg ataatgtata cagcccaatc | 4620 |
| gaaaccgtta aattcaacaa tgaagattga ttgttggaaa tatattattc ataaaggcga | 4680 |
| aaacattccc ttggtatttt attccaaatt tatgatacat agacgtaggg cccgagct | 4738 |

<210> SEQ ID NO 13
<211> LENGTH: 6250
<212> TYPE: DNA
<213> ORGANISM: Artificial Sequence
<220> FEATURE:
<223> OTHER INFORMATION: pVL4 integration fragment

<400> SEQUENCE: 13

| | |
|---|---:|
| cccgccatga tggttgtatt ctaccaatga gacatggccg ctgatcctgt tgtgtgggtc | 60 |
| atgggacatc acctcttggg gaggattctc ctataattgg caccgtgtat gcctcaacca | 120 |
| ctaacttcca ccctataact gaatatatta cataagcaaa tctacttttt gtttgtgttg | 180 |

```
atcgccatcg ttgaaattcg cgcaacttct ggtggctcaa cgctgctgtt ctatcggtat      240
cctaagagat gtctttgccc tgagtctagg gtaaactatc caccttcgtt gctgtttgac      300
tagacagcta ctaactttac ggtagtaaat gaataacggc tcgctctcat gatcacttct      360
ctacatcacc ctaacaagtg tattattttt tttcaggtgg gtgttgctgt tggtgctagc      420
cttagtgccc tcgttaatag ttgaacaaac actggcattt ggagtataat gaaaagggat      480
cactaccccc cgcttcctgt tccgcttctc ccttccggaa aaaccaccca ccctttcttt      540
tcccccacta atgtatgaat ttttccgttc caggggaat ggcccacttg gttctctgtt       600
aacccacaca attttgacgc atcccacaca ccttttttt tttctacccc cactttccc       660 ttgaaaaatc tccaatttga actggcaatt ttcaccccc accacttgca ttcattagtg       720
agtcaatcca tcccgcggtc ggagattcgg aatccaccta ctggtaatct gtaatctata      780
ttcccgctga cccttgtcga cttgctgcaa cggcaacatc aatgtccacg tttacacacc      840
tacatttata tctatattta tatttattt tatttattta tgctacttag cttctatagt        900
tagttaatgc actcacgata ttcaaaattg acacccttca actactccct actattgtct      960
actactgtct actactcctc tttactatag ctgctcccaa taggctccac caataggctc     1020
tgtcaataca ttttgcgccg ccacctttca ggttgtgtca ctcctgaagg accatattgg     1080
gtaatcgtgc aatttctgga agagagtccg cgagaagtga ggcccccact gtaaatcctc     1140
gagggggcat ggagtatggg gcatggagga tggaggatgg gggggggag aaaataggta      1200 gcgaaaggac ccgctatcac cccacccgga gaactcgttg ccgggaagtc atatttcgac     1260
actccgggga gtctataaaa ggcgggtttc gtcttttgcc agttgatgtt gctgagagga     1320
cttgtttgcc gtttcttccg atttaacagt atagaatcaa ccactgttaa ttatacacgt     1380
tatactaaca caacaaaaac aaaaacaacg acaacaacaa caacctgcag gatgaaaaac     1440
atcatttcat tagtttctaa gaagaaggct gcatccaaaa atgaagataa aaacatctct     1500
gaatcttcaa gagatatcgt taatcaacaa gaggttttca ataccgaaga tttcgaggaa     1560
ggcaaaaagg actctgcatt cgagttagat cacttggagt ttactaccaa ctccgcacaa     1620
ttaggcgact ctgatgagga caacgaaaac gtcattaacg aaatgaacgc aacagacgat     1680
gcaaacgaag caaactctga agagaaatcc atgaccttga agcaagcatt gttgaagtat     1740
cctaaagccg cattatggtc tatttagtc tccactactt ggtcatgga aggttacgac        1800 actgctttgt tatccgcatt atacgcttta ccagttttc aacgtaagtt tggtacattg       1860
aatggtaaag gttcctatga gattacatcc caatggcaga ttggtcttaa catgtgcgtc     1920
ttgtgtggtg aaatgattgg tttacaaatc accacctata tggttgagtt tatgggtaac     1980
agatacacta tgatcaccgc tttaggtctt ttgactgctt acattttcat tttgtactat      2040
tgtaagtcct tagccatgat tgctgttggt caaatttgt ccgccatccc ttggggttgt       2100
tttcaatctt tggctgttac ctatgcttct gaagtctgcc cattagcact tagatactat     2160
atgacttcct attctaacat ttgctggttg ttcggccaaa tcttcgcatc tggtatcatg     2220
aaaaactcac aagagaactt aggcaattcc gatcttggtt acaaacttcc atttgcttta     2280
cagtggattt ggcctgcccc acttatgatt ggtattttct ttgctccaga atctccttgg     2340
tggcttgtta gaaaagatag agttgcagaa gctagaaagt cattatccag aattttgtct     2400
ggtaagggcg ctgaaaagga tattcaagtt gatcttacct taaagcagat tgaattaact     2460
attgaaaagg aaagattatt agcttctaag tctggttcat tctttaactg tttcaagggt     2520
```

-continued

```
gttaatggtc gtagaaccag attagcatgt ttaacctggg ttgcccaaaa ctcctccggt    2580
gcagttttgt taggttattc tacttacttt ttcgaaagag ctggtatggc aacagacaag    2640
gctttcacat tctcattaat ccagtactgt ttgggtcttg caggcacctt atgttcatgg    2700
gttatttcag gtagagtcgg tagatggact atcttgactt atggtcttgc ttttcaaatg    2760
gtctgtttgt tcattatcgg tggtatgggt tttggttctg gttcctctgc ttccaatggt    2820
gctggtggct tattgttggc attatccttt ttctacaatg caggcatcgg tgctgttgtc    2880
tattgtattg tcgccgaaat tccttcagca gaattgagaa ccaagactat tgttttggct    2940
agaatctgtt acaatttgat ggccgttatc aatgctattt tgaccccata catgttgaac    3000
gtttctgact ggaactgggg tgctaagaca ggcttgtatt ggggtggttt cactgcagtt    3060
actttggctt gggttattat cgacttacca gaaaccactg gtagaacatt ctctgaaatc    3120
aatgaattat tcaaccaagg tgttccagct cgtaagttcg catctactgt cgtcgatcca    3180
ttcggtaagg gtaagaccca acatgattcc ttggccgatg aatccatctc tcaatcttca    3240
tccattaagc aaagagaatt gaatgcagca gataagtgtt aacctgcagg cacgtccgac    3300
ggcggcccac gggtcccagg cctcggagat ccgtcccccct tttcctttgt cgatatcatg    3360
taattagtta tgtcacgctt acattcacgc cctcccccca catccgctct aaccgaaaag    3420
gaaggagtta gacaacctga agtctaggtc cctatttatt tttttatagt tatgttagta    3480
ttaagaacgt tatttatatt tcaaattttt cttttttttc tgtacagacg cgtgtacgca    3540
tgtaacatta tactgaaaac cttgcttgag aaggttttgg gacgctcgaa ggctttaatt    3600
tgcaagctac tagcgcaggg ataacttcgt ataatgtatg ctatacgaag ttatgctgca    3660
acggcaacat caatgtccac gtttacacac ctacatttat atctatattt atatttatat    3720
ttatttattt atgctactta gcttctatag ttagttaatg cactcacgat attcaaaatt    3780
gacaccctta aactactccc tactattgtc tactactgtc tactactcct ctttactata    3840
gctgctccca ataggctcca ccaataggct ctgtcaatac attttgcgcc gccacctttc    3900
aggttgtgtc actcctgaag gaccatattg ggtaatcgtg caatttctgg aagagagtcc    3960
gcgagaagta aggcccccac tgtaaatcct cgaggggggca tggagtatgg ggcatggagg    4020
atggaggatg gggggggggg aaaataggta gcgaaaggac ccgctatcac cccacccgga    4080
gaactcgttg ccgggaagtc atatttcgac actccgggga gtctataaaa ggcgggtttt    4140
gtcttttgcc agttgatgtt gctgagagga cttgtttgcc gtttcttccg atttaacagt    4200
atagaatcaa ccactgttaa ttatacacgt tatactaaca caacaaaaac aaaaacaacg    4260
acaacaacaa caacaatgtt tgctttctac tttctcaccg catgcaccac tttgaagggt    4320
gttttcggag tttctccgag ttacaatggt cttggtctca ccccacagat gggttgggac    4380
agctggaata cgtttgcctg cgatgtcagt gaacagctac ttctagacac tgctgataga    4440
atttctgact tggggctaaa ggatatgggt tacaagtatg tcatcctaga tgactgttgg    4500
tctagcggca gggattccga cggtttcctc gttgcagaca agcacaaatt tcccaacggt    4560
atgggccatg ttgcagacca cctgcataat aacagctttc ttttcggtat gtattcgtct    4620
gctggtgagt acacctgtgc tgggtaccct gggtctctgg ggcgtgagga agaagatgct    4680
caattctttg caaataaccg cgttgactac ttgaagtatg ataattgtta caataaaggt    4740
caatttggta caccagacgt ttcttaccac cgttacaagg ccatgtcaga tgctttgaat    4800
aaaactggta ggcctatttt ctattctcta tgtaactggg gtcaggattt gacatttttac    4860
tggggctctg gtatcgccaa ttcttggaga atgagcggag atattactgc tgagttcacc    4920
```

```
cgtccagata gcagatgtcc ctgtgacggt gacgaatatg attgcaagta cgccggtttc    4980
cattgttcta ttatgaatat tcttaacaag gcagctccaa tggggcaaaa tgcaggtgtt    5040
ggtggttgga acgatctgga caatctagag gtcggagtcg gtaatttgac tgacgatgag    5100
gaaaaggccc atttctctat gtgggcaatg gtaaagtccc cacttatcat tggtgccgac    5160
gtgaatcact taaaggcatc ttcgtactcg atctacagtc aagcctctgt catcgcaatt    5220
aatcaagatc caaagggtat tccagccaca agagtctgga gatattatgt ttcagacacc    5280
gatgaatatg gacaaggtga aattcaaatg tggagtggtc cgcttgacaa tggtgaccaa    5340
gtggttgctt tattgaatgg aggaagcgta gcaagaccaa tgaacacgac cttggaagag    5400
attttctttg acagcaattt gggttcaaag gaactgacat cgacttggga tatttacgac    5460
ttatgggcca acagagttga caactctacg gcgtctgcta ccttgaaaca gaataaggca    5520
gccaccggta ttctctacaa tgctacagag cagtcttata aagacggttt gtctaagaat    5580
gatacaagac tgtttggcca gaaaattggt agtctttctc caaatgctat acttaacaca    5640
actgttccag ctcatggtat cgccttctat aggttgagac cctcggctta agctcaatgt    5700
tgagcaaagc aggacgagaa aaaaaaaaat aatgattgtt aagaagttca tgaaaaaaaa    5760
aagaaaaaat actcaaatac ttataacaga gtgattaaat aataaacgac agtatacccc    5820
atcaggtatt cagatagttt tattttttgta ggtatataat ctgaagcctt tgaactattt    5880
tctcgtatat atcatggagt atacattgca ttagcaacat tgcatactag ttcataactt    5940
cgtataatgt atgctatacg aagttattaa ttaacaaggg cgaattcagc ctcccaagag    6000
aaggtgcttc tttatctttt attcttggaa attatgatga tactgacgtt tcctccagag    6060
ttttgaaacc atgggaaggt agaatctacc tcgtcaaata acctgcaggt tgttggaaat    6120
atattattca taaaggcgaa acattccct tggtatttta ttccaaattt atgatacata    6180
gacgtatttt ttatatataa agttatatta ttaatgattc aagaaaaagt tcaaataaac    6240
taatggatcg                                                          6250
```

<210> SEQ ID NO 14
<211> LENGTH: 5906
<212> TYPE: DNA
<213> ORGANISM: Artificial Sequence
<220> FEATURE:
<223> OTHER INFORMATION: pVL14 integration fragment

<400> SEQUENCE: 14

```
aaacctcggt agtgcctacc aatttaatgt ttgactcctt gcgttttctc ctgtcgcgga      60
caaacggtgc ggctcccccg atgattcacg taataagccg gagtcaacca cagaggtccc     120
ctatgactca acaaggcctc gtagaaactc ggcttctcgg agaaagagtc tttctttttt     180
cactggaaaa tattttttt tcctttatat tcttttgaac caaaatgtgg ctactataaa     240
agtgccttta ttccccagct tttctagcat gattgagtca ccttccacaa tgagtcttct     300
ttattgttag tattgtgaat attatccgtg cagttttcaa gaacgtaaat caacagcagt     360
gataatacct tcaaacatat ggataacttc gtataatgta tgctatacga agttatgctg     420
caacggcaac atcaatgtcc acgtttacac acctacattt atatctatat ttatatttat     480
atttatttat ttatgctact agcttctat agttagttaa tgcactcacg atattcaaaa     540
ttgacaccct tcaactactc cctactattg tctactactg tctactactc ctctttacta     600
tagctgctcc caataggctc caccaatagg ctctgtcaat acattttgcg ccgccacctt     660
```

```
tcaggttgtg tcactcctga aggaccatat tgggtaatcg tgcaatttct ggaagagagt    720
gccgcgagaa gtgaggcccc cactgtaaat cctcgagggg gcatggagta tggggcatgg    780
aggatggagg atggggggggg gggggaaaa taggtagcga aaggacccgc tatcacccca    840
cccggagaac tcgttgccgg gaagtcatat ttcgacactc cggggagtct ataaaaggcg    900
ggttttgtct tttgccagtt gatgttgctg agaggacttg tttgccgttt cttccgattt    960
aacagtatag aatcaaccac tgttaattat acacgttata ctaacacaac aaaaacaaaa   1020
acaacgacaa caacaacaac aatgtttgct ttctactttc tcaccgcatg caccactttg   1080
aagggtgttt tcggagtttc tccgagttac aatggtcttg gtctcaccccc acagatgggt   1140 tgggacagct ggaatacgtt tgcctgcgat gtcagtgaac agctacttct agacactgct   1200
gatagaattt ctgacttggg gctaaaggat atgggttaca agtatgtcat cctagatgac   1260
tgttggtcta gcggcaggga ttccgacggt ttcctcgttg cagacaagca caaatttccc   1320
aacggtatgg gccatgttgc agaccacctg cataataaca gctttctttt cggtatgtat   1380
tcgtctgctg gtgagtacac ctgtgctggg taccctgggt ctctggggcg tgaggaagaa   1440
gatgctcaat tctttgcaaa taaccgcgtt gactacttga agtatgataa ttgttacaat   1500
aaaggtcaat ttggtacacc agacgtttct taccaccgtt acaaggccat gtcagatgct   1560
ttgaataaaa ctggtaggcc tattttctat tctctatgta actggggtca ggatttgaca   1620
ttttactggg gctctggtat cgccaattct tggagaatga gcggagatat tactgctgag   1680
ttcacccgtc cagatagcag atgtccctgt gacggtgacg aatatgattg caagtacgcc   1740
ggtttccatt gttctattat gaatattctt aacaaggcag ctccaatggg gcaaaatgca   1800
ggtgttggtg gttggaacga tctggacaat ctagaggtcg gagtcggtaa tttgactgac   1860
gatgaggaaa aggcccattt ctctatgtgg gcaatggtaa agtccccact tatcattggt   1920
gccgacgtga atcacttaaa ggcatcttcg tactcgatct acagtcaagc ctctgtcatc   1980
gcaattaatc aagatccaaa gggtattcca gccacaagag tctggagata ttatgtttca   2040
gacaccgatg aatatggaca aggtgaaatt caaatgtgga gtggtccgct tgacaatggt   2100
gaccaagtgg ttgctttatt gaatggagga agcgtagcaa gaccaatgaa cacgaccttg   2160
gaagagattt tctttgacag caatttgggt tcaaggaac tgacatcgac ttgggatatt   2220
tacgacttat gggccaacag agttgacaac tctacggcgt ctgctatcct tgaacagaat   2280
aaggcagcca ccggtattct ctacaatgct acagagcagt cttataaaga cggtttgtct   2340
aagaatgata caagactgtt tggccagaaa attggtagtc tttctccaaa tgctatactt   2400
aacacaactg ttccagctca tggtatcgcc ttctataggt tgagaccctc ggcttaagct   2460
caatgttgag caaagcagga cgagaaaaaa aaaataatg attgttaaga agttcatgaa   2520 aaaaaaagg aaaaatactc aaatacttat aacagagtga ttaaataata aacggcagta   2580
taccctatca ggtattgaga tagttttatt tttgtaggta tataatctga agcctttgaa   2640
ctattttctc gtatatatca tggagtatac attgcattag caacattgca tactagttca   2700
taacttcgta taatgtatgc tatacgaagt tattaattaa caaggcgaa ttctgcagat   2760 atccatcaca ctggcggccg ctcgagcatg catctagagg gcccaattcg ccctatagtg   2820
aggccggccg tccaggagtc catcggttcc tgtcagatgg gatactcttg acgtggaaaa   2880
ttcaaacaga aaaaaaaccc ccaataatga aaaataatac tacgttatat ccgtggtatc   2940
ctctatcgta tcgtatcgta gcgtatcgta ccgtaccgta tcacagtata gtctaatatt   3000
ccgtatctta ttgtatccta tcctattcga tcctattgta tttctgtgca ccatttaaat   3060
```

```
ttctattgct ataatgtcct tattagttgc cactgtgagg tgaccaatgg acgagggcga    3120
gccgttcaga agccgcgaag ggtgttcttc ccatgaattt cttaaggagg gcggctcagc    3180
tccgagagtg aggcgagacg tctcggttag cgtatccccc ttcctcggct tttacaaatg    3240
atgcgctctt aatagtgtgt cgttatcctt ttggcattga cggggagggg aaattgattg    3300
agcgcatcca tattttggcg gactgctgag gacaatggtg gttttccgg gtggcgtggg     3360 ctacaaatga tacgatggtt ttttctttt cggagaaggc gtataaaaag gacacggaga     3420
acccatttat tctaataaca gttgagcttc tttaattatt tgttaatata atattctatt    3480
attatatatt ttcttcccaa taaaacaaaa taaaacaaaa cacagcaaaa cacaaaaatt    3540
ctagacgcac gcgtatgact atttcttctg cacatccaga gacagaacca agtggtgga    3600 aagaggccac gttctatcaa atttacccag caagtttcaa agactctaat gacgatggct    3660
ggggtgatat gaagggtatt tcctccaagt tggagtatat caaggagctt ggtgtcgatg    3720
ccatttggat ctcaccattc tacgactcgc cacaagatga tatgggttac gatattgcca    3780
actacgaaaa ggtctggcca acctacggta cgaacgagga ctgctttgcc ttgatcgaaa    3840
agacacataa acttggtatg aaatttatca ccgacttggt catcaatcac tgttccagcg    3900
aacatgaatg gttcaaagag agcagatcct cgaagaccaa tccgaagcgt gactggttct    3960
tctggagacc tcctaagggt tatgacgccg aaggcaagcc aattcctcca ataattgga    4020 agtcctattt tggtggttcc gcatggacct tcgatgaaaa gacacaagaa ttctacttgc    4080
gtttgttttg ctccactcaa cctgatttga attgggagaa tgaagactgt agaaaggcaa    4140
tctacgaaag tgccgttgga tactggttag accatggtgt agacggcttt agaattgatg    4200
tcggaagttt gtactccaaa gttgtaggtt taccagatgc ccctgttgtt gacaaaaacc    4260
cgacttggca atccagtgat ccatacacat tgaatggacc acgtattcac gagttccatc    4320
aagaaatgaa tcaattcatc agaaacagag tgaaggatgg cagggagatt atgacagttg    4380
gtgaaatgca acatgcttcc gacgaaacta agagactta tacgagtgct tcaagacacg    4440
aacttagtga gttatttaac ttttcccaca ctgatgtggg gacttcacct tgttccgtt    4500 acaacttggt cccatttgaa ctgaaggatt ggaagattgc ccttgctgag ctgttcaggt    4560
tcattaatgg tacagattgt tggtcaacaa tctatctgga aaatcacgac caacctcgtt    4620
caattacgag atttggtgac gattctccta agaaccgtgt tatttctggt aagttactct    4680
ctgtgttgct aagtgccttg accggtactc tatatgtgta tcagggacaa gagcttggcc    4740
aaatcaattt caagaactgg cctgttgaaa agtacgagga tgtcgaaatc agaaacaact    4800
acaatgcaat taaagaagag catggggaaa actcagagga gatgaaaaag ttttagaag     4860 ccattgccat tatctccagg gaccatgcta gaacacctat gcaatggtct cgtgaggagc    4920
caaatgctgg ttttctggt cctagtgcta aaccatggtt ttacttgaac gactctttca    4980
gagaaggcat taacgtcgaa gatgaaatca aggatcccaa ctcggttttg aacttctgga    5040
aggaggcctt gaagtttaga aaggcgcata aagacattac tgtgtacgga tacgattttg    5100
agtttattga tttagacaat aagaagttgt ttagcttcac aaagaagtac aacaataaaa    5160
cattgtttgc ggccttgaac tttagctctg atgcgacaga tttcaagatt ccaaatgatg    5220
attcatcgtt caagttagag tttggaaact atccaaagaa ggaggtagat gcctcttcca    5280
gaacattgaa gccatgggaa ggaagaatat atatcagcga atgacctgca ggtttgccag    5340
cttactatcc ttcttgaaaa tatgcactct atatctttta gttcttaatt gcaacacata    5400
```

```
gatttgctgt ataacgaatt ttatgctatt ttttaaattt ggagttcagt gataaaagtg    5460
tcacagcgaa tttcctcaca tgtagggacc gaattgttta caagttctct gtaccaccat    5520
ggagacatca aaaattgaaa atctatggaa agatatggac ggtagcaaca agaatatagc    5580
acgagccggc gctagcgagc tcgtctgata tttgctaaat tgaaatgaac cttaccatgc    5640
cacatctata gacatcaaaa ccattttcaa tttgtcgata tcttttgcat atcaaagtaa    5700
taccaagcat gttcaaaaag aaagaaagc ataactttaa tactctattc gaaacattcc    5760
gatccacaac acattagtct ttttaggccc gttgttcatc tttctattac tttattccta    5820
actgtatttt tataattccg ggtttataaa agattaaact aatatagcgc attcttttg    5880 ggtacaaaca tacataacgg aggttt                                         5906
```

<210> SEQ ID NO 15
<211> LENGTH: 6367
<212> TYPE: DNA
<213> ORGANISM: Artificial Sequence
<220> FEATURE:
<223> OTHER INFORMATION: pVL17 integration fragment

<400> SEQUENCE: 15

```
aaacctcggt agtgcctacc aatttaatgt ttgactcctt gcgttttctc ctgtcgcgga      60
caaacggtgc ggctcccccg atgattcacg taataagccg gagtcaacca cagaggtccc     120
ctatgactca acaaggcctc gtagaaactc ggcttctcgg agaaagagtc ttttcttttt     180
cactggaaaa tattttttt tcctttatat tcttttgaac caaaatgtgg ctactataaa     240
agtgccttta ttccccagct tttctagcat gattgagtca ccttccacaa tgagtcttct     300
ttattgttag tattgtgaat attatccgtg cagttttcaa gaacgtaaat caacagcagt     360
gataatacct tcaaacatat gataacttcg tataatgtat gctatacgaa gttatgttgg     420
tggtgtgttt tgttggaacg tacattagat gcataatgcg tgacaccgcc atgatggttg     480
tattctacca atgagacatg gccgctgatc ctgttgtgtg ggtcatggga catcacctct     540 tggggggggat tctcctataa ttggcaccgt gtatgcctca accactaact tccaccctat     600
aactgaatat attacataag caaatctact ttttgtttgt gttgatcgcc atcgttgaaa     660
ttcgcgcaac ttctggtggc tcaacgctgc tgttctatcg gtatcctaag agatgtcttt     720
gccctgagtc tagggtaaac tatccacctt cgttgctgtt tgactagaca gctactaact     780
ttacggtagt aaatgaataa cggctcgctc tcatgatcac ttctctacat caccctaaca     840
agtgtattat tttttttca ggtgggtgtt gctgttggtg ctagccttag tgccctcgtt     900
aatagttgaa caaacactgg catttggagt ataatgaaaa gggatcacta ccccccgctt     960
cctgttccgc ttctcccttc cggaaaaacc acccaccctt tcttttcccc cactaatgta    1020 tgaattttc cgttcccagg ggaatggccc acttggttct ctgttaaccc acacaatttt    1080
gacgcatccc acacaccttt ttttttcta ccccacactt tcccttgaaa atctccaat    1140 ttgaactggc aattttcacc ccccaccact tgcattcatt agtgagtcaa tccatcccgc    1200
ggtcggagat tcggaatcca cctactggta atctgtaatc tatattcccg ctgaccttt    1260 ataaatgaac tattgtcgtc aattgcggta gtgctccaac aaattgtaag gaccttcttt    1320
aaccttttcg attcaatcca tctccacata aacctagttg cacacaatgt tactcagatc    1380
actaaactct tctgctcgtt gtgtcaaaca acaaccagaa acaaggtta ggtatctcag    1440 ccacgtcagt ggtgcaagca tggcgaaacc tacattgaag acaactcga gagaatccaa    1500 caaatccaga aactatctaa ttgctgctgt gacagcattg gctgtatcaa cctcaattgg    1560
```

-continued

```
agttgccgta catgtgaagg acccottgta taacgatgct accggcagtg attctccgag    1620
aagtatatct gttgacgagt ttgtcaagca taattcacaa aacgactgtt ggattgcaat    1680
caatggcaag gtttatgatt tcactgattt tattccaaac catccaggtg gggtacctcc    1740
attagttaat catgctggtt atgatggtac taaactttat gagaaattgc atccaaaagg    1800
tacaattgag aaattcttgc caaaggataa gtttctgggt gtgttagatg gtgaagcgcc    1860
aaaattggaa gcagactatt tggtggacga tgatgaacaa gagagactgg attatttgaa    1920
caacttacct cctttgtcat ctattcagaa tgtttatgat ttcgaatact tggccaagaa    1980
gattttacct aaagatgcct gggcatatta ttcttgtggt gccgatgatg aaatcacaat    2040
gagagaaaac cattatgctt atcaaagagt ttatttcaga ccaagaattt gtgttgatgt    2100
caaggaagtt gatacttctt atgaaatgtt aggcactaaa acctctgttc cttttttatgt    2160 atctgccacc gctttggcta aattaggcca tcctgatggt gaatgctcaa ttgctagagg    2220
cgctggtaag gaaggtgtcg ttcaaatgat ttcgaccctt tcctcaatgt cattagatga    2280
aattgccgct gctagaattc aggtgcaacc ccaatggttc caattataca ttaatgagga    2340
tagaaatgtc gctaaaggtc tggtcaaaca tgcagaagac ttgggtatga aggctatctt    2400
tataactgtt gatgctcctt ctctaggtaa cagagaaaag gataaaagat taaagtttgt    2460
taatgacacc gatgtcgatt tgggtgattc cgcagatcga aacagtggtg cttcaaaggc    2520
actatcttcg ttcattgatg cttctgtctc ttggaatgac gtcaaagcgg tcaagtcgtg    2580
gactaaattg cctgtcttag ttaaaggtgt caaacagtt gaagacgtta ttgaagctta    2640
cgatgctggt tgtcaaggtg ttgttttgtc aaaccacggt ggtaggcaac tagatactgc    2700
tcctcctcca atcgaattat tagctgaaac tgttccaact ttgaagagat tgggtaaatt    2760
aagaccagat tttgaaattt taattgacgg tggtgtcaaa agaggtaccg atattttgaa    2820
agcagtcgca atcggtggcc aagatgtcag agtttcagtt ggtatgggta gaccttctt    2880 atatgccaac tcttgctatg gtgaagcagg tgttagaaaa ttaattcaaa atctaaagga    2940
tgaattagaa atggatatga gattgttggg tgtcactaaa atggaccagc tatcttcgaa    3000
acatgtcgat actaaacgtt tgattggtag agatgcgatc aactatttgt atgataatgt    3060
atacagccca atcgaaaccg ttaaattcaa caatgaagat tgattgttgg aaatatatta    3120
ttcataaagg cgaaaacatt cccttggtat tttattccaa atttatgata catagacgta    3180
ttttttatat ataagttat attattaatg attcaagaaa aagttcaaat aaactaatgg    3240
atcaaccata acttcgtata atgtatgcta tacgaagtta tagatctgcc gtccaggagt    3300
ccatcggttc ctgtcagatg ggatactctt gacgtggaaa attcaaacag aaaaaaaacc    3360
cccaataatg aaaaataata ctacgttata tccgtggtat cctctatcgt atcgtatcgt    3420
agcgtatcgt accgtaccgt atcacagtat agtctaatat tccgtatctt attgtatcct    3480
atcctattcg atcctattgt atttctgtgc accattttaa tttctattgc tataatgtcc    3540
ttattagttg ccactgtgag gtgaccaatg gacgagggcg agccgttcag aagccgcgaa    3600
gggtgttctt cccatgaatt tcttaaggag ggcggctcag ctccgagagt gaggcgagac    3660
gtctcggtta gcgtatcccc cttcctcggc ttttacaaat gatgcgctct taatagtgtg    3720
tcgttatcct tttggcattg acgggggagg gaaattgatt gagcgcatcc atattttggc    3780
ggactgctga ggacaatggt ggttttccg ggtggcgtgg gctacaaatg atacgatggt    3840
tttttctttt tcggagaagg cgtataaaaa ggacacggag aacccattta ttctaataac    3900
```

-continued

```
agttgagctt ctttaattat tgttaatat aatattctat tattatatat tttcttccca   3960
ataaaacaaa ataaaacaaa acacagcaaa acacaaaaat tctagacgca cgcgtatgac   4020
tatttcttct gcacatccag agacagaacc aaagtggtgg aaagaggcca cgttctatca   4080
aatttaccca gcaagtttca aagactctaa tgacgatggc tggggtgata tgaagggtat   4140
ttcctccaag ttggagtata tcaaggagct tggtgtcgat gccatttgga tctcaccatt   4200
ctacgactcg ccacaagatg atatgggtta cgatattgcc aactacgaaa aggtctggcc   4260
aacctacggt acgaacgagg actgctttgc cttgatcgaa aagacacata aacttggtat   4320
gaaatttatc accgacttgg tcatcaatca ctgttccagc gaacatgaat ggttcaaaga   4380
gagcagatcc tcgaagacca atccgaagcg tgactggttc ttctggagac ctcctaaggg   4440
ttatgacgcc gaaggcaagc caattcctcc aaataattgg aagtcctatt ttggtggttc   4500
cgcatggacc ttcgatgaaa agacacaaga attctacttg cgtttgtttt gctccactca   4560
acctgatttg aattgggaga tgaagactg tagaaaggca atctacgaaa gtgccgttgg   4620
atactggtta gaccatggtg tagacggctt tagaattgat gtcggaagtt tgtactccaa   4680
agttgtaggt ttaccagatg cccctgttgt tgacaaaaac ccgacttggc aatccagtga   4740
tccatacaca ttgaatggac cacgtattca cgagttccat caagaaatga atcaattcat   4800
cagaaacaga gtgaaggatg gcagggagat tatgacagtt ggtgaaatgc aacatgcttc   4860
cgacgaaact aagagacttt atacgagtgc ttcaagacac gaacttagtg agttatttaa   4920
ctttcccac actgatgtgg ggacttcacc tttgttccgt tacaacttgg tcccatttga   4980
actgaaggat tggaagattg cccttgctga gctgttcagg ttcattaatg gtacagattg   5040
ttggtcaaca atctatctgg aaaatcacga ccaacctcgt tcaattacga gatttggtga   5100
cgattctcct aagaaccgtg ttatttctgg taagttactc tctgtgttgc taagtgcctt   5160
gaccggtact ctatatgtgt atcagggaca agagcttggc caaatcaatt tcaagaactg   5220
gcctgttgaa aagtacgagg atgtcgaaat cagaaacaac tacaatgcaa ttaaagaaga   5280
gcatggggaa aactcagagg agatgaaaaa gttttttagaa gccattgcca ttatctccag   5340
ggaccatgct agaacaccta tgcaatggtc tcgtgaggag ccaaatgctg ttttttctgg   5400
tcctagtgct aaaccatggt tttacttgaa cgactctttc agagaaggca ttaacgtcga   5460
agatgaaatc aaggatccca actcggtttt gaacttctgg aaggaggcct tgaagtttag   5520
aaaggcgcat aaagacatta ctgtgtacgg atacgatttt gagtttattg atttagacaa   5580
taagaagttg tttagcttca caaagaagta caacaataaa acattgtttg cggccttgaa   5640
ctttagctct gatgcgacag atttcaagat tccaaatgat gattcatcgt tcaagttaga   5700
gtttggaaac tatccaaaga aggaggtaga tgcctcttcc agaacattga agccatggga   5760
aggaagaata tatatcagcg aatgacctgc aggtttgcca gcttactatc cttcttgaaa   5820
atatgcactc tatatctttt agttcttaat tgcaacacat agatttgctg tataacgaat   5880
tttatgctat ttttttaaatt tggagttcag tgataaaagt gtcacagcga atttcctcac   5940
atgtagggac cgaattgttt acaagttctc tgtaccacca tggagacatc aaaaattgaa   6000
aatctatgga agatatgga cggtagcaac aagaatatag cacgagccgg cgctagcgag   6060
ctcgtctgat atttgctaaa ttgaaatgaa ccttaccatg ccacatctat agacatcaaa   6120
accatttcca atttgtcgat atcttttgca tatcaaagta ataccaagca tgttcaaaaa   6180
gaaaagaaag cataacttta atactctatt cgaaacattc cgatccacaa cacattagtc   6240
tttttaggcc cgttgttcat cttttctatta ctttattcct aactgtattt ttataattcc   6300
```

```
gggtttataa aagattaaac taatatagcg cattcttttt gggtacaaac atacataacg      6360
gaggttt                                                                6367

<210> SEQ ID NO 16
<211> LENGTH: 2147
<212> TYPE: DNA
<213> ORGANISM: Artificial Sequence
<220> FEATURE:
<223> OTHER INFORMATION: KBpcr330

<400> SEQUENCE: 16
gtctataaaa ggcgggtttt gtcttttgcc agttgatgtt gctgagagga cttgtttgcc        60
gtttcttccg atttaacagt atagaatcaa ccactgttaa ttatacacgt tatactaaca       120
caacaaaaac aaaaacaacg acaacaacaa caacaatgaa aaacatcatt tcattagttt       180
ctaagaagaa ggctgcatcc aaaaatgaag ataaaaacat ctctgaatct tcaagagata       240
tcgttaatca acaagaggtt ttcaataccg aagatttcga ggaaggcaaa aaggactctg       300
cattcgagtt agatcacttg gagtttacta ccaactccgc acaattaggc gactctgatg       360
aggacaacga aaacgtcatt aacgaaatga acgcaacaga cgatgcaaac gaagcaaact       420
ctgaagagaa atccatgacc ttgaagcaag cattgttgaa gtatcctaaa gccgcattat       480
ggtctatttt agtctccact actttggtca tggaaggtta cgacactgct tgttatccg        540 cattatacgc tttaccagtt tttcaacgta agtttggtac attgaatggt aaaggttcct       600
atgagattac atcccaatgg cagattggtc ttaacatgtg cgtcttgtgt ggtgaaatga       660
ttggtttaca aatcaccacc tatatggttg agtttatggg taacagatac actatgatca       720
ccgctttagg tcttttgact gcttacattt tcattttgta ctattgtaag tccttagcca       780
tgattgctgt tggtcaaatt ttgtccgcca tcccttgggg ttgttttcaa tctttggctg       840
ttacctatgc ttctgaagtc tgcccattag cacttagata ctatatgact tcctattcta       900
acatttgctg gttgttcggc caaatcttcg catctggtat catgaaaaac tcacaagaga       960
acttaggcaa ttccgatctt ggttacaaac ttccatttgc tttacagtgg atttggcctg      1020
ccccacttat gattggtatt ttcttttgctc cagaatctcc ttggtggctt gttagaaaag      1080
atagagttgc agaagctaga aagtcattat ccagaatttt gtctggtaag ggcgctgaaa      1140
aggatattca agttgatctt accttaaagc agattgaatt aactattgaa aaggaaagat      1200
tattagcttc taagtctggt tcattcttta actgtttcaa gggtgttaat ggtcgtagaa      1260
ccagattagc atgtttaacc tggggttgcc aaaactcctc cggtgcagtt ttgttaggtt      1320
attctactta cttttttcgaa agagctggta tggcaacaga caaggctttc acattctcat      1380
taatccagta ctgtttgggt cttgcaggca ccttatgttc atgggttatt tcaggtagag      1440
tcggtagatg gactatcttg acttatggtc ttgcttttca aatggtctgt ttgttcatta      1500
tcggtggtat gggttttggt tctggttcct ctgcttccaa tggtgctggt ggcttattgt      1560
tggcattatc cttttttctac aatgcaggca tcggtgctgt tgtctattgt attgtcgccg      1620
aaattccttc agcagaattg agaaccaaga ctattgtttt ggctagaatc tgttacaatt      1680
tgatggccgt tatcaatgct atttttgaccc catacatgtt gaacgtttct gactggaact      1740
ggggtgctaa gacaggcttg tattggggtg gtttcactgc agttactttg gcttgggtta      1800
ttatcgactt accagaaacc actggtgtaa cattctctga aatcaatgaa ttattcaacc      1860
aaggtgttcc agctcgtaag ttcgcatcta ctgtcgtcga tccattcggt aagggtaaga      1920
```

```
cccaacatga ttccttggcc gatgaatcca tctctcaatc ttcatccatt aagcaaagag    1980
aattgaatgc agcagataag tgttaaggga tatctagtta gatagctcct cctccaatcg    2040
aattattagc tgaaactgtt ccaactttga agagattggg taaattaaga ccagattttg    2100
aaattttaat tgacggtggt gtcaaaagag gtaccgatat tttgaaa                  2147

<210> SEQ ID NO 17
<211> LENGTH: 3120
<212> TYPE: DNA
<213> ORGANISM: Artificial Sequence
<220> FEATURE:
<223> OTHER INFORMATION: KBpcr329

<400> SEQUENCE: 17
cacctactgg taatctgtaa tctatattcc cgctgaccct ttataaatga actattgtcg      60
tcaattgcgg tagtgctcca acaaattgta aggaccttct ttaacctttt cgattcaatc    120
catctccaca taaacctagt tgcacacaca gcaatttgag gaaggaatag agaaggaga     180 agcaatttct aggaaagagc aaggtgtgca acagcatgct ctgaatgata ttttcagcaa    240
tagttcagtt gaagaacctg ttggcgtatc tacatcactt cctacaaaca acaccacgaa    300
ttgcgtccgt ggtgacgcaa ctacgaatgg cattgtcaat gccaatgcca gtgcacatac    360
acgtgcaagt cccaccggtt ccctgcccgg ctatggtaga gacaagaagg acgtaccggg    420
catcgacatc aacagtttca acagcaatgc gtttggcgtc gacgcgtcga tggggctgcc    480
gtatttggat ttggacgggc tagatttcga tatggatatg gatatggata tggatatgga    540
gatgaatttg aatttagatt tgggtcttga tttggggttg gaattaaaag gggataacaa    600
tgagggtttt cctgttgatt taaacaatgg acgtgggagg tgattgattt aacctgatcc    660
aaaaggggta tgtctatttt ttagagtgtg tctttgtgtc aaattatggt agaatgtgta    720
aagtagtata aactttcctc tcaaatgacg aggtttaaaa caccccccgg gtgagccgag    780
ccgagaatgg ggcaattgtt caatgtgaaa tagaagtatc gagtgagaaa cttgggtgtt    840
ggccagccaa gggggaagga aaatggcgcg aatgctcagg tgagattgtt ttggaattgg    900
gtgaagcgag gaaatgagcg acccggaggt tgtgacttta gtggcggagg aggacggagg    960
aaaagccaag agggaagtgt atataagggg agcaatttgc caccaggata gaattggatg   1020
agttataatt ctactgtatt tattgtataa tttatttctc cttttatatc aaacacatta   1080
caaaacacac aaaacacaca acaaacacac atgaaaaata tcatttcatt ggtaagcaag   1140
aagaaggctc cctcaaaaaa tgaggataaa acatttctg agtcttcaag agatattgta   1200
aaccaacagg aggttttcaa tactgaagat tttgaagaag ggaaaaagga tagtgccttt   1260
gagctagacc acttagagtt caccaccaat tcagcccagt taggagattc tgacgaagat   1320
aacgagaatg tgattaatga gatgaacgct actgatgatg caaatgaagc taacagcgag   1380
gaaaaaagca tgactttgaa gcaggcgttg ctaaaatatc caaaagcagc cctgtggtcc   1440
atattagtgt ctactaccct ggttatggaa ggttatgata ccgcactact gagcgcactg   1500
tatgccctgc cagttttca gagaaaattc ggtactttga acggggaggg ttcttacgaa   1560
attacttccc aatggcccat tggtttaaac atgtgtgtcc aatgtggtga gatgattggt   1620
ttgcaaatca cgccttattt ggttgaattt atggggaatc gttatacgat gattacagca   1680
cttggtttgt taactgctta tgtctttatc ctctactact gtaaaagttt agctatgatt   1740
gctgtgggac aaattctctc agctatgcca tggggttgtt ccagggttt gactgttact   1800 tatgcttccg aagtttgccc tttagcatta agatattaca tgaccagtta ctccaacatt   1860
```

```
tgttggttat ttggtcaaat cttcgcctct ggtattatga aaaactcaca agagaattta      1920
gggaactctg acttgggcta taaattgcca tttgctttac aatggatttg gcctgctcct      1980
ttaatgatcg gtatcttttt cgctcctgag tcgccctggt ggttggtgag aaaggatagg      2040
gtcgctgagg caagaaaatc tttaagcaga attttgagtg gtaaaggcgc cgagaaggac      2100
attcaagttg atcttacttt aaagcagatt gaattgacta ttgaaaaaga aagactttta      2160
gcatctaaat caggatcatt ctttgattgt ttcaagggag ttaatggaag aagaacgaga      2220
cttgcatgtt taacttgggt agctcaaaat actagcggtg cctgtttact tggttactcg      2280 acatatttt ttgaaagagc aggtatggcc accgacaagg cgtttacttt ttctgtaatt      2340
cagtactgtc ttgggttagc gggtacactt tgctcctggg taatatctgg ccgtgttggt      2400
agatggacaa tactgaccta tggtcttgca tttcaaatgg tctgcttatt tattattggt      2460
ggaatgggtt ttggttctgg aagcagcgct agtaatggtg ccggtggttt attgctggct      2520
ttatcattct tttacaatgc tggtatcggt gcagttgttt actgtatcgt tgctgaaatt      2580
ccatcagcgg agttgagaac taagactata gtgctggccc gtatttgcta caatctcatg      2640
gccgttatta acgctatatt aacgcccctat atgctaaacg tgagcgattg gaactggggt      2700
gccaaaactg gtctatactg gggtggtttc acagcagtca ctttagcttg ggtcatcatc      2760
gatctgcctg agacaactgg tagaaccttc agtgaaatta atgaactttt caaccaaggg      2820
gttcctgcca gaaaatttgc atctactgtg gttgatccat tcggaaaggg aaaaactcaa      2880
catgattcgc tagctgatga gagtatcagt cagtcctcaa gcataaaaca gcgagaatta      2940
aatgcagctg ataaatgtta agggatatct agttagatag ctcctcctcc aatcgaatta      3000
ttagctgaaa ctgttccaac tttgaagaga ttgggtaaat taagaccaga ttttgaaatt      3060
ttaattgacg gtggtgtcaa aagaggtacc gatattttga aagcagtcgc aatcggtggc      3120
```

<210> SEQ ID NO 18
<211> LENGTH: 616
<212> TYPE: PRT
<213> ORGANISM: Saccharomyces cerevisiae

<400> SEQUENCE: 18

```
Met Lys Asn Ile Ile Ser Leu Val Ser Lys Lys Glu Ala Ala Ser Lys
1               5                   10                  15

Asn Glu Asp Lys Asn Ile Ser Glu Ser Ser Arg Asp Ile Val Asn Gln
                20                  25                  30

Gln Glu Val Phe Asn Thr Glu Asn Phe Glu Glu Gly Lys Lys Asp Ser
            35                  40                  45

Ala Phe Glu Leu Asp His Leu Glu Phe Thr Thr Asn Ser Ala Gln Leu
        50                  55                  60

Gly Asp Ser Asp Glu Asp Asn Glu Asn Val Ile Asn Glu Thr Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Ile Tyr Pro Lys Ala Ala Leu Trp Ser Ile Leu
                100                 105                 110

Val Ser Thr Thr Leu Val Met Glu Gly Tyr Asp Thr Ala Leu Leu Asn
            115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
```

```
            145                 150                 155                 160
Met Cys Val Gln Cys Gly Glu Met Ile Gly Leu Gln Ile Thr Pro Tyr
                165                 170                 175

Met Val Glu Phe Met Gly Asn Arg Tyr Thr Met Ile Thr Ala Leu Gly
                180                 185                 190

Leu Leu Thr Ala Tyr Val Phe Ile Leu Tyr Tyr Cys Lys Ser Leu Ala
                195                 200                 205

Met Ile Ala Val Gly Gln Val Leu Ser Ala Met Pro Trp Gly Cys Phe
    210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Gly Tyr Lys Leu Pro Phe Ala Leu Gln Trp Ile Trp Pro
                275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
                340                 345                 350

Lys Ser Gly Ser Phe Phe Asp Cys Phe Lys Gly Val Asn Gly Arg Arg
                355                 360                 365

Thr Arg Leu Ala Cys Leu Thr Trp Val Ala Gln Asn Thr Ser Gly Ala
    370                 375                 380

Cys Leu Leu Gly Tyr Ser Thr Tyr Phe Glu Arg Ala Gly Met Ala
385                 390                 395                 400

Thr Asp Lys Ala Phe Thr Phe Ser Val Ile Gln Tyr Cys Leu Gly Leu
                405                 410                 415

Ala Gly Thr Leu Cys Ser Trp Val Ile Ser Gly Arg Val Gly Arg Trp
                420                 425                 430

Thr Ile Leu Thr Tyr Gly Leu Ala Phe Gln Met Val Cys Leu Phe Ile
                435                 440                 445

Ile Gly Gly Met Gly Phe Gly Ser Gly Ser Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Thr Glu Ile Pro Ser Ala Glu Leu Arg
                485                 490                 495

Thr Lys Thr Ile Val Leu Ala Arg Ile Cys Tyr Asn Ile Met Ala Val
                500                 505                 510

Ile Asn Ala Ile Leu Thr Pro Tyr Met Leu Asn Val Ser Asp Trp Asn
                515                 520                 525

Trp Gly Ala Lys Thr Gly Leu Tyr Trp Gly Phe Thr Ala Val Thr
                530                 535                 540

Leu Ala Trp Val Ile Ile Asp Leu Pro Glu Thr Ser Gly Arg Ala Phe
545                 550                 555                 560

Ser Glu Ile Asn Glu Leu Phe Asn Gln Gly Val Pro Ala Arg Lys Phe
                565                 570                 575
```

Ala Ser Thr Val Val Asp Pro Phe Gly Lys Gly Lys Thr Arg His Asp
         580                 585                 590

Ser Leu Ala Asp Glu Ser Ile Ser Gln Ser Ser Ile Lys Gln Arg
         595                 600                 605

Glu Leu Asn Ala Ala Asp Lys Cys
         610                 615

<210> SEQ ID NO 19
<211> LENGTH: 3310
<212> TYPE: DNA
<213> ORGANISM: Artificial Sequence
<220> FEATURE:
<223> OTHER INFORMATION: pCM507 integration fragment

<400> SEQUENCE: 19

| | |
|---|---|
| cccgccatga tggttgtatt ctaccaatga gacatggccg ctgatcctgt tgtgtgggtc | 60 |
| atgggacatc acctcttggg gaggattctc ctataattgg caccgtgtat gcctcaacca | 120 |
| ctaacttcca ccctataact gaatatatta cataagcaaa tctacttttt gtttgtgttg | 180 |
| atcgccatcg ttgaaattcg cgcaacttct ggtggctcaa cgctgctgtt ctatcggtat | 240 |
| cctaagagat gtctttgccc tgagtctagg gtaaactatc caccttcgtt gctgtttgac | 300 |
| tagacagcta ctaactttac ggtagtaaat gaataacggc tcgctctcat gatcacttct | 360 |
| ctacatcacc ctaacaagtg tattattttt tttcaggtgg gtgttgctgt tggtgctagc | 420 |
| cttagtgccc tcgttaatag ttgaacaaac actggcattt ggagtataat gaaaagggat | 480 |
| cactaccccc cgcttcctgt tccgcttctc ccttccggaa aaaccaccca ccctttcttt | 540 |
| tcccccacta atgtatgaat ttttccgttc caggggaat ggcccacttg gttctctgtt | 600 |
| aacccacaca attttgacgc atcccacaca ccttttttt tttctacccc acactttccc | 660 |
| ttgaaaaatc tccaatttga actggcaatt tcacccccc accacttgca ttcattagtg | 720 |
| agtcaatcca tcccgcggtc ggagattcgg aatccaccta ctggtaatct gtaatctata | 780 |
| ttcccgctga cccttgtcga cttgctgcaa cggcaacatc aatgtccacg tttacacacc | 840 |
| tacatttata tctatattta tatttatatt tatttattta tgctacttag cttctatagt | 900 |
| tagttaatgc actcacgata ttcaaaattg acacccttca actactccct actattgtct | 960 |
| actactgtct actactcctc tttactatag ctgctcccaa taggctccac caataggctc | 1020 |
| tgtcaataca ttttgcgccg ccacctttca ggttgtgtca ctcctgaagg accatattgg | 1080 |
| gtaatcgtgc aatttctgga agagagtccg cgagaagtga ggcccccact gtaaatcctc | 1140 |
| gaggggcat ggagtatggg gcatggagga tggaggatgg gggggggag aaaataggta | 1200 |
| gcgaaaggac ccgctatcac cccacccgga gaactcgttg ccgggaagtc atatttcgac | 1260 |
| actccgggga gtctataaaa ggcgggtttc gtcttttgcc agttgatgtt gctgagagga | 1320 |
| cttgtttgcc gttcttccg atttaacagt atagaatcaa ccactgttaa ttatacacgt | 1380 |
| tatactaaca caacaaaaac aaaaacaacg acaacaacaa caacaatgtc cgcccaacac | 1440 |
| gttgaggaca ttgacaaacc aggtgttgtt atcgaagtta acccattgaa caagaacatg | 1500 |
| actgacgact ctatggctca cgaagcccaa gattttatgg acaaattttt ggacatgtct | 1560 |
| gaaaacgcta aggacaacga tagaaaggaa agtacatgc ctttaaagga aggtttaaag | 1620 |
| accttcccaa aggctgccat gtggtccgtt attttgtcta ctgccttaat catggaaggt | 1680 |
| tacgacacca atttgttaaa ttctttgtac gccttccctg atttcgctaa gaagttcggt | 1740 |
| gaatactctg aatccgacgg ttcctaccaa attccagcta aatggcaaac ttctttatcc | 1800 |

```
atgtgtgtta acgtcggtga aatcattggt ttgttcatcg ctggtatcat cgctgataga    1860
attggttaca gaaaaacttt gatcggtgcc ttgatgttga ctaccggttt catcttcatt    1920
gttttctttg ccgttaatgt tgaaatgttg ttggctggtg aattattgtt gggtttacca    1980
tggggtgcct tccaaacttt gactgtttct tacgcttctg aagtttgtcc aaccaccttg    2040
agagtctact tgaccactta tgttaacgtc tgttgggttt tcggtcaatt gatttcctct    2100
ggtatcttga gaggtttggt ttcctccgac attgaagacg tctaccgtat tccttttgcc    2160
gtccaatggg tttggccaat cccaattgcc attggtattt acttggctcc agaatctcca    2220
tggtggttgg ctagaaaaaa tagaatccaa gaagctaagc actccattaa gagattattg    2280
actgtcaacg aacacttgcc tgacaaggaa atcttggctg aggctatggt tcaaaagatc    2340
caaatgactt tgaaggaaga agctttaact aacaacggtg aatcttttt ggattgtttt    2400 aagggtcaag acttgagaag aaccagaatt gctgctattg tttgggtttc ccaaaactta    2460
actggttcct ccttgatggg ttactctacc tacttctatc aacaagctgg tttgggtcaa    2520
aacatgtcct tcactttctc tatcattcaa tactgtttcg gtatcgttgg tactttgggt    2580
tcctggttat tgtctcaaaa ggctggtaga ttcactatct acttttacgg tttgtgttct    2640
ttgttttgta tcttattcgt cgtcggttgt ttgggtatta atccaaccga atcctcttct    2700
tggggtgtcg gttctttgtt gttagtttat accttcgttt acgatttaac tatcggtcct    2760
ttgtgctact gtattgttgc tgaaattcca tccactaaat tgagaactaa aaccattatt    2820
attgctagaa acgcttacaa cattgctggt attgttgttg ctattatcac tccatacatg    2880
ttgaatccaa ccgcctggaa ctggaaggcc aagaccggtt ttttctggtc tggtttcgcc    2940
tttttcgctg ccatttggtg ttggttcgat ttgccagaaa ctaagggtaa gaccttcgcc    3000
gaattggatc aattgttcga aaacaaggtc aaggccagac aattcaagaa gactgaagtt    3060
gaagttttta atactgacga attgattgaa agattaggtg aagacggtat taaagatttg    3120
gtcgttactg acgcttctaa agatgaattt tccgaaaaag tttaattgtt ggaaatatat    3180
tattcataaa ggcgaaaaca ttccccttggt attttattcc aaatttatga tacatagacg    3240 tatttttat atataaagtt atattattaa tgattcaaga aaaagttcaa ataaactaat    3300
ggatcgggcc                                                          3310
```

<210> SEQ ID NO 20
<211> LENGTH: 579
<212> TYPE: PRT
<213> ORGANISM: Debaryomyces hansenii

<400> SEQUENCE: 20

```
Met Ser Ala Gln His Val Glu Asp Ile Asp Lys Pro Gly Val Val Ile
1               5                   10                  15

Glu Val Asn Pro Leu Asn Lys Asn Met Thr Asp Asp Ser Met Ala His
            20                  25                  30

Glu Ala Gln Asp Phe Met Asp Lys Phe Leu Asp Met Ser Glu Asn Ala
        35                  40                  45

Lys Asp Asn Asp Arg Lys Glu Lys Tyr Met Pro Leu Lys Glu Gly Leu
    50                  55                  60

Lys Thr Phe Pro Lys Ala Ala Met Trp Ser Val Ile Leu Ser Thr Ala
65                  70                  75                  80

Leu Ile Met Glu Gly Tyr Asp Thr Asn Leu Leu Asn Ser Leu Tyr Ala
                85                  90                  95
```

```
Phe Pro Asp Phe Ala Lys Lys Phe Gly Glu Tyr Ser Glu Ser Asp Gly
                100                 105                 110

Ser Tyr Gln Ile Pro Ala Lys Trp Gln Thr Ser Leu Ser Met Cys Val
            115                 120                 125

Asn Val Gly Glu Ile Ile Gly Leu Phe Ile Ala Gly Ile Ile Ala Asp
        130                 135                 140

Arg Ile Gly Tyr Arg Lys Thr Leu Ile Gly Ala Leu Met Leu Thr Thr
145                 150                 155                 160

Gly Phe Ile Phe Ile Val Phe Ala Val Asn Val Glu Met Leu Leu
                165                 170                 175

Ala Gly Glu Leu Leu Leu Gly Leu Pro Trp Gly Ala Phe Gln Thr Leu
        180                 185                 190

Thr Val Ser Tyr Ala Ser Glu Val Cys Pro Thr Thr Leu Arg Val Tyr
        195                 200                 205

Leu Thr Thr Tyr Val Asn Val Cys Trp Val Phe Gly Gln Leu Ile Ser
        210                 215                 220

Ser Gly Ile Leu Arg Gly Leu Val Ser Ser Asp Ile Glu Asp Val Tyr
225                 230                 235                 240

Arg Ile Pro Phe Ala Val Gln Trp Val Trp Pro Ile Pro Ile Ala Ile
                245                 250                 255

Gly Ile Tyr Leu Ala Pro Glu Ser Pro Trp Trp Leu Ala Arg Lys Asn
            260                 265                 270

Arg Ile Gln Glu Ala Lys His Ser Ile Lys Arg Leu Leu Thr Val Asn
            275                 280                 285

Glu His Leu Pro Asp Lys Glu Ile Leu Ala Glu Ala Met Val Gln Lys
        290                 295                 300

Ile Gln Met Thr Leu Lys Glu Glu Ala Leu Thr Asn Asn Gly Glu Ser
305                 310                 315                 320

Phe Leu Asp Cys Phe Lys Gly Gln Asp Leu Arg Arg Thr Arg Ile Ala
                325                 330                 335

Ala Ile Val Trp Val Ser Gln Asn Leu Thr Gly Ser Ser Leu Met Gly
            340                 345                 350

Tyr Ser Thr Tyr Phe Tyr Gln Gln Ala Gly Leu Gly Gln Asn Met Ser
            355                 360                 365

Phe Thr Phe Ser Ile Ile Gln Tyr Cys Phe Gly Ile Val Gly Thr Leu
    370                 375                 380

Gly Ser Trp Leu Leu Ser Gln Lys Ala Gly Arg Phe Thr Ile Tyr Phe
385                 390                 395                 400

Tyr Gly Leu Cys Ser Leu Phe Cys Ile Leu Phe Val Val Gly Cys Leu
                405                 410                 415

Gly Ile Asn Pro Thr Glu Ser Ser Ser Trp Gly Val Gly Ser Leu Leu
            420                 425                 430

Leu Val Tyr Thr Phe Val Tyr Asp Leu Thr Ile Gly Pro Leu Cys Tyr
            435                 440                 445

Cys Ile Val Ala Glu Ile Pro Ser Thr Lys Leu Arg Thr Lys Thr Ile
        450                 455                 460

Ile Ile Ala Arg Asn Ala Tyr Asn Ile Ala Gly Ile Val Val Ala Ile
465                 470                 475                 480

Ile Thr Pro Tyr Met Leu Asn Pro Thr Ala Trp Asn Trp Lys Ala Lys
                485                 490                 495

Thr Gly Phe Phe Trp Ser Gly Phe Ala Phe Ala Ala Ile Trp Cys
            500                 505                 510

Trp Phe Asp Leu Pro Glu Thr Lys Gly Lys Thr Phe Ala Glu Leu Asp
```

```
            515                 520                 525
Gln Leu Phe Glu Asn Lys Val Lys Ala Arg Gln Phe Lys Lys Thr Glu
        530                 535                 540

Val Glu Val Phe Asn Thr Asp Glu Leu Ile Glu Arg Leu Gly Glu Asp
545                 550                 555                 560

Gly Ile Lys Asp Leu Val Val Thr Asp Ala Ser Lys Asp Glu Phe Ser
                565                 570                 575

Glu Lys Val

<210> SEQ ID NO 21
<211> LENGTH: 3454
<212> TYPE: DNA
<213> ORGANISM: Artificial Sequence
<220> FEATURE:
<223> OTHER INFORMATION: pCM510 integration fragment

<400> SEQUENCE: 21
cccgccatga tggttgtatt ctaccaatga gacatggccg ctgatcctgt tgtgtgggtc     60
atgggacatc acctcttggg gaggattctc ctataattgg caccgtgtat gcctcaacca    120
ctaacttcca ccctataact gaatatatta cataagcaaa tctacttttt gtttgtgttg    180
atcgccatcg ttgaaattcg cgcaacttct ggtggctcaa cgctgctgtt ctatcggtat    240
cctaagagat gtctttgccc tgagtctagg gtaaactatc accttcgtt gctgtttgac     300 tagacagcta ctaactttac ggtagtaaat gaataacggc tcgctctcat gatcacttct    360
ctacatcacc ctaacaagtg tattattttt tttcaggtgg gtgttgctgt tggtgctagc    420
cttagtgccc tcgttaatag ttgaacaaac actggcattt ggagtataat gaaaagggat    480 cactacccc cgcttcctgt tccgcttctc ccttccggaa aaaccaccca cccttctttt    540
tcccccacta atgtatgaat ttttccgttc caggggaat ggcccacttg gttctctgtt    600
aacccacaca attttgacgc atcccacaca ccttttttt tttctacccc cactttccc     660 ttgaaaaatc tccaatttga actggcaatt ttcaccccc accacttgca ttcattagtg    720
agtcaatcca tcccgcggtc ggagattcgg aatccaccta ctggtaatct gtaatctata    780
ttcccgctga cccttgtcga cttgctgcaa cggcaacatc aatgtccacg tttacacacc    840
tacatttata tctatattta tatttatatt tatttattta tgctacttag cttctatagt    900
tagttaatgc actcacgata tcaaaattg acacccttca actactccct actattgtct    960
actactgtct actactcctc tttactatag ctgctcccaa taggctccac caataggctc   1020
tgtcaataca ttttgcgccg ccaccttca ggttgtgtca ctcctgaagg accatattgg    1080
gtaatcgtgc aatttctgga agagagtccg cgagaagtga ggcccccact gtaaatcctc    1140
gagggggcat ggagtatggg gcatggagga tggaggatgg ggggggggag aaaataggta    1200
gcgaaaggac ccgctatcac cccacccgga gaactcgttg ccgggaagtc atatttcgac    1260
actccgggga gtctataaaa ggcgggtttc gtcttttgcc agttgatgtt gctgagagga    1320
cttgtttgcc gtttcttccg atttaacagt atagaatcaa ccactgttaa ttatacacgt    1380
tatactaaca caacaaaaac aaaaacaacg acaacaacaa caacaatgaa gtccttagcc    1440
caaattgtca acagaaagaa taagaagaat ttggaagaac cagatattgt tagagctggt    1500
gtttcttctg gttccagatt atctttgaac agatctaact ttgaattaga agataccgat    1560
aagaagaagg cttccgatgc tttggaattg gaccacttgg agttcacttc tgacgtcgcc    1620
caaatcaacg aagaagaaga ccaaaacgac cacgctttgg gtgtcattaa cgccgctgat    1680
```

-continued

```
gacgctcaag aagctaatga agaggaaaaa aagatgactt tggtccaagc tttgaaggct    1740
tacccaaaag ctgctgcttg gtccgtcttg gtctctacca ccttggttat ggaaggttac    1800
gatacctcct tattgaacgc tttgttcgct ttgccagtct tccaagaaaa attcggttcc    1860
atttctaaga ccggtgaata cgaaatctct tctcaatggc aaatcggttt gaatatgtgt    1920 attttttgtcg gtgaaattat cggtttacaa atgaccggtt tcttggttga atggttcggt    1980
aacagatgga ccatgatcgg tgctttaggt ttgttgactg cttacatctt cttgttgtac    2040
ttctgtaaat cttggctat gatcgctgtt gctcaaatct gtccgctat gccatggggt    2100 tgtttccaat ctttggctgt cacctacgct tctgaagtct gtccattaac cttgagatac    2160
tatttaacca cttattctaa catgtgttgg ttgttcggtc aaattttctc cgctggtatt    2220
atgaagaact ctcaatctaa cttgggtaac tctgatttgg gttacaagat gccattcgct    2280
ttgcaatgga tctggccagc tccattggct ttgggtattt acttggctcc agaatcccca    2340
tggtacttgg ttagaaagtc caagttcgct gaagctaaga agtctttgaa cagaatcttg    2400
tctggttccg gtccacaaaa ggaaattcaa gttgatttga atttgaagca aattgaatta    2460
accatcgaaa aggaacgtaa gttgaaacaa aagaagggtt ccttctggga ctgcttcaag    2520
ggtgttgatg gtcgtagaac cagaatcacc tgtttgacct gggtctccca aaacacttcc    2580
ggttctgctt tgttgggtta ctccacctac ttcttcgaaa gagccggtat ggacacctct    2640
aacgctttca ctttctccat tatttcttac ttgttgggtt tggttggtac tatgacctcc    2700
tggatcattt ctggtagatt aggtagatgg caaatcttgg ctggtggttt gtgtttccaa    2760
atgttggtct tgtttgtcat cggtggttta ggttctcccg actccccagg tgcttctaac    2820
ggtgctggtg gtttgttgtt agccttgtct tttttctcca acgtcggtat tggttctgtc    2880
tgttactgta ttgtcgccga atgccatct gctgaattga gaactcaaac tattgttttg    2940 gctagaaaact gttacaactt gatggctatt gtcaacgcca tcttgactcc atatatgttg    3000
aacaccggtg attggaattg gggtgccaaa actggttttgt attggggtgg tatgactgcc    3060
ttgaccttgg cctgggtcat catcgacttg ccagaaaccg ctggtagaac cttctctgag    3120
attaacgaat tattcgcccg tggtgtccca gctagaaagt tcaagtccac tgttgttgac    3180
ccattcgcta aggtagaat cgccgacgac attgctgaag atgacttgga cgccgaagtt    3240
acttctgttt tcagagaaga cgacgttgaa ttgggttctg cctgtgatcc aggtaagact    3300
tctttgtaat tgttggaaat atattattca taaaggcgaa acattccct tggtatttta    3360 ttccaaattt atgatacata gacgtatttt ttatatataa agttatatta ttaatgattc    3420 aagaaaagt tcaaataaac taatggatcg ggcc                                3454
```

<210> SEQ ID NO 22
<211> LENGTH: 627
<212> TYPE: PRT
<213> ORGANISM: Torulaspora delbrueckii

<400> SEQUENCE: 22

```
Met Lys Ser Leu Ala Gln Ile Val Asn Arg Lys Asn Lys Lys Asn Leu
1               5                   10                  15

Glu Glu Pro Asp Ile Val Arg Ala Gly Val Ser Ser Gly Ser Arg Leu
            20                  25                  30

Ser Leu Asn Arg Ser Asn Phe Glu Leu Glu Asp Thr Asp Lys Lys Lys
        35                  40                  45

Ala Ser Asp Ala Leu Glu Leu Asp His Leu Glu Phe Thr Ser Asp Val
    50                  55                  60
```

```
Ala Gln Ile Asn Glu Glu Asp Gln Asn Asp His Ala Leu Gly Val
 65                  70                  75                  80

Ile Asn Ala Ala Asp Ala Gln Glu Ala Asn Glu Glu Glu Lys Lys
                 85                  90                  95

Met Thr Leu Val Gln Ala Leu Lys Ala Tyr Pro Lys Ala Ala Ala Trp
            100                 105                 110

Ser Val Leu Val Ser Thr Thr Leu Val Met Glu Gly Tyr Asp Thr Ser
            115                 120                 125

Leu Leu Asn Ala Leu Phe Ala Leu Pro Val Phe Gln Glu Lys Phe Gly
            130                 135                 140

Ser Ile Ser Lys Thr Gly Glu Tyr Glu Ile Ser Ser Gln Trp Gln Ile
145                 150                 155                 160

Gly Leu Asn Met Cys Ile Phe Val Gly Glu Ile Ile Gly Leu Gln Met
                165                 170                 175

Thr Gly Phe Leu Val Glu Trp Phe Gly Asn Arg Trp Thr Met Ile Gly
            180                 185                 190

Ala Leu Gly Leu Leu Thr Ala Tyr Ile Phe Leu Leu Tyr Phe Cys Lys
                195                 200                 205

Ser Leu Ala Met Ile Ala Val Ala Gln Ile Leu Ser Ala Met Pro Trp
210                 215                 220

Gly Cys Phe Gln Ser Leu Ala Val Thr Tyr Ala Ser Glu Val Cys Pro
225                 230                 235                 240

Leu Thr Leu Arg Tyr Tyr Leu Thr Thr Tyr Ser Asn Met Cys Trp Leu
                245                 250                 255

Phe Gly Gln Ile Phe Ser Ala Gly Ile Met Lys Asn Ser Gln Ser Asn
                260                 265                 270

Leu Gly Asn Ser Asp Leu Gly Tyr Lys Met Pro Phe Ala Leu Gln Trp
                275                 280                 285

Ile Trp Pro Ala Pro Leu Ala Leu Gly Ile Tyr Leu Ala Pro Glu Ser
            290                 295                 300

Pro Trp Tyr Leu Val Arg Lys Ser Lys Phe Ala Glu Ala Lys Lys Ser
305                 310                 315                 320

Leu Asn Arg Ile Leu Ser Gly Ser Gly Pro Gln Lys Glu Ile Gln Val
                325                 330                 335

Asp Leu Asn Leu Lys Gln Ile Glu Leu Thr Ile Glu Lys Glu Arg Lys
                340                 345                 350

Leu Lys Gln Lys Lys Gly Ser Phe Trp Asp Cys Phe Lys Gly Val Asp
                355                 360                 365

Gly Arg Arg Thr Arg Ile Thr Cys Leu Thr Trp Val Ser Gln Asn Thr
            370                 375                 380

Ser Gly Ser Ala Leu Leu Gly Tyr Ser Thr Tyr Phe Phe Glu Arg Ala
385                 390                 395                 400

Gly Met Asp Thr Ser Asn Ala Phe Thr Phe Ser Ile Ile Ser Tyr Leu
                405                 410                 415

Leu Gly Leu Val Gly Thr Met Thr Ser Trp Ile Ile Ser Gly Arg Leu
                420                 425                 430

Gly Arg Trp Gln Ile Leu Ala Gly Leu Cys Phe Gln Met Leu Val
            435                 440                 445

Leu Phe Val Ile Gly Gly Leu Gly Phe Ser Asp Ser Pro Gly Ala Ser
            450                 455                 460

Asn Gly Ala Gly Gly Leu Leu Leu Ala Leu Ser Phe Phe Ser Asn Val
465                 470                 475                 480
```

```
Gly Ile Gly Ser Val Cys Tyr Cys Ile Val Ala Glu Met Pro Ser Ala
                485                 490                 495

Glu Leu Arg Thr Gln Thr Ile Val Leu Ala Arg Asn Cys Tyr Asn Leu
            500                 505                 510

Met Ala Ile Val Asn Ala Ile Leu Thr Pro Tyr Met Leu Asn Thr Gly
        515                 520                 525

Asp Trp Asn Trp Gly Ala Lys Thr Gly Leu Tyr Trp Gly Gly Met Thr
    530                 535                 540

Ala Leu Thr Leu Ala Trp Val Ile Ile Asp Leu Pro Glu Thr Ala Gly
545                 550                 555                 560

Arg Thr Phe Ser Glu Ile Asn Glu Leu Phe Ala Arg Gly Val Pro Ala
                565                 570                 575

Arg Lys Phe Lys Ser Thr Val Val Asp Pro Phe Ala Lys Gly Arg Ile
            580                 585                 590

Ala Asp Asp Ile Ala Glu Asp Leu Asp Ala Glu Val Thr Ser Val
        595                 600                 605

Phe Arg Glu Asp Val Glu Leu Gly Ser Ala Cys Asp Pro Gly Lys
    610                 615                 620

Thr Ser Leu
625
```

<210> SEQ ID NO 23
<211> LENGTH: 3937
<212> TYPE: DNA
<213> ORGANISM: Artificial Sequence
<220> FEATURE:
<223> OTHER INFORMATION: pKB208 integration fragment
<220> FEATURE:
<221> NAME/KEY: misc_feature
<222> LOCATION: (842)..(842)
<223> OTHER INFORMATION: n is a, c, g, or t

<400> SEQUENCE: 23

```
aaaccataat gcgtgacacc gccatgatgg ttgtattcta ccaatgagac atggccgctg      60
atcctgttgt gtgggtcatg ggacatcacc tcttgggggg gattctccta taattggcac     120
cgtgtatgcc tcaaccacta acttccaccc tataactgaa tatattacat aagcaaatct     180
acttttgttt tgtgttgatc gccatcgttg aaattcgcgc aacttctggt ggctcaacgc     240
tgctgttcta tcggtatcct aagagatgtc tttgccctga gtctagggta aactatccac     300
cttcgttgct gtttgactag acagctacta actttacggt agtaaatgaa taacggctcg     360
ctctcatgat cacttctcta catcacccta acaagtgtat tatttttttt tcaggtgggt     420
gttgctgttg gtgctagcat atggataact tcgtataatg tatgctatac gaagttatgc     480
tgcaacggca acatcaatgt ccacgtttac acacctacta ttatatctat atttatattt     540
atatttattt atttatgcta cttagcttct atagttagtt aatgcactca cgatattcaa     600
aattgacacc cttcaactac tccctactat tgtctactac tgtctactac tcctctttac     660
tatagctgct cccaataggc tccaccaata ggctctgtca atacattttg cgccgccacc     720
tttcaggttg tgtcactcct gaaggaccat attgggtaat cgtgcaattt ctggaagaga     780
gtgccgcgag aagtgaggcc cccactgtaa atcctcgagg gggcatggag tatgggcat     840
gnaggatgga ggatgggggg gggggggaa ataggtagc gaaaggaccc gctatcaccc     900
caccgagaa actcgttgcc gggaagtcat atttcgacac tccggggagt ctataaaagg     960
cgggttttgt cttttgccag ttgatgttgc tgagaggact gtttgccgt tcttccgat    1020
ttaacagtat agaatcaacc actgttaatt atacacgtta tactaacaca acaaaaacaa    1080
```

```
aaacaacgac aacaacaaca acaatgtttg ctttctactt tctcaccgca tgcaccactt   1140
tgaagggtgt tttcggagtt tctccgagtt acaatggtct tggtctcacc ccacagatgg   1200
gttgggacag ctggaatacg tttgcctgcg atgtcagtga acagctactt ctagacactg   1260
ctgatagaat ttctgacttg gggctaaagg atatgggtta caagtatgtc atcctagatg   1320
actgttggtc tagcggcagg gattccgacg gtttcctcgt tgcagacaag cacaaatttc   1380
ccaacggtat gggccatgtt gcagaccacc tgcataataa cagctttctt ttcggtatgt   1440
attcgtctgc tggtgagtac acctgtgctg ggtaccctgg gtctctgggg cgtgaggaag   1500
aagatgctca attctttgca ataaccgcg ttgactactt gaagtatgat aattgttaca    1560
ataaaggtca atttggtaca ccagacgttt cttaccaccg ttacaaggcc atgtcagatg   1620
ctttgaataa aactggtagg cctatttct attctctatg taactggggt caggatttga    1680
cattttactg gggctctggt atcgccaatt cttggagaat gagcggagat attactgctg   1740
agttcacccg tccagatagc agatgtccct gtgacggtga cgaatatgat tgcaagtacg   1800
ccggtttcca ttgttctatt atgaatattc ttaacaaggc agctccaatg gggcaaaatg   1860
caggtgttgg tggttggaac gatctggaca atctagaggc cggagtcggt aatttgactg   1920
acgatgagga aaaggcccat ttctctatgt gggcaatggt aaagtcccca cttatcattg   1980
gtgccgacgt gaatcactta aaggcatctt cgtactcgat ctacagtcaa gcctctgtca   2040
tcgcaattaa tcaagatcca aagggtattc cagccacaag agtctggaga tattatgttt   2100
cagacaccga tgaatatgga caaggtgaaa ttcaaatgtg gagtggtccg cttgacaatg   2160
gtgaccaagt ggttgctttta ttgaatggag gaagcgtagc aagaccaatg aacacgacct   2220
tggaagagat tttcttttgac agcaatttgg gttcaaagga actgacatcg acttgggata   2280
tttacgactt atgggccaac agagttgaca actctacggc gtctgctatc cttgaacaga   2340
ataaggcagc caccggtatt ctctacaatg ctacagagca gtcttataaa gacggttttgt   2400 ctaagaatga tacaagactg tttggccaga aaattggtag tctttctcca aatgctatac   2460
ttaacacaac tgttccagct catggtatcg ccttctatag gttgagaccc tcggcttaag   2520
ctcaatgttg agcaaagcag gacgagaaaa aaaaaaataa tgattgttaa gaagttcatg   2580
aaaaaaaaaa ggaaaaatac tcaaatactt ataacagagt gattaaataa taaacggcag   2640
tataccctat caggtattga gatagtttta tttttgtagg tatataatct gaagcctttg   2700
aactattttc tcgtatatat catggagtat acattgcatt agcaacattg catactagtt   2760
cataacttcg tataatgtat gctatacgaa gttattaatt aaagcaattt gaggaaggaa   2820
taggagaagg agaagcaatt tctaggaaag agcaaggtgt gcaacagcat gctctgaatg   2880
atattttcag caatagttca gttgaagaac ctgttggcgt atctacatca cttcctacaa   2940
acaacaccac gaattgcgtc cgtggtgacg caactacgaa tggcattgtc aatgccaatg   3000
ccagtgcaca tacacgtgca agtcccaccg gttccctgcc cggctatggt agagacaaga   3060
aggacgatac cggcatcgac atcaacagtt tcaacagcaa tgcgtttggc gtcgacgcgt   3120
cgatggggct gccgtatttg gatttggacg ggctagattt cgatatggat atggatatgg   3180
atatggatat ggagatgaat ttgaatttag atttgggtct tgatttgggg ttggaattaa   3240 aagggggataa caatgagggt tttcctgttg atttaaacaa tggacgtggg aggtgattga   3300
tttaacctga tccaaagggg gtatgtctat tttttagagt gtgtctttgt gtcaaattat   3360
ggtagaatgt gtaaagtagt ataaactttc ctctcaaatg acgaggttta aaacacccc    3420
```

| | |
|---|---|
| cgggtgagcc gagccgagaa tggggcaatt gttcaatgtg aaatagaagt atcgagtgag | 3480 |
| aaacttgggt gttggccagc caaggggaa ggaaaatggc gcgaatgctc aggtgagatt | 3540 |
| gttttggaat tgggtgaagc gaggaaatga gcgacccgga ggttgtgact ttagtggcgg | 3600 |
| aggaggacgg aggaaaagcc aagagggaag tgtatataag gggagcaatt tgccaccagg | 3660 |
| atagaattgg atgagttata attctactgt atttattgta taatttattt ctccttttat | 3720 |
| atcaaacaca ttacaaaaca cacaaaaacac acaaacaaac acaatgaaaa atatcatttc | 3780 |
| attggtaagc aagaagaagg ctgcctcaaa aaatgaggat aaaaacattt ctgagtcttc | 3840 |
| aagagatatt gtaaaccaac aggaggtttt caatactgaa gattttgaag aagggaaaaa | 3900 |
| ggatagtgcc tttgagctag accacttaga gttcacc | 3937 |

<210> SEQ ID NO 24
<211> LENGTH: 2910
<212> TYPE: DNA
<213> ORGANISM: Artificial Sequence
<220> FEATURE:
<223> OTHER INFORMATION: pKB209 integration fragment

<400> SEQUENCE: 24

| | |
|---|---|
| ggtaagcaag aagaaggctg cctcaaaaaa tgaggataaa acatttctg agtcttcaag | 60 |
| agatattgta aaccaacagg aggttttcaa tactgaagat tttgaagaag ggaaaaagga | 120 |
| tagtgccttt gagctagacc acttagagtt caccaccaat tcagcccagt taggagattc | 180 |
| tgacgaagat aacgagaatg tgattaatga gatgaacgct actgatgatg caaatgaagc | 240 |
| taacagcgag gaaaaaagca tgactttgaa gcaggcgttg ctaaaatatc caaaagcagc | 300 |
| cctgtggtcc atattagtgt ctactaccct ggttatggaa ggttatgata ccgcactact | 360 |
| gagcgcactg tatgccctgc cagttttttca gagaaaattc ggtactttga acggggaggg | 420 |
| ttcttacgaa attacttccc aatggcccat tggtttaaac atgtgtgtcc aatgtggtga | 480 |
| gatgattggt ttgcaaatca cgccttattt ggttgaattt atggggaatc gttatacgat | 540 |
| gattacagca cttggtttgt taactgctta tgtctttatc ctctactact gtaaaagttt | 600 |
| agctatgatt gctgtgggac aaattctctc agctatgcca tggggttgtt ccagggttt | 660 |
| gactgttact tatgcttccg aagtttgccc tttagcatta agatattaca tgaccagtta | 720 |
| ctccaacatt tgttggttat ttggtcaaat cttcgcctct ggtattatga aaaactcaca | 780 |
| agagaattta gggaactctg acttgggcta taaattgcca tttgctttac aatggatttg | 840 |
| gcctgctcct ttaatgatcg gtatcttttt cgctcctgag tcgccctggt ggttggtgag | 900 |
| aaaggatagg gtcgctgagg caagaaaatc tttaagcaga attttgagtg gtaaaggcgc | 960 |
| cgagaaggac attcaagttg atcttacttt aaagcagatt gaattgacta ttgaaaaaga | 1020 |
| aagactttta gcatctaaat caggatcatt ctttgattgt tcaagggag ttaatggaag | 1080 |
| aagaacgaga cttgcatgtt taacttgggt agctcaaaat actagcggtg cctgtttact | 1140 |
| tggttactcg acatattttt ttgaaagagc aggtatggcc accgacaagg cgtttacttt | 1200 |
| ttctgtaatt cagtactgtc ttgggttagc gggtacactt tgctcctggg taatatctgg | 1260 |
| ccgtgttggt agatggacaa tactgaccta tggtcttgca tttcaaatgg tctgcttatt | 1320 |
| tattattggt ggaatgggtt ttggttctgg aagcagcgct agtaatggtg ccggtggttt | 1380 |
| attgctggct ttatcattct tttacaatgc tggtatcggt gcagttgttt actgtatcgt | 1440 |
| tgctgaaatt ccatcagcgg agttgagaac taagactata gtgctggccc gtatttgcta | 1500 |
| caatctcatg gccgttatta acgctatatt aacgccctat atgctaaacg tgagcgattg | 1560 |

-continued

```
gaactggggt gccaaaactg gtctatactg gggtggtttc acagcagtca ctttagcttg    1620
ggtcatcatc gatctgcctg agacaactgg tagaaccttc agtgaaatta atgaactttt    1680
caaccaaggg gttcctgcca gaaaatttgc atctactgtg gttgatccat tcggaaaggg    1740
aaaaactcaa catgattcgc tagctgatga gagtatcagt cagtcctcaa gcataaaaca    1800
gcgagaatta aatgcagctg ataaatgtta acctgcaggt ttgccagctt actatccttc    1860
ttgaaaatat gcactctata tcttttagtt cttaattgca acacatagat ttgctgtata    1920 acgaattttta tgctattttt taaatttgga gttcagtgat aaaagtgtca cagcgaattt    1980
cctcacatgt agggaccgaa ttgtttacaa gttctctgta ccaccatgga gacatcaaaa    2040
attgaaaatc tatggaaaga tatggacggt agcaacaaga atatagcacg agccggcgct    2100
agcgagctct aatgattcaa gaaaagttc aaataaacta atggatcaac ctatttcgac    2160
cctttcttca ttgctacttc ttccttaagc aacagatgat taagtagata ctgttttttt    2220
agccaatagt atctcgccga ggagttatac ttgactagct cttgctcaag aatcttccta    2280
agacgtacta gcctagcata gtaatctgtt tgtttctgta ttgtttgttc taactgttct    2340
acagtcattg aatcaatatc tccaatgtct tcgacgttga caactttccc cccttggca    2400 gcattctctt ttttgttgga atacgacatt aaagattcct tgattttctg ggtaccttca    2460
atgaccattg agggattaaa tttgatttct tgatttat aatggtcggc tattagctct    2520
tccacttcgt catcatgatc atcagatatg tcacgttgcc ttttcaattt attaaaattg    2580
tttatcagtt tattgtgatc ttgtatcaat tcattgcgta ctcttttctc aatatcaaaa    2640 gctatttct tcccgctaga ctcaaaatca actctgaagt catttctcg ctggaattca    2700 tgtatttcat ggattaattc tctattgata ttctcgtatg catcctgtaa actgttgccg    2760
ttgatattat gaaccgcctt taaatgtttc aataaggcat ctgctctagt aaatgccttc    2820
agacattcag gtaataaaca gtaaatggc ttctcggctg tatgcgtcct aatgtttaaa    2880
ccgtcaaaag ggcgacaccc cctaattagc                                      2910
```

<210> SEQ ID NO 25
<211> LENGTH: 617
<212> TYPE: PRT
<213> ORGANISM: SACCHAROMYCES MIKATAE

<400> SEQUENCE: 25

```
Met Lys Asn Phe Ile Ser Leu Val Asn Lys Lys Gly Thr Leu Asp
1               5                   10                  15

Asp Arg Asn Ser Ser Val Pro Glu Ser Ser Gly Ile Ile His Gln
                20                  25                  30

Arg Gly Ala Leu Asn Thr Glu Asp Phe Glu Glu Gly Lys Lys Asp Gly
            35                  40                  45

Ala Phe Glu Leu Gly His Leu Glu Phe Thr Thr Asn Ser Ala Gln Leu
        50                  55                  60

Gly Asp Ser Asp Asp Asp Asn Asp Asn Ala Ile Lys Ile Ala Asn Ala
65                  70                  75                  80

Ala Thr Asp Glu Ala Asn Glu Ala Asn Ser Glu Glu Lys Ser Met Thr
                85                  90                  95

Leu Arg Gln Ala Leu Arg Lys Tyr Pro Lys Ala Ala Leu Trp Ser Ile
            100                 105                 110

Leu Val Ser Thr Thr Leu Val Met Glu Gly Tyr Asp Thr Ala Leu Leu
        115                 120                 125
```

-continued

```
Ser Ala Leu Tyr Ala Leu Pro Val Phe Gln Arg Lys Phe Gly Thr Met
130                 135                 140

Asn Ala Glu Gly Ser Tyr Glu Ile Thr Ser Gln Trp Gln Ile Gly Leu
145                 150                 155                 160

Asn Met Cys Val Leu Cys Gly Glu Met Ile Gly Leu Gln Met Thr Thr
                165                 170                 175

Tyr Met Val Glu Phe Met Gly Asn Arg Tyr Thr Met Ile Thr Ala Leu
            180                 185                 190

Gly Leu Leu Thr Ala Tyr Ile Phe Ile Leu Tyr Tyr Cys Lys Ser Leu
        195                 200                 205

Ala Met Ile Ala Val Gly Gln Ile Leu Ser Ala Met Pro Trp Gly Cys
210                 215                 220

Phe Gln Ser Leu Ala Val Thr Tyr Ala Ser Glu Val Cys Pro Leu Ala
225                 230                 235                 240

Leu Arg Tyr Tyr Met Thr Ser Tyr Ser Asn Ile Cys Trp Leu Phe Gly
                245                 250                 255

Gln Ile Phe Ala Ser Gly Ile Met Lys Asn Ser Gln Glu Asn Leu Gly
            260                 265                 270

Asp Ser Asp Leu Gly Tyr Lys Leu Pro Phe Ala Leu Gln Trp Ile Trp
        275                 280                 285

Pro Ala Pro Leu Ile Ile Gly Ile Phe Phe Ala Pro Glu Ser Pro Trp
290                 295                 300

Trp Leu Val Arg Lys Asn Lys Ile Ala Glu Ala Lys Lys Ser Leu Asn
305                 310                 315                 320

Arg Ile Leu Ser Gly Thr Ala Ala Glu Arg Glu Ile Gln Val Asp Ile
                325                 330                 335

Thr Leu Lys Gln Ile Glu Met Thr Ile Glu Lys Glu Arg Leu Leu Ala
            340                 345                 350

Ser Lys Ser Gly Ser Phe Phe Asn Cys Phe Lys Gly Val Asp Gly Arg
        355                 360                 365

Arg Thr Arg Leu Ala Cys Leu Thr Trp Val Ala Gln Asn Ser Ser Gly
370                 375                 380

Ala Val Leu Leu Gly Tyr Ser Thr Tyr Phe Phe Glu Arg Ala Gly Met
385                 390                 395                 400

Ala Thr Asp Lys Ala Phe Thr Phe Ser Leu Ile Gln Tyr Cys Leu Gly
                405                 410                 415

Leu Ala Gly Thr Leu Cys Ser Trp Val Ile Ser Gly Arg Val Gly Arg
            420                 425                 430

Trp Ser Ile Leu Ala Tyr Gly Leu Ala Phe Gln Met Val Cys Leu Phe
        435                 440                 445

Ile Ile Gly Gly Met Gly Phe Ala Ser Gly Ser Asn Ala Ser Asn Gly
450                 455                 460

Ala Gly Gly Leu Leu Leu Ala Leu Ser Phe Phe Tyr Asn Ala Gly Ile
465                 470                 475                 480

Gly Ala Val Val Tyr Cys Ile Val Ala Glu Ile Pro Ser Ala Glu Leu
                485                 490                 495

Arg Thr Lys Thr Ile Val Met Ala Arg Ile Cys Tyr Asn Leu Met Ala
            500                 505                 510

Val Ile Asn Ala Ile Leu Thr Pro Tyr Met Leu Asn Val Ser Asp Trp
        515                 520                 525

Asn Trp Gly Ala Lys Thr Gly Leu Tyr Trp Gly Gly Phe Thr Ala Val
530                 535                 540

Thr Leu Ala Trp Val Ile Ile Asp Leu Pro Glu Thr Thr Gly Arg Thr
```

```
545                 550                 555                 560
Phe Ser Glu Ile Asn Glu Leu Phe Asn Gln Gly Val Pro Ala Arg Lys
                565                 570                 575

Phe Ala Ser Thr Val Val Asp Pro Phe Gly Lys Gly Gln Arg Gln Asn
                580                 585                 590

Asp Ser Gln Val Asp Asn Val Ile Asp Gln Ser Ser Ser Ala Met Gln
                595                 600                 605

Gln Glu Leu Asn Glu Ala Asn Glu Phe
                610                 615
```

METHOD FOR FERMENTING SUGARS USING GENETICALLY ENGINEERED YEAST

CROSS-REFERENCE TO RELATED APPLICATIONS

This application is a national phase application of International Application No. PCT/US2015/036460, filed Jun. 18, 2015, and titled "METHOD FOR FERMENTING SUGARS USING GENETICALLY ENGINEERED YEAST", which in turn claims the benefit of U.S. Provisional Application having Ser. No. 62/013,996, filed on Jun. 18, 2014, and titled "METHOD FOR FERMENTING SUGARS USING GENETICALLY ENGINEERED YEAST", both of which are incorporated herein by reference in their entireties.

The entire contents of the ASCII text file entitled N00258WO01_Sequence_Listing.txt," created on Jun. 18, 2015, and having a size of 133 kilobytes is incorporated herein by reference.

FIELD OF THE INVENTION

The present invention relates to a method for fermenting sugars, and yeasts capable of such fermentations. More particularly, the present invention relates to a method for fermenting sugars using genetically engineered yeast and such genetically modified yeasts.

BACKGROUND OF THE INVENTION

Fermentation processes are used commercially at large scale to produce organic molecules such as ethanol, citric acid and lactic acid. In those processes, a carbohydrate is fed to a organism that is capable of metabolizing it to the desired fermentation product. The carbohydrate and organism are selected together so that the organism is capable of efficiently digesting the carbohydrate to form the product that is desired in good yield. It is becoming more common to use genetically engineered organisms in these processes, in order to optimize yields and process variables, or to enable particular carbohydrates to be metabolized.

Starch is a widely available and inexpensive carbohydrate source. It is available from a wide variety of plant sources such as corn, wheat, rice, barley, and the like. Many organisms are not capable of metabolizing starch directly, or else metabolize it slowly and inefficiently. Accordingly, it is common to treat starch before feeding it into the fermentation process, in order to break it down into monosaccharides that the organism can ferment easily.

Usually, starch is hydrolyzed to form a mixture containing mainly glucose (i.e., dextrose). However, complete hydrolysis to glucose adds significant cost, so most commercially available glucose products tend to contain a small amount of various oligomeric polysaccharides. Unfortunately, many organisms cannot metabolize the oligomers, either, and so these carbohydrate values are wasted.

SUMMARY OF THE INVENTION

Isomaltose is a component that may be formed during the process of preparing starch hydrolysate raw materials having high glucose concentrations. It has been found that isomaltose is a particularly undesirable component to be present, particularly at the later stages of the present process to ferment glucose from a starch hydrolysate source to form fermentation products. While not being bound by theory, it is believed that isomaltose may interfere with the product yield not only by preventing fermentation of the two constituent glucose monomer components of the isomaltose, but also by reacting with the final fermentation products. The isomaltose may react with the fermentation products to form for example ester and other chemicals, which are formed via the reaction of a plurality of available hydroxy functionalities of the isomaltose. For example, if the product is an amino acid, the isomaltose may react with the product via the Maillard reaction to produce chemical compounds which cause browning. Thus each isomaltose compound present at the end of the fermentation process has a multiplier effect in reducing the yield and/or quality of the desired final fermentation product.

While one could add an enzyme to the starch hydrolysate to convert the isomaltose into glucose, it has been found that addition of this enzyme to a starch hydrolysate material having high glucose concentration tends to render the enzyme less effective. The present invention provides an efficient and elegant way to ferment starch hydrolysates having high glucose concentration.

It has been found that problems of inactivation of isomaltase enzymes by glucose can be addressed by using a microorganism in the fermentation process having a gene encoding transporter capable of transporting isomaltose into the microorganism, and a gene encoding an enzyme capable of converting isomaltose to glucose within the microorganism. This microorganism therefore will take up isomaltose present in the fermentation broth and convert the isomaltose to glucose by internally produced enzyme—all within the cell, where the local concentration of glucose is sufficiently low to permit effective operation of the enzyme. Likewise, isolation of the enzyme within the microorganism advantageously shields the enzyme from undesirably low pH conditions that are created when the final fermentation product is an acid.

Some yeasts natively comprise both a gene encoding a transporter capable of transporting isomaltose into the microorganism, as well as a gene encoding an enzyme capable of converting isomaltose to glucose within the microorganism (e.g. *Saccharomyces cerevisiae*). Other yeasts lack one or both genes and do not consume isomaltose (e.g. yeast of the *Issatchenkia* genus). But even for yeasts that natively comprise one or both genes, such yeasts do not typically consume isomaltose at a s sufficient rate to consume all the isomaltose present in a fermentation broth by the time that glucose is depleted. So, even for yeast that natively consumes isomaltose, the inventors have surprisingly found that it is desirable to express an exogenous gene encoding a transporter capable of transporting isomaltose into the microorganism, and/or an exogenous gene encoding an enzyme capable of converting isomaltose to glucose within the microorganism in order to improve isomaltose consumption.

In a first embodiment, a fermentation process for fermenting a starch hydrolysate containing 60-98 weight percent of glucose based on total carbohydrate and 0.3-5% weight percent of isomaltose based on total carbohydrate to a non-ethanol fermentation product is carried out. The method comprises:
  a) forming a fermentation broth containing the starch hydrolysate and a genetically modified microorganism containing
     i) an exogenous gene encoding transporter capable of transporting isomaltose into the microorganism, ii) an exogenous gene encoding an enzyme capable of converting isomaltose to glucose within the microorganism; and b) fermenting the starch hydrolysate in the fermentation broth to produce a non-ethanol fermentation product.

In a second embodiment, a batch fermentation process for fermenting a starch hydrolysate containing 60-98 weight percent of glucose based on total carbohydrate and 0.3-5% weight percent of isomaltose based on total carbohydrate to a non-ethanol fermentation product is carried out. The method comprises:

a) forming a fermentation broth containing a first portion of a total amount of the starch hydrolysate to be fermented and a genetically modified microorganism containing
  i) an exogenous gene encoding transporter capable of transporting isomaltose into the microorganism,
  ii) an exogenous gene encoding an enzyme capable of converting isomaltose to glucose within the microorganism;

b) fermenting the first portion of the starch hydrolysate in the fermentation broth in an initial fermentation step to produce a fermentation product;

c) feeding at least one additional portion of the total amount of the starch hydrolysate to be fermented containing 60-98 weight percent of glucose based on total carbohydrate and 0.3-5% weight percent of isomaltose based on total carbohydrate into the fermentation broth, wherein the fermentation broth on average has a glucose concentration of 50 g/l or less during this step (c); and d) producing a final fermentation broth containing the fermentation product.

In an embodiment, the genetically modified microorganism as described above contains an exogenous gene encoding an enzyme that catalyzes the formation of a product other than ethanol.

In some preferred aspects of the invention, one active copy of the exogenous gene encoding a transporter capable of transporting isomaltose is present in the genome of the genetically engineered microorgansim or genetically engineered yeast.

The present fermentation process is particularly beneficial for the preparation of fermentation products to be used in non-food applications. This is because the present process can be used to provide fermentation products having low amounts of undesired residual ingredients or impurities that, are permitted to be present in food products but which are not acceptable in certain non-food applications.

DETAILED DESCRIPTION OF PRESENTLY PREFERRED EMBODIMENTS

Figure 1:
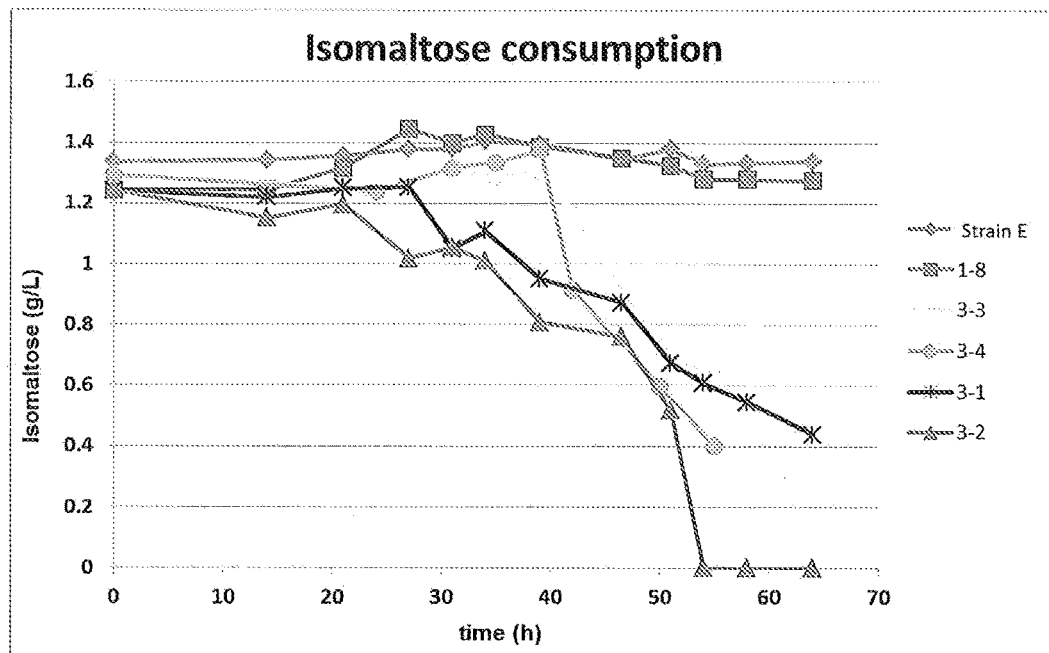
FIG. 1 is a graph showing the consumption of isomaltose during the fermentations of Example 8.

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

A fermentation broth is prepared by mixing the starch hydrolysate, water, and nutrients necessary to support growth of the fermentation organism and inoculating with a genetically modified organism suitable for carrying out the desired fermentation as described herein.

In the present fermentation process, a starch hydrolysate is used as the starting material. The starch may be obtained from any suitable starch source, such as corn, wheat, rice, barley, potatoes, cassava, and the like. The starch hydrolysates used in the present fermentation process are preferably obtained from a starch that has undergone a liquefaction and saccharification in order to obtain a high concentration of glucose. The balance of carbohydrate in such hydrolysates are composed of varying concentrations of, maltose, isomaltose, panose, and other DP3 and DP4 (i.e. oligomers of glucose) or greater glucose oligomers. Such starch hydrolysates are a particularly preferred fermentation substrate for use in this invention. In the present process, the starch hydrolysate to be used in the fermentation process contains 60-98 weight percent of glucose based on total carbohydrate and 0.3-5 weight percent of isomaltose based on total carbohydrate (for example, from 0.4-5 weight percent, from 0.5-3 weight percent, and from 0.7-2.5 weight percent isomaltose based on total carbohydrate). In another embodiments, the starch hydrolysate to be used in the fermentation process contains 80-98 weight percent of glucose based on total carbohydrate, 85-98 weight percent of glucose based on total carbohydrate or 90-97 wt % of glucose based on the total carbohydrate. In any of the above additional glucose content embodiments, the starch hydrolysate to be used in the fermentation process contains 0.3-5% weight percent of isomaltose based on total carbohydrate, or from 0.4-5 weight percent, from 0.5-3 weight percent, and from 0.7-2.5 weight percent isomaltose based on total carbohydrate. The embodiment of any of the above noted glucose content embodiments where isomaltose is present at from about 1 to about 2 percent by weight isomaltose based on the total carbohydrate is particulary notable as benefiting from the present invention. In an embodiment, at least about 90% by weight of the solids content of the starch hydrolysate is carbohydrate. In another embodiment, at least about 95% by weight of the solids content of the starch hydrolysate is carbohydrate. Typically at least about 97% by weight of solids content (for example at least about 98% by weight of solids content of the starch hydrolysate is carbohydrate) and in some instances at least 99% by weight of solids content of the starch hydrolysate is carbohydrate. In an embodiment, the starch hydrolysate is provided as a starting material composition having a dry solids content of from about 20 to about 70%. In an embodiment, the starch hydrolysate is provided as a starting material composition having a dry solids content of from about 25 to about 45%. In another embodiment, the starch hydrolysate is provided as a starting material composition having a dry solids content of from about 50 to about 70%. Starch hydrolysates having higher solids content can be easier and less expensive to ship than those which have lower solids content, which provides particular benefit for applications where the facility for carrying out the starch hydrolysis is some distance away from the facility for carrying out the fermentation process.

The starch hydrolysate used in the present fermentation process typically comprises from about 1 and 40% wt oligomers of glucose based on total carbohydrate. Preferably the starch hydrolysate used in the present fermentation process comprises from about 1 to about 30% wt oligomers of glucose, or from about 1 to about 20% wt, or from about 1 to about 10% wt, from about 1 to about 7% wt, oligomers of glucose.

The organism used in the present fermentation is one which can ferment glucose to the desired fermentation product, and is further genetically modified as described below. As such, the particular organism used is selected in relation to the fermentation product that is desired. Examples of organisms include various species of bacilli, lactobacilli, filamentous fungi, and yeast, including wild-types and mutated or recombinant types. Suitable organisms useful for producing lactic acid include wild-type bacteria from the genera *Lactobacillus, Pediococcus, Lactococcus* and *Streptococcus* and wild-type fungi of the genera *Rhizopus*. In addition, recombinant yeast strains are also suitable. Recombinant yeast strains of the genera *Kluyveromyces, Pichia, Hansenula, Candida, Trichosporon, Issatchenkia,* or *Yamadazyma* are noted as being particularly advantageous for use in the present method. In an embodiment, the above noted yeast strains are preferably modified to preferentially produce desired non-ethanol final products. In an embodiment, the above noted yeast strains comprise exogenous LDH genes to produce lactic acid. Such recombinant yeast strains are described in WO 99/14335, WO 00/71738 and WO 02/42471, for example. Additional organisms include fungi, algae and archaea. Mixtures of organisms are also specifically contemplated.

In an embodiment, the genetically modified microorganism is yeast. In an embodiment, the genetically modified microorganism is a crabtree negative yeast. In an embodiment, the genetically modified microorganism is a yeast of the genus *Kluyveromyces* or *Issatchenkia*. In an embodiment, the genetically modified microorganism is a yeast of the *I. orientalis/P. fermentans* clade.

The *I. orientalis/P. fermentans* clade is the most terminal clade that contains at least the species *I. orientalis, Pichia galeiformis, Pichia* sp. YB-4149 (NRRL designation), *Candida ethanolica, Pichia deserticola, P. membranifaciens,* and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," *Antonie van Leeuwenhoek* 73:331-371, 1998, incorporated herein by reference (see especially p. 349). Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods.

In certain embodiments, the genetically modified yeast cells provided herein belong to the genus *Issatchenkia*, and in certain of these embodiments the yeast cells are *I. orientalis*. When first characterized, the species *I. orientalis* was assigned the name *Pichia kudriavzevii*. The anamorph (asexual form) of *I. orientalis* is known as *C. krusei*. Numerous additional synonyms for the species *I. orientalis* have been listed elsewhere (Kurtzman and Fell, The Yeasts, a Taxonomic Study. Section 35. *Issatchenkia Kudryavtsev*, pp 222-223 (1998)).

Specifically, the organism used in the present fermentation is a genetically modified microorganism containing
  i) a gene encoding transporter capable of transporting isomaltose, and
  ii) a gene encoding an enzyme capable of converting isomaltose to glucose.

In an embodiment of the present invention, a cell has an isomaltose transport capacity as determined by the TRANSPORTER CAPABILITY EVALUATION as set forth in the Examples of at least about 0.05 mmol isomaltose/[g cell dry weight*min]. In embodiments, the cell has an isomaltose transport capacity of at least about 0.1, and preferably at least about 0.2, 0.3, 0.4, 0.5, 0.75, or 1.0 [g cell dry weight*min].

In an embodiment of the present invention, a cell has an isomaltose to glucose conversion capacity as determined by the ISOMALTOSE TO GLUCOSE CONVERSION EVALUATION as set forth in the Examples of at least about 0.05 (micromole glucose released/[mg protein*min]). In embodiments, the cell has an isomaltose to glucose conversion capacity at least about 0.1, 0.3, 0.5, 0.7, 0.9, 1.0, 3.0, 5.0, or 7.0.

All combinations of the above disclosed levels of isomaltose transport capacity and glucose conversion capacity are expressly contemplated.

In an embodiment, the genetically modified microorganism contains an exogenous gene encoding transporter capable of transporting isomaltose and an exogenous gene encoding an enzyme capable of converting isomaltose to glucose.

"Endogenous" as used herein with regard to genetic components such as genes, promoters, and terminator sequences means that the genetic component is present at a particular location in the genome of a native form of a particular microorganism cell.

"Exogenous" as used herein with regard to genetic components means that the genetic component is not present at a particular location in the genome of a native form of a particular microorganism cell. The exogenous genetic component may be sourced from the same species as the subject microorganism, or from a different species. An exogenous genetic component may have either a native or non-native sequence. An exogenous genetic component with a native sequence comprises a sequence identical to (apart from individual-to-individual mutations which do not affect function) a genetic component that is present in the genome of a native cell (i.e., the exogenous genetic component is identical to an endogenous genetic component). However, the exogenous component is present at a different location in the host cell genome than the endogenous component. For example, an exogenous isomaltase (IMA) gene that is identical to an endogenous IMA gene may be inserted into a microorganism cell, resulting in a modified cell with a non-native (increased) number of IMA gene copies. Similarly, an exogenous PDC promoter that is identical to an endogenous PDC promoter can be inserted into a microorganism cell such that it is operatively linked to an exogenous gene such as an IMA gene, which has an identical sequence with a native IMA gene, resulting in altered expression of the native gene. An exogenous genetic component with a non-native sequence comprises a sequence that is not found in the genome of a native cell.

In an embodiment, the genetically modified microorganism contains a heterologous gene encoding transporter capable of transporting isomaltose and a heterologous gene encoding an enzyme capable of converting isomaltose to glucose. For purposes of the present invention, "heterologous" as used herein with regard to genetic components means that the genetic component is not present at a particular location in the genome of a native form of a particular microorganism cell, and which is sourced from a different species. As with the exogenous genetic component discussed above, a heterologous genetic component will have non-native sequence. For example, an exogenous IMA gene from a particular species may be inserted into a yeast cell of another species. Similarly, an exogenous PDC promoter from a particular species may be inserted into a yeast cell of another species.

In the case of either of the exogenous gene or the heterologous gene, the gene is preferably integrated into the host cell genome in a functional manner, meaning that it is capable of producing an active protein in the host cell. However, in certain embodiments the gene may be introduced into the cell as part of a vector that is stably maintained in the host cytoplasm.

A transporter is a protein that resides in a biological membrane, facilitating the movement of substances such as amino acids, sugars, and nucleotides from one side of the cell to the other. In yeast, the disaccharide isomaltose is transported across the membrane by a specific type of transporter, a proton symporter. These transporters are H(+) symports that depend on the electrochemical proton gradient. The S. cerevisiae MAL11 is a high affinity maltose proton symporter (alpha-glucoside), capable of transporting a broad range of substrates that includes maltotriose, palatinose, trehalose, melezitose, and isomaltose.

Preferably the exogenous maltose/isomaltose transporter gene encodes for a polypeptide with an amino acid sequence having greater than 80, 85, 90, 95 98, or 99% sequence identity with the amino acid sequence of any of the following: SEQ ID NO: 7, SEQ ID NO: 18, SEQ ID NO: 20, SEQ ID NO: 22, or SEQ ID NO: 25.

More preferably the maltose/isomaltose transporter has greater than 85 90, 95, 98, or 99% identity with the amino acid sequence of SEQ ID NO: 18 or SEQ ID NO: 25, and in some instances, most preferably SEQ ID NO: 18.

A maltose/isomaltose transporter gene having sequence identity (e.g., greater than 80%) with one of SEQ ID NO: 7, SEQ ID NO: 18, SEQ ID NO: 20, SEQ ID NO: 22 or SEQ ID NO: 25 may be referred to as an "ortholog" of the referenced maltose/isomaltose transporter. "Orthologs" generally refer to those genes related by vertical descent and provide the same or identical cellular function(s) in different organisms. Orthologs share sequence similarity in an amount indicating they are homologous, or related by evolution from a common ancestor. Orthologs may share three-dimensional structure similarity, although not sequence similarity, of a significant amount to indicate evolution from a common ancestor.

Aspects of the disclosure also contemplate variant maltose/isomaltose transporters, for example, those having one or more amino acid substitutions that are non-natural. Preferably, the amino sequence of the maltose/isomaltose transporter has one of more of the following substitutions relative to SEQ ID NO: 7.

(a) D118N
(b) M232T
(c) K3041
(d) S382N
(e) L490Q
(f) T523P
(g) I590V
(h) I643V
(i) I655M
(j) S676G
(k) A682T
(l) N1075D
(m) S1141T
(n) V1153C
(o) L1225V
(p) S1375G
(q) A1462T
(r) L15251
(s) T1666S
(t) T1675A
(u) Q1768R

One of more of the previous substitutions may also be made in orthologs of SEQ ID NO: 7. Genes sharing a desired amount of identify (e.g., greater than 80%) to the maltose/isomaltose transporter of SEQ ID NO: 7 can be determined by methods well known to those skilled in the art. For example, inspection of nucleic acid or amino acid sequences for two polypeptides will reveal sequence identity and similarities between the compared sequences. Sequence alignment and generation of sequence identity include global alignments and local alignments which can be carried out using computational approaches. An alignment can be performed using BLAST (National Center for Biological Information (NCBI) Basic Local Alignment Search Tool) version 2.2.29 software with default parameters. A sequence having an identity score of XX % (for example, 80%) with regard to a reference sequence using the BLAST version 2.2.29 algorithm with default parameters is considered to be at least XX % identical or, equivalently, have XX % sequence identity to the reference sequence. A global alignment can be used to align sequences with significant identity to SEQ ID NO: 7 template in order to determine which corresponding amino acid position(s) in the target sequence (e.g., maltose/isomaltose transporter ortholog) can be substituted with the one or more of the amino acid changes of (a)-(u).

In some embodiments of the invention, the organism may contain an increased copy number of the gene encoding a maltose/isomaltose transporter. In some embodiments, the organism may contain 2 or more copies of a maltose/isomaltose transporter. In some embodiments, the organism may contain 4 or more copies of a maltose/isomaltose transporter. In some embodiments, the organism may contain 6 or more copies of a maltose/isomaltose transporter.

In some embodiments of the invention, the microorganism has been subjected to mutagenesis on selection in the presence of 2-Deoxy-D-glucose (2-DG). In some embodiments of the invention, the microorganism has been subjected to mutagenesis on selection in the presence of 2-Deoxy-D-glucose (2-DG) and isomaltose. In some embodiments of the invention, the microorganism has been subjected to mutagenesis on selection in the presence of 2-Deoxy-D-glucose (2-DG) and maltose.

The enzyme capable of converting isomaltose to glucose as produced by the microorganism is any enzyme effective for hydrolyzing the 1,6 ether linkage in isomaltose. A preferred enzyme for acting on isomers having 1,6 linkages is isomaltase. An isomaltase may also exhibit cross activity for hydrolyzing the 1,4 ether linkages in maltose.

In an embodiment, the enzyme produced by the microorganism is effective for conversion of both isomaltose and maltose into glucose. It has surprisingly been discovered that an isomaltase that is not particularly effective for hydrolyzing the 1,4 ether linkage in maltose when present in the fermentation broth at large is effective for hydrolyzing the 1,4 ether linkage when present inside the microorganism.

In another embodiment, the microorganism is provided with a gene encoding an additional enzyme capable of converting maltose to glucose that is different from the isomaltase enzyme. The enzyme may be any enzyme that is more effective for hydrolyzing isomers such as maltose having a 1,4 ether linkage. A preferred enzyme for acting on isomers having 1,4 linkages is maltase. Optionally, the same or different enzymes may be produced by the microorganism to covert other oligomeric polysaccharides that may be present in the starch hydrolysate into glucose. A maltase may also exhibit cross activity for hydrolyzing the 1,6 ether linkages in isomaltose.

Preferably the exogenous isomaltase gene encodes for a polypeptide having greater than 80, 85, 90, 95, 98 or 99% sequence identity with the amino acid sequence of SEQ ID NO: 9.

In an embodiment, the genetically modified microorganism is a yeast having a deletion or disruption in a gene encoding for a pyruvate decarboxylase (i.e. a PDC deletion), thereby eliminating ethanol production.

In an embodiment, the microorganism is a yeast that produces an organic acid fermentation product wherein the mass yield of organic acid on carbohydrate is greater than 0.1 g/g, or greater than 0.2 g/g, or greater than 0.3 g/g.

In an embodiment, the initial glucose concentration is from about 50 g/L to about 170 g/L. In an embodiment, the initial glucose concentration is from about 70 g/L to about 140 g/L. In an embodiment, the initial glucose concentration is from about 80 g/L to about 130 g/L. In an embodiment, the initial glucose concentration is from about 90 g/L to about 120 g/L.

Embodiments using a higher initial concentration of glucose in the fermentation broth are particularly advantageous, because one may take advantage of the better economics that come with using higher starting concentrations of starting materials.

The fermentation broth will also include water and preferably includes nutrients, such as proteins (or other nitrogen source), vitamins and salts, which are necessary or desirable for cell function. Other components may also be present in the fermentation broth, such as buffering agents, fermentation products (which tend to accumulate as the fermentation progresses), and other metabolites. In cases where the fermentation is an acid, it is common to buffer the broth with a base such as calcium hydroxide or calcium carbonate, ammonia or ammonium hydroxide, sodium hydroxide, or potassium hydroxide in order to maintain a pH at which the organism functions well.

The fermentation is carried out under conditions so that fermentation can occur. Although conditions can vary depending on the particular organism and desired fermentation product, typical conditions include a temperature of from about 20° C., preferably from about 30° C. to about 50° C., more preferably about 45° C. Usually the reaction mixture is mixed. The mixing may occur by sparging gas to the fermentation broth or alternatively via direct mechanical agitation or by other means.

Preferably, the fermentation is carried out in industrial compacity fermenters in order to achieve commercial scale economic benefits and control. In an embodiment, the fermentation is carried out in a fermenter that has a capacity of about 10,000 liters or more.

In an embodiment, the fermentation is carried out such that the oxygen uptake rate is from about 1 to about 35 mmol $O_2/(L*h)$. In an embodiment, the oxygen uptake rate is from about 5 to about 30 mmol $O2/(L*h)$, or from about 7 to about 25 mmol $O2/(L*h)$, or from about 9 to about 18 mmol $O2/(L*h)$.

As noted above, the present fermentation process using genetically modified microorganisms advantageously features generation of the enzymes capable of converting isomaltose (and optionally, other oligomeric polysaccharide(s)) into glucose within the microorganism. These enzymes therefore are not directly exposed to the broth conditions, but rather experience only the concentration conditions within the microorganism.

The effectiveness of these enzymes is often is at least partially dependent on the pH and composition (including cation composition) of the medium in which it is located. Isolation of the enzymes within the microorganism advantageously shields the enzyme both from excess glucose concentration and undesirably low pH conditions during active fermentation (i.e. while the microorganism is producing the desired fermentation product) that are created when the final fermentation product is an acid.

If one were to use an externally added enzyme, it would be necessary to adjust the pH of the fermentation broth to enhance the activity of the enzyme. The adjustment of the pH normally includes addition of a basic compound to the fermentation broth, which then must be removed, often generating byproducts such as gypsum that must be disposed. The present process therefore substantially reduces or eliminates generation of undesired side products through addition of compensating chemistries, as compared to processes using direct addition of enzyme.

In an embodiment of the present invention, the fermentation broth has a pH of less than 4.8 at some point in the active fermentation process. In other embodiments, the fermentation broth has a pH of less than 4.5, or 4, or 3.5 at some point in the active fermentation process.

In an embodiment of the present invention, the fermentation is carried out as a single batch until completion.

In another embodiment of the present invention, the fermentation is carried out as a fed batch fermentation process, whereby a first portion of a total amount of the starch hydrolysate to be fermented is fermented to a desired glucose content that is lower than the glucose content prior to fermentation, and then additional starch hydrolysate is added in one or more portions to provide glucose to be fermented, but at a concentration that is within a desired range to provide efficient fermentation with less interference in generation of final fermentation product due to the presence of undesired impurities.

It has been found that maintenance of the glucose concentration at a relatively lower level in the fermentation process after an initial fermentation stage is advantageous to efficient production of the desired final product, and in particular control of undesired isomaltose components and optionally other components, such as maltose.

The first portion of the total amount of the starch hydrolysate to be fermented preferably has a glucose concentration of less than 100 g/L or less than 90 g/L. In embodiments, the initial glucose concentration has a glucose concentration less than 100 g/L and greater than 40 g/L, or greater than 50 g/L, greater than 60 g/L, greater than 70 g/L, or greater than 80 g/L. In embodiments, the initial glucose concentration has a glucose concentration less than 90 g/L and greater than 40 g/L, or greater than 50 g/L, greater than 60 g/L, greater than 70 g/L, or greater than 80 g/L.

In an embodiment, the starch hydrolysate is fermented in the fermentation broth in an initial fermentation step to produce a fermentation product until the fermentation broth contains about 30 g/L or less of glucose. In an embodiment, the starch hydrolysate is fermented until the fermentation broth contains about 25 g/L or less of glucose in the initial fermentation step. In an embodiment, the starch hydrolysate is fermented until the fermentation broth contains about 20 g/L or less of glucose. In an embodiment, the starch hydrolysate is fermented until the fermentation broth contains about 15 g/L or less of glucose. In embodiments, the starch hydrolysate is fermented in the initial fermentation step until the fermentation broth contains from about 0.1 g/L to about 20 g/L of glucose, or from about 0.1 g/L to about 15 g/L of glucose, or from about 2 g/L to about 15 g/L of glucose, or from about 2 g/L to about 10 g/L of glucose.

In some embodiments, a minimum amount of glucose is desirable in the system to assure that the fermentation process can continue to operate without interruption during the fermentation process. Thus, in some embodiments, the starch hydrolysate is fermented in the initial fermentation step until the fermentation broth contains from about 30 g/L to about 5 g/L of glucose, or from about 25 g/L to about 5 g/L of glucose, or from about 20 g/L to about 5 g/L of glucose, or from about 15 g/L to about 5 g/L of glucose. Similarly, in some embodiments, the starch hydrolysate is fermented until the fermentation broth contains from about 30 g/L to about 8 g/L of glucose, or from about 25 g/L to about 8 g/L of glucose, or from about 20 g/L to about 8 g/L of glucose, or from about 15 g/L to about 8 g/L of glucose. Similarly, in some embodiments, the starch hydrolysate is fermented until the fermentation broth contains from about 30 g/L to about 10 g/L of glucose, or from about 25 g/L to about 10 g/L of glucose, or from about 20 g/L to about 10 g/L of glucose, or from about 15 g/L to about 10 g/L of glucose.

Additional starch hydrolysate is added in one or more additional portions to the fermentation batch to continue to produce the desired final fermentation product. In an embodiment of the present invention, the remaining portion of the total amount of starch hydrolysate is added in at least two additional portions.

The starch hydrolysate is preferably added in a manner such that the concentration of glucose in the fermentation broth during these addition steps of the fermentation is 30 g/L or less of glucose. In an embodiment, the concentration of glucose in the fermentation broth is about 25 g/L or less of glucose. In an embodiment, the concentration of glucose in the fermentation broth is about 20 g/L or less of glucose. In an embodiment, the concentration of glucose in the fermentation broth is about 15 g/L or less of glucose. In embodiments, the concentration of glucose in the fermentation broth is from about 0.1 g/L to about 20 g/L of glucose, or from about 0.1 g/L to about 15 g/L of glucose, or from about 2 g/L to about 15 g/L of glucose, or from about 2 g/L to about 10 g/L of glucose.

In some embodiments, a minimum amount of glucose is desirable in the system to assure that the fermentation process can continue to operate without interruption during the fermentation process. Thus, in some embodiments, the concentration of glucose in the fermentation broth is from about 30 g/L to about 5 g/L of glucose, or from about 25 g/L to about 5 g/L of glucose, or from about 20 g/L to about 5 g/L of glucose, or from about 15 g/L to about 5 g/L of glucose. Similarly, in some embodiments, the concentration of glucose in the fermentation broth is from about 30 g/L to about 8 g/L of glucose, or from about 25 g/L to about 8 g/L of glucose, or from about 20 g/L to about 8 g/L of glucose, or from about 15 g/L to about 8 g/L of glucose. Similarly, in some embodiments, the concentration of glucose in the fermentation broth is from about 30 g/L to about 10 g/L of glucose, or from about 25 g/L to about 10 g/L of glucose, or from about 20 g/L to about 10 g/L of glucose, or from about 15 g/L to about 10 g/L of glucose.

In a preferred embodiment of the present invention, the remaining portion of the total amount of starch hydrolysate is added to the fermentation broth using a variable rate addition system. This system is preferred because it does not introduce temporarily high concentrations of glucose in the fermentation batch that would adversely affect the activity of the enzyme. Examples of such systems include a variable speed pump or a metering valve (such as a throttle valve) operably connected to a pump, which pump or valve can be utilized to vary the amount of hydrolysate introduced into the fermentation broth over time. In an embodiment, the starch hydrolysate addition is carried out over a time period of from about 4 to about 30 hours, for example from about 5 to about 24 hours, and in some cases to optimize product yield, enzyme usage and production costs, from about 10 to about 20 hours.

In an embodiment, during the addition of the remaining portion of the starch hydrolysate the glucose concentration is monitored by a real-time monitoring system. Real-time monitoring systems include systems that directly monitor glucose concentration and systems that indirectly monitor glucose concentration. Examples of real-time monitoring systems that typically directly monitor glucose concentration include systems based on infrared (IR) spectroscopy, near-infrared (NIR) spectroscopy systems, Fourier transform infrared (FTIR) systems, systems based on refractive index, automated enzyme based measurement systems such as a YSI 2950 Biochemistry Analyzer sold by YSI Life Sciences systems, high performance liquid chromatography (HPLC) based systems, gas chromatography (GC) based systems, and other real-time monitorying systems known to one of skill in the art. Additionally real-time monitoring systems that indirectly monitor/measure the glucose concentration of a fermentation process can be developed by determining the typical carbon distribution in a particular fermentation process and correlating the glucose concentration present in the fermentation broth to another parameter exhibited by the fermentation, such as, for example, a correlation of the glucose level present in the fermentation broth with a measurement of the carbon dioxide evolution rate and the amount of carbon dioxide present in an off-gas stream from the fermentation vessel. The carbon dioxide can be readily measured through use of a mass spectrometer or other suitable instrumental technique for measuring the components of the off-gas stream. In a preferred embodiment, the glucose concentration is monitored by a real-time monitoring system using infrared spectroscopy. In another preferred embodiment, the glucose concentration is monitored by a real-time monitoring system using near-infrared spectroscopy. In a particularly preferred aspect of the invention, the real time monitoring systems interface with equipment that controls the introduction of starch hydrolysate introduced into the fermentation broth to facilitate the maintenance of the glucose concentration in the fermentation broth at the desired concentration.

In another aspect of the invention, the glucose concentration is monitored by real-time monitoring system, and a control system utilizes the value of glucose concentration measured to control the introduction of starch hydrolysate (and optionally enzyme) into the fermentation broth. In this aspect of the invention, the starch hydrolysate utilized has greater than 60 percent by weight glucose concentration based on the total carbohydrate, typically greater than 70 percent by weight glucose concentration, for example, greater than 80 percent by weight glucose concentration based on the total carbohydrate and in many instances greater than 90 percent by weight glucose concentration based on the total carbohydrate.

The addition of the remaining portion of the starch hydrolysate is continued until the desired amount of starch hydrolysate has been added. After the desired amount of starch hydrolysate has been added, the fermentation is typically allowed to proceed until the final fermentation broth is produced. In a preferred embodiment, after the desired amount of starch hydrolysate has been added, the fermentation is allowed to proceed until the glucose concentration is at a concentration below 5 g/L, or preferably below 1 g/L, or more preferably below 0.5 g/L based on the volume of the final fermentation broth.

In an embodiment, at least thirty percent of the isomaltose introduced into the fermentation over the entire fermentation process is converted to other materials during the fermentation.

In an embodiment, the final fermentation broth comprises no more than about 3 g/L of isomaltose. In an embodiment, the final fermentation broth comprises no more than about 1.5 g/L or 1 g/L of isomaltose, and preferably no more than about 0.5 g/L isomaltose. In an embodiment, the final fermentation broth comprises no more than about 3 g/L or 1 g/L of glucose and preferably no more than about 0.5 g/L glucose.

In an embodiment, the final fermentation broth comprises no more than 3 g/L each of trimer and tetramer oligomers of glucose (i.e. DP3 and DP4 oligomers of glucose), and preferably no more than 1.5 g/L or 1 g/L each of DP3 and DP4 oligomers of glucose, and preferably no more than 0.5 g/L each of DP3 and DP4 oligomers of glucose (for example less than 0.3 g/L each of DP3 and DP4 oligomers of glucose, and in some instances less than 0.2 g/L each of DP3 and DP4 oligomers of glucose).

The fermentation product may be any product that can be prepared by fermenting glucose. In an embodiment, the fermentation product is selected from the group consisting of: amino acids, organic acids, alcohols, diols, polyols, fatty acids, fatty acid alkyl esters (such as fatty acid methyl or ethyl esters (for example C6 to C12 fatty acid methyl esters (preferably C8 to C10 fatty acid methyl esters))), monoacyl glycerides, diacyl glycerides, triacyl glycerides, and mixtures thereof. Preferred fermentation products are organic acids, amino acids, fatty acid alkyl esters (such as fatty acid methyl esters (for example C8 to C12 fatty acid methyl esters (preferably C8 to C10 fatty acid methyl esters))), and their salts thereof, and especially where the organic acid is selected from the group consisting of hydroxyl carboxylic acids (including mono-hydroxy and di-hydroxy mono-, di-, and tricarboxylic acids), monocarboxylic acids, dicarboxylic acids, and tricarboxylic acids and mixtures thereof. Examples of fermentation products that are prepared by the present process are organic acids or amino acids such as lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, acetic acid, methyl hexanoate, methyl octanoate, methyl nonanoate, methyl decanoate, methyl dodecanoate, ethyl hexanoate, ethyl octanoate, ethyl nonanoate, ethyl decanoate, ethyl dodecanoate, and mixtures thereof and derivatives thereof and salts thereof.

Optionally, additional control of undesired presence of isomaltose may be obtained by adding an effective amount of at least one active enzyme that converts isomaltose into glucose to the fermentation broth.

The enzyme may be any enzyme effective for hydrolyzing isomers having a 1,6 ether linkage. A preferred enzyme for acting on isomers having 1,6 linkages is trans-glucosidase.

The amount of enzyme to be used depends somewhat on the particular enzyme, the desired rate of reaction, and presence of any other oligomeric polysaccharide(s) that may also be effectively hydrolyzed by the enzyme. Enzyme activity is commonly measured in Units (U) of activity. One unit of enzyme activity is defined as the amount of enzyme activity that will convert one micro-mole of substrate per minute. In an embodiment, the enzyme is used in a quantity sufficient to provide about 0.05-5 Units of enzyme activity for an isomaltose substrate per liter of fermentation broth. In another embodiment, the quantity of enzyme is from about 0.1-3 Units of enzyme activity per liter of fermentation broth, In another embodiment, the quantity of enzyme is from about about 0.3-1 Units of enzyme activity per liter of fermentation broth Similarly, these Units of enzyme activity per liter of fermentation broth may be used to determine the amount of enzyme suitable for conversion of other oligomeric polysaccharide(s) that may be present in the fermentation broth. The above number of Units is used to provide a good approximation of the amount of enzyme to be added to the fermentation broth, which is evaluated by experimental observation to determine actual amounts of enzyme required under conditions of use (e.g. temperature, pH and other conditions particular to a given fermentation process) to achieve the desired concentrations of residual oligosaccharides in the final fermentation broth at the lowest cost of enzymes.

In an embodiment, the additional active enzyme is added to the fermentation broth in a single addition step. In an embodiment, the active enzyme is added to the fermentation broth in a single addition step metered over a time of from about 3 minutes to 3 hours. In an embodiment, the active enzyme is added to the fermentation broth in a plurality of addition steps after the initial fermentation step. In another embodiment, at least a portion of the enzyme is added after the remaining portion of the starch hydrolysate is fed, and the amount of isomaltose present in the fermentation broth is monitored and additional enzyme is added as needed to achieve the desired isomaltose level.

Addition of the enzyme after the initial fermentation step, once the desired glucose concentration level is achieved (typically less than 50 g/L glucose, preferably less than 40 g/L glucose, and in some embodiments less than 30 g/L glucose, for example less than 20 g/L glucose), maximizes its effectiveness, because it has been found that high glucose concentration compositions tend to experience reverse conversion of glucose to isomaltose and additionally that the enzyme itself is inhibited by high concentration of glucose. Further, the enzyme has a finite time of effectiveness, and so later addition to the fermentation process is advantageous to use the enzyme during its active lifetime. Preferably, after the additional enzyme is added, the glucose concentration is maintained below 30 g/L as described earlier.

In an embodiment, the total amount of starch hydrolysate additionally contains from about 1 to about 10 weight percent of maltose. This maltose preferably also is enzymatically converted into glucose. In an embodiment, the enzyme selected for addition is effective for conversion of both isomaltose and maltose into glucose. In another embodiment, an additional enzyme that is different from the isomaltose enzyme may also be introduced to convert maltose into glucose. The enzyme may be any enzyme that is more effective for hydrolyzing isomers such as maltose having a 1,4 ether linkage. A preferred enzyme for acting on isomers having 1,4 linkages is glucoamylase. Optionally, the same or different enzymes may be introduced to covert other oligomeric polysaccharides that may be present in the starch hydrolysate into glucose.

It has been surprisingly discovered that the microorganism of the invention reduces the concentration of isomaltose so effectively that in one aspect the only additional enzyme that is added to the fermentation is an enzyme that is more effective for hydrolyzing DP3 and DP4 oligomers of glucose having 1,4 ether linkages to glucose. A preferred enzyme for this aspect comprises a glucoamylase. This enzyme preferably is added in a similar manner as described for the transglucosidase above (i.e. added after the glucose concentration is reduced to less than 50 g/L, etc).

In the embodiment where enzyme capable of converting isomaltose and other oligomeric polysaccharide(s) into glucose (such as transglucosidase (TG)) is added to the fermentation broth, the activity of these enzymes often is at least partially dependent on the pH and composition (including cation composition) of the fermentation broth being utilized. When the fermentation products comprise a carboxylic acid (including hydroxy carboxylic acid(s) and amino acids), it may be desirable to adjust the pH of the fermentation broth to enhance the activity of the enzyme. When desired, a basic compound typically would be added to the fermentation broth to adjust the pH of the broth and therefore enhance the activity of an enzyme, such as a TG enzyme. Basic compounds that may be utilized include compounds having the following cations: ammonium, sodium, potassium, and mixtures thereof.

When the fermentation process utilizes a gypsum recovery process, as described below, the preferred cation utilized comprises calcium. In a gypsum recovery process, an organic acid fermentation product (including a hydroxy carboxylic acid) is made. During the fermentation, the pH of the fermentation broth is maintained at a desirable level using calcium hydroxide, often used in the form of lime. Once the fermentation is complete, it is desirable to enhance the recovery of the organic acid by adding sulfuric acid to acidulate the broth and thereby increase the percentage of acid that is recovered from the broth. The ions from the lime and sulfuric acid react to form calcium sulfate (gypsum), which can then be readily removed from the fermentation broth by precipitation.

Alternatively, ammonia or ammonium hydroxide is economical and abundant. Ammonium hydroxide has the advantage of providing not only pH buffering, but also supplies an additional bio-available nitrogen source to the fermentation. Examples of fermentations that employ ammonium hydroxide for pH control include fermentation processes for the manufacture of citric acid, lysine or other amino acids. Additionally, ammonium hydroxide is commonly employed in fermentation processes that typically incorporate the ammonium into the fermentation product (such as amino acids) or biomass (such as amino acids or citric acid and other processes known to one of skill in the art), can tolerate ammonium in the final product specifications or processes where the fermentation product is typically recovered through the use of ion exchange, crystallization or liquid-liquid extraction (such as citric acid, succinic acid, or fumaric acid, and other processes known to one of skill art).

Sodium hydroxide and potassium hydroxide are readily available. They typically would be utilized in fermentation processes that require only relatively minor pH control during the fermentation.

The fermentation product is recovered from the fermentation broth. The manner of accomplishing this will depend on the particular product. However, in general, the organism is separated from the liquid phase, typically via a filtration step or centrifugation step, and the product recovered via, for example, distillation, extraction, crystallization, membrane separation, osmosis, reverse osmosis, or other suitable technique. Organic acids typically will require that the fluid containing the organic acid (and salts thereof) be acidulated using acids such as sulfuric acid to recover the organic acid.

The present process provides the ability to make fermentation products on a production scale level with excellent yields and purity. In an embodiment, the process is carried out in fermentation broth quantities of at least 25,000 gallons. In an embodiment, the batch or fed batch process is carried out to produce batches of at least 25,000 gallons of final fermentation broth.

The present disclosure describes specific embodiments in various aspects of the invention, such as preferred amounts of glucose content, concentrations and fermentation conditions. Combinations of separately discussed aspects of the present invention with each other to provide preferred embodiments are specifically contemplated.

EXAMPLES

Representative embodiments of the present invention will now be described with reference to the following examples that illustrate the principles and practice of the present invention.

Examples

A. Transporter Capability Evaluation

The capability of a cell to transport isomaltose is evaluated by the following protocol:

After harvesting the cells from a fermentation media by centrifugation, the cell pellet is immediately washed with equal volume of sterile deionized water. The pellet is then resuspended in 4 mls of 1.25 mM phthalate buffer (pH 5.0, 30° C.) and transferred to a small magnetically stirred beaker. The final concentration of biomass is 3.0-5.0 grams (cell dry weight) per liter. At time zero, an isomaltose pulse (100 µl, 1M) is added. The rapid alkalinization of the extracellular environment is monitored with a sensitive pH electrode connected to a pH meter with millivolt mode. To calculate initial proton uptake rates the system is calibrated with defined pulses of NaOH (10-50 µl of 10 mM). Isomaltose transport capacity is calculated from the initial slopes of the curves and is expressed in units of (mmol isomaltose/[g cell dry weight*min]).

This protocol is adapted from Jansen, Mickel L. A., Daran-Lapujade, Pascale, de Winde, Johannes H., Piper, Matthew D. W., Pronk, Jack T. 2004. Prolonged Maltose-Limited Cultivation of *Saccharomyces cerevisiae* Selects for Cells with Improved Maltose Affinity and Hypersensitivity. Applied and Environmental Microbiology 70:1956-1963.

B. Isomaltose to Glucose Conversion Evaluation

The capability of a cell to convert isomaltose (or other undesired oligomeric polysaccharides) to glucose is evaluated by the following protocol;

The strains are taken from a fresh YPD plate and used to inoculate 20 mls of YPD liquid media. The culture is allowed to grow at 30° C./250 rpm overnight. The cells are harvested by centrifugation at 3,500 rpm for 4 minutes. The pellets are washed with 10 ml of water and spun at 3,500 rpm for 4 minutes. The pellets (1-50 ml conical tubes) are resuspended in 100 mM Potassium Phosphate buffer (pH6.5) (supplemented with 10 ul/ml protease inhibitor (Calbiochem; cocktail V). Resuspended pellets are transferred to a 1.5 ml screw capped tube and acid washed glass beads (Sigma #G1277) are added. The cells are placed in the bead beater and lysed for 30 second intervals followed by a 3 minute rest on ice; this is repeated a total of 4 times. The tube is then centrifuged at 14,000 rpm for 5 minutes and the supernatant removed and used in the enzyme assay. Activity of α-glucosidase on maltose (maltase) and αMG (α-methyl glucosidase), and isomaltose (isomaltase) is determined by adding 30 µl of crude extract in a final volume of 300 of 50 mM potassium phosphate buffer, pH 6.5, containing 25 mM isomaltose. After 10 min of incubation at 30° C. the reaction is stopped by placing the tube in a water bath set at 80° C. for 5 min. The glucose released is measured on a YSI2950 (Xylem Inc.). The activity is expressed as micromoles of glucose released per milligram of protein/min. Assays are carried out in triplicate. Protein concentration is determined using the Advanced Protein Assay Reagent (Cytoskeleton) using BSA as the standard.

This protocol is adapted from Teste, et. al., 2010. Characterization of a New Multigene Family Encoding Isomaltases in the Yeast *Saccharomyces cerevisiae*, the IMA Family. J. Biol. Chem. 285. 26815-26824

Enzyme activities on other oligosaccharide substrates can likewise be measured by substituting either 100 mM maltose, 100 mM αMG, or undesired oligosaccharides in place of the isomaltose in the assay.

Comments

95DE sugar is an aqueous hydrolyzate of corn starch which contains sugars in approximately the following proportions: 97.1% glucose, 1.1% maltose, 1.2% isomaltose, and 0.7% panose.

One of skill in the art will know how to select suitable sites in a yeast genome for gene integration. Examples of suitable sites for integration of exogenous genes in *Issatchenkia orientalis* include, but are not limited to, the following loci: locus A, which is flanked by SEQ ID NO: 1 and SEQ ID NO: 2; and locus B, which is flanked by SEQ ID NO: 3 and SEQ ID NO: 4. One of skill in the art will recognize how to use the sequences to design PCR primers to verify correct integrations at these loci.

Example 1: Generation of Lactic Acid Producing Yeast Capable of Intracellular Isomaltose Consumption Strain Strain E An *Issatchenkia orientalis* host strain is generated by evolving *I. orientalis* strain ATCC PTA-6658 (Strain A) in a low dilution, low pH, glucose-limited chemostat with externally added lactic acid in the feed medium. Single colonies are isolated from the chemostat and screened for improved growth rate in the presence of free lactic acid. An isolate showing improvement in the screen is designated as Strain B. Both pyruvate decarboxylase (PDC) genes are simultaneously knocked out and replaced with a lactate dehydrogenase (LDH) gene from *Lactobacillus helveticus* to produce Strain C. Both alleles of both L-lactate:cytochrome c oxidoreductase genes (locus A and locus B, as described above) as well as both alleles of the glyceraldehyde-3-phosphate dehydrogenase gene (GPD) are deleted from Strain C to produce Strain D. Strain D is subjected to mutagenesis followed by selection on plates for ability to grow in the presence of an increased concentration of free lactic acid. Single colonies from the selection plates are screened in shake flasks for improved lactic acid productivity. An isolate improved in lactic acid productivity is subjected to a further round of mutagenesis, selection and screening. After four successive rounds of mutagenesis, selection, and screening, a single colony isolate improved in lactic acid productivity is designated Strain E.

Strain 1-1

Strain Strain E is transformed with SEQ ID NO: 5. SEQ ID NO: 5 contains the following elements: i) an expression cassette for a maltase gene from *S. cerevisiae* (ScMAL12), encoding the amino acid sequence SEQ ID NO: 6; and ii) an expression cassette for a maltose/isomaltose transporter gene from *S. cerevisiae* (ScMAL11), encoding the amino acid sequence SEQ ID NO: 7; and iii) flanking DNA for targeted chromosomal integration into integration locus A. Transformants are selected on YNB plates containing 2% maltose as sole carbon source. Resulting transformants are streaked for single colony isolation on YNB plates containing 2% maltose. A single colony is selected. Correct integration of SEQ ID NO: 5 into both alleles of integration locus A of the selected colony is verified by PCR. A PCR verified isolate is designated Strain 1-1.

Strain 1-2

Strain 1-1 is transformed with SEQ ID NO: 8. SEQ ID NO: 8 contains: i) an expression cassette for the selectable marker gene melibiase from *S. cerevisiae* (ScMEL5) flanked by LoxP sites; ii) an expression cassette for an isomaltase gene from *S. cerevisiae* (ScIMA1), encoding the amino acid sequence SEQ ID NO: 9; and iii) flanking DNA for targeted chromosomal integration into integration locus B. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 8 into the selected blue colony is verified by PCR. A PCR verified isolate is designated Strain 1-2.

Strain 1-3

Strain 1-2 is transformed with SEQ ID NO: 10. SEQ ID NO: 10 contains: 1) an expression cassette for the selectable marker gene CYB2A from *I. orientalis* (IoCYB2A) flanked by LoxP sites; ii) an expression cassette for an isomaltase gene from *S. cerevisiae* (ScIMA1), encoding the amino acid sequence SEQ ID NO: 9; and iii) flanking DNA for targeted chromosomal integration into integration locus B. Transformants are selected on YNB plates containing 2% lactic acid as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 10 into the selected blue colony is verified by PCR. A PCR verified isolate is designated Strain 1-3.

Strain 1-4

Strain 1-3 is transformed with the plasmid of SEQ ID NO: 11. SEQ ID NO: 11 contains: i) an expression cassette for the selectable marker gene invertase from *S. cerevisiae* (ScSUC2); and ii) an expression cassette for CRE recombinase gene (Cre) to recycle the selectable markers ScMEL5 & IoCYB2A. Transformants are selected on YNB plates containing 2% sucrose as sole carbon source and 32 µg/ml x-alpha-gal which provides colorimetric indication of the absence of the ScMEL5 marker gene. Resulting transformants are streaked for single colony isolation on YPD containing 32 µg/ml x-alpha-gal. A single white colony is selected. Loss of ScMEL5 and IoCYB2A from the selected white colony is verified by PCR. A PCR verified isolate is designated Strain 1-4.

Strain 1-5

Strain Strain E is transformed with SEQ ID NO: 10. SEQ ID NO: 10 contains: i) an expression cassette for the selectable marker gene CYB2A from *I. orientalis* (IoCYB2A) flanked by LoxP sites; ii) an expression cassette for an isomaltase gene from *S. cerevisiae* (ScIMA1), encoding the amino acid sequence SEQ ID NO: 9; and iii) flanking DNA for targeted chromosomal integration into integration locus B. Transformants are selected on YNB plates containing 2% lactic acid as sole carbon source. Resulting transformants are streaked for single colony isolation on YNB plates containing 2% lactic acid as sole carbon source. A single colony is selected. Correct integration of SEQ ID NO: 10 into the selected colony is verified by PCR. A PCR verified isolate is designated Strain 1-5.

Strain 1-6

Strain 1-5 is transformed with SEQ ID NO: 8. SEQ ID NO: 8 contains: i) an expression cassette for the selectable marker gene melibiase from *S. cerevisiae* (ScMEL5) flanked by LoxP sites; ii) an expression cassette for an isomaltase gene from *S. cerevisiae* (ScIMA1), encoding the amino acid sequence SEQ ID NO: 9; and iii) flanking DNA for targeted chromosomal integration into integration locus B. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YNB plates containing 2% lactic acid containing 32 µg/ml x-alpha-gal. A single blue colony is selected. Correct integration of SEQ ID NO: 8 into the selected blue colony is verified by PCR. A PCR verified isolate is designated Strain 1-6.

Strain 1-7

Strain 1-6 is transformed with the plasmid of SEQ ID NO: 11. SEQ ID NO: 11 contains: i) an expression cassette for the selectable marker gene invertase from *S. cerevisiae* (ScSUC2); and ii) an expression cassette for CRE recombinase gene to recycle the selectable markers ScMEL5 & IoCYB2A. Transformants are selected on YNB plates containing 2% sucrose as sole carbon source and 32 µg/ml x-alpha-gal which provides colorimetric indication of the absence of the ScMEL5 marker gene. Resulting transformants are streaked for single colony isolation on YPD containing 32 µg/ml x-alpha-gal. A single white colony is selected. Loss of ScMEL5 and IoCYB2A from the selected white colony is verified by PCR. A PCR verified isolate is designated Strain 1-7.

Strain 1-8

Strain 1-7 is transformed with SEQ ID NO: 12. SEQ ID NO: 12 contains: i) an expression cassette for the selectable marker gene melibiase from *S. cerevisiae* (ScMEL5); and ii) flanking DNA for targeted chromosomal integration into integration locus A. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 12 into the selected blue colony is verified by PCR. A PCR verified isolate is designated Strain 1-8.

TABLE 1-1

Lactic acid producing yeast

| Strain | Description | Parent |
|---|---|---|
| Strain A | Wild Type | N/A |
| Strain B | Chemostat evolved wild type | Strain A |
| Strain C | IoPDCΔ, LhLDH+ | Strain B |
| Strain D | Mutagenesis and selection for lactic acid resistance, cyb2AΔ, cyb2BΔ, IoGPDΔ | Strain C |
| Strain E | Mutagenesis and selection for lactic acid resistance | Strain D |
| 1-1 | ScMAL11+, ScMAL12+ | Strain E |
| 1-2 | ScMAL11+, ScMAL12+, ScIMA1+, ScMEL5+ | 1-1 |
| 1-3 | ScMAL11+, ScMAL12+, ScIMA1+, ScMEL5+, IoCYB2A+ | 1-2 |
| 1-4 | ScMAL11+, ScIMA1+, ScMAL12+ | 1-3 |
| 1-5 | ScIMA1+, IoCYB2A+ | Strain E |
| 1-6 | ScIMA1+, IoCYB2A+, ScMEL5+ | 1-5 |
| 1-7 | ScIMA1+ | 1-6 |
| 1-8 | ScIMA1+, ScMEL5+ | 1-7 |

Example 2: Generation of Ethanol Producing Yeast Capable of Intracellular Isomaltose Consumption Strain F Both alleles of an L-lactate:cytochrome c oxidoreductase (locus A) are deleted from strain Strain B to produce Strain F.

Strain 2-1

Strain Strain B is transformed with SEQ ID NO: 13. SEQ ID NO: 13 contains: i) an expression cassette for the selectable marker gene melibiase from *S. cerevisiae* (ScMEL5); ii) an expression cassette for a maltose transporter gene from *S. cerevisiae* (ScMAL11), encoding the amino acid sequence SEQ ID NO: 7; and iii) flanking DNA for targeted chromosomal integration into integration locus A. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 13 into the selected blue colony is verified by PCR. A PCR verified isolate is designated strain 2-1.

Strain 2-2

Strain F is transformed with SEQ ID NO: 8. SEQ ID NO: 8 contains: i) an expression cassette for the selectable marker gene melibiose from *S. cerevisiae* (ScMEL5); ii) an expression cassette for a isomaltase gene from *S. cerevisiae* (ScIMA1), encoding the amino acid sequence SEQ ID NO: 9; and iii) flanking DNA for targeted chromosomal integration into locus B. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 8 into the selected blue colony is verified by PCR. A PCR verified isolate is designated strain 2-2a.

Strain 2-2a is transformed with SEQ ID NO: 10. SEQ ID NO: 10 contains: i) an expression cassette for the selectable marker gene L-lactate cytochrome-c oxidoreductase (CYB2A); ii) an expression cassette for a isomaltase gene from *S. cerevisiae* (ScIMA1), encoding the amino acid sequence SEQ ID NO: 9; and iii) flanking DNA for targeted chromosomal integration into locus B. Transformants are selected on YNB plates containing 2% L-lactate as the sole carbon source. Resulting transformants are streaked for single colony isolation on YPD. Correct integration of SEQ ID NO: 10 is verified by PCR. A PCR verified isolate is designated strain 2-2.

Strain 2-3

Strain 2-2 is transformed with SEQ ID NO: 11. SEQ ID NO: 11 contains: i) an expression cassette for the selectable marker gene invertase from *S. cerevisiae* (ScSUC2); and ii) an expression cassette for CRE recombinase gene. Transformants are selected on YNB 2% sucrose as the sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single white colony is selected. Loss of ScMEL5 and IoCYB2A from the selected white colony is verified by PCR. A PCR verified isolate is designated strain 2-3a.

Strain 2-3a is transformed with SEQ ID NO: 13. SEQ ID NO: 13 contains: i) an expression cassette for the selectable marker gene melibiase from *S. cerevisiae* (ScMEL5); ii) an expression cassette for a maltose transporter gene from *S. cerevisiae* (ScMAL11), encoding the amino acid sequence SEQ ID NO: 7; and iii) flanking DNA for targeted chromosomal integration into integration locus A. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 13 into the selected blue colony is verified by PCR. A PCR verified isolate is designated strain 2-3.

Strain 2-4

Strain F is transformed with SEQ ID NO: 14. SEQ ID NO: 14 contains: i) an expression cassette for the selectable marker gene melibiose from *S. cerevisiae* (ScMEL5); ii) an expression cassette for an isomaltase gene from *S. cerevisiae* (ScIMA1), encoding the amino acid sequence SEQ ID NO: 9; and iii) flanking DNA for targeted chromosomal integration into locus B. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. Correct integration of SEQ ID NO: 14 into the selected blue colony is verified by PCR. A PCR verified isolate is designated strain 2.4a.

Strain 2-4a is transformed with SEQ ID NO: 15. SEQ ID NO: 15 contains: i) an expression cassette for the selectable marker gene L-lactate cytochrome-c oxidoreductase (CYB2A); ii) an expression cassette for a isomaltase gene from *S. cerevisiae* (ScIMA1), encoding the amino acid sequence SEQ ID NO: 9; and iii) flanking DNA for targeted chromosomal integration into locus B. Transformants are selected on YNB plates containing 2% L-lactate as the sole carbon source. Resulting transformants are streaked for single colony isolation on YPD. Correct integration of SEQ ID NO: 15 is verified by PCR. A PCR verified isolate is designated 2-4b.

Strain 2-4b is transformed with SEQ ID NO: 11. SEQ ID NO: 11 contains: i) an expression cassette for the selectable marker gene invertase from *S. cerevisiae* (ScSUC2); and ii) an expression cassette for CRE recombinase gene. Transformants are selected on YNB 2% sucrose as the sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single white colony is selected. Loss of ScMEL5 and IoCYB2A from the selected white colony is verified by PCR. A PCR verified isolate is designated strain 2-4c.

Strain 2-4c is transformed with SEQ. ID. NO: 13. SEQ ID NO: 13 contains: i) an expression cassette for the selectable marker gene melibiase from *S. cerevisiae* (ScMEL5); ii) an expression cassette for a maltose transporter gene from *S. cerevisiae* (ScMAL11), encoding the amino acid sequence SEQ ID NO: 7; and iii) flanking DNA for targeted chromosomal integration into integration locus A. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YPD containing 32 µg/ml x-alpha-gal. A single blue colony is selected. A PCR verified isolate is designated strain 2-4d.

Strain 2-4d is transformed with SEQ ID NO: 5. SEQ ID NO: 5 contains the following elements: i) an expression cassette for a maltase gene from *S. cerevisiae* (ScMAL12), encoding the amino acid sequence SEQ ID NO: 6; ii) an expression cassette for a maltose/isomaltose transporter gene from *S. cerevisiae* (ScMAL11), encoding the amino acid sequence SEQ ID NO: 7; and iii) flanking DNA for targeted chromosomal integration into integration locus A. Transformants are selected on YNB plates containing 2% maltose as the sole carbon source. Resulting transformants are streaked for single colony isolation on YPD. A single colony is selected. Correct integration of SEQ ID NO: 5 into both alleles of integration locus A of the selected colony is verified by PCR. A PCR verified isolate is designated strain 2-4.

TABLE 2-1

Ethanol producing yeast strains

| Strain | Description | Parent |
| --- | --- | --- |
| Strain A | Wild Type | Na |
| Strain B | Chemostat evolved wild type | Strain A |
| Strain F | cyb2AΔ | Strain B |
| 2-1 | ScMAL11+, ScMEL5+ | Strain B |
| 2-2 | ScIMA1+, ScMEL5+, IoCYB2A+ | Strain F |
| 2-3 | ScMAL11+, ScIMA1+, ScMEL5+ | 2-2 |
| 2-4 | ScMAL11+, ScIMA1+, ScMAL12+ | Strain F |

Example 3: Creation of Yeast Strains with Alternative Isomaltose Transporters

Strain 3-1

Strain 1-8 is transformed with SEQ ID NO: 16. SEQ ID NO: 16 contains: i) a maltose/isomaltose transporter gene from *S. cerevisiae* (ScMAL11), encoding the amino acid sequence SEQ ID NO: 7; and ii) flanking DNA for targeted chromosomal integration into integration locus A. Transformants are selected on YNB plates containing 2% isomaltose as sole carbon source and 32 µg/ml x-alpha-gal which provides colorimetric indication of the absence of the ScMEL5 marker gene. Resulting transformants are streaked for single colony isolation on YPD plates containing 32

μg/ml x-alpha-gal. A single white colony is selected. Correct integration of SEQ ID NO: 16 into the selected colony is verified by PCR. A PCR verified isolate is designated Strain 3-1.

Strain 3-2

Strain 1-8 is transformed with SEQ ID NO: 17. SEQ ID NO: 17 contains: i) a maltose/isomaltose transporter gene, encoding the amino acid sequence SEQ ID NO: 18; and ii) flanking DNA for targeted chromosomal integration into integration locus A. Transformants are selected on YNB plates containing 2% isomaltose as sole carbon source and 32 μg/ml x-alpha-gal which provides colorimetric indication of the absence of the ScMEL5 marker gene. Resulting transformants are streaked for single colony isolation on YPD plates containing 32 μg/ml x-alpha-gal. A single white colony is selected. Correct integration of SEQ ID NO: 17 into the selected colony is verified by PCR. A PCR verified isolate is designated Strain 3-2.

Strain 3-3

Strain 1-8 is transformed with SEQ ID NO: 19. SEQ ID NO: 19 contains: i) an expression cassette for a maltose/isomaltose transporter gene from *D. hansenii* (DhMAL11), encoding the amino acid sequence SEQ ID NO: 20; and ii) flanking DNA for targeted chromosomal integration into integration locus A. Transformants are selected on YNB plates containing 2% isomaltose as sole carbon source and 32 μg/ml x-alpha-gal which provides colorimetric indication of the absence of the ScMEL5 marker gene. Resulting transformants are streaked for single colony isolation on YPD plates containing 32 μg/ml x-alpha-gal. A single white colony is selected. Correct integration of SEQ ID NO: 19 into the selected colony is verified by PCR. A PCR verified isolate is designated Strain 3-3.

Strain 3-4

Strain 1-8 is transformed with SEQ ID NO: 21. SEQ ID NO: 21 contains: i) an expression cassette for a maltose/isomaltose transporter gene from *T. delbrueckii* (TdMAL11), encoding the amino acid sequence SEQ ID NO: 22; and ii) flanking DNA for targeted chromosomal integration into integration locus A. Transformants are selected on YNB plates containing 2% isomaltose as sole carbon source and 32 μg/ml x-alpha-gal which provides colorimetric indication of the absence of the ScMEL5 marker gene. Resulting transformants are streaked for single colony isolation on YPD plates containing 32 μg/ml x-alpha-gal. A single white colony is selected. Correct integration of SEQ ID NO: 21 into the selected colony is verified by PCR. A PCR verified isolate is designated Strain 3-4.

TABLE 3-1

| Strain | Description | Parent |
|---|---|---|
| 3-1 | ScIMA1+, ScMAL11 | 1-8 |
| 3-2 | ScIMA1+, gene encoding SEQ ID NO: 18 (a variant of ScMAL11) | 1-8 |
| 3-3 | ScIMA1+, DhMAL11 | 1-8 |
| 3-4 | ScIMA1+, TdMAL11 | 1-8 |

Example 4: Demonstrate in Shake Flask that Transformation of a Yeast with an Isomaltase and an Isomaltose Transporter Enables Consumption of Isomaltose in a Lactic Acid Producing Yeast Strains Strain E, 1-8, 1-4 & 3-1 are streaked out for single colonies on a YPD plate and incubated at 30° C. until single colonies are visible (1-2 days). Cells from plates are scraped into sterile growth medium and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Prior to inoculation, the 250 mL non-baffled shake flasks containing 0.18 g dry $CaCO_3$ are sterilized. Immediately prior to inoculating, 20 mL of shake flask medium is added to the dry calcium carbonate. The shake flask medium is sterilized, pH to 4.0, and contains the following components: 1.95 mL/L of 40% urea, 0.13 g/L magnesium sulfate heptahydrate, 0.91 mL/L of an APK solution [4.15% (w/v) nitrogen (in the form of ammonium) and 9.35% (w/v) phosphorous (in the form of phosphate), and 8.44% (w/v) potassium], 1 mL/L of the trace element solution described in table 4-1, 1 mL/L of a vitamin solution (0.05 g/L biotin), a quantity of 95DE sugar to result in 100.0 g/L glucose, 0.3 g/L glycerol, and 4.0 g/L 2-(N-Morpholino) ethanesulfonic acid (MES).

The inoculated flask is incubated at 34° C. with shaking in an orbital shaker at 150 rpm for 72 hours. Samples are taken and analyzed for lactic acid and glucose concentrations in the broth during fermentation by high performance liquid chromatography with refractive index detector. Maltose and isomaltose are determined by high performance liquid chromatography with evaporative light scattering detector.

TABLE 4-1

| | Trace composition | | | |
|---|---|---|---|---|
| Chemicals | Formula | MW | gram/L | Product code |
| EDTA (Titriplex III ®) | $C_{10}H_{14}N_2Na_2O_8 \cdot 2H_2O$ | 372.24 | 15.00 | Sigma I-5134 |
| Zinc sulphate heptahydrate | $ZnSO_4 \cdot 7H_2O$ | 287.54 | 4.50 | Fisher Z68-500 |
| Manganese chloride dihydrate | $MnCl_2 \cdot 2H_2O$ | 161.88 | 1.0 | Sigma M-8530 |
| Copper(II)sulphate pentahydrate | $CuSO_4 \cdot 5H_2O$ | 249.68 | 0.30 | Sigma C-3036 |
| Iron sulphate heptahydrate | $FeSO_4 \cdot 7H_2O$ | 278.02 | 3.00 | Fisher I146-500 |

TABLE 4-2

| | Isomaltose Depletion | | | | |
|---|---|---|---|---|---|
| Strain | Glucose initial (g/L) | Glucose final (g/L) | Isomaltose initial (g/L) | Isomaltose final (g/L) | Strain Description |
| Strain E | 107.1 | <0.43 | 1.24 | 1.39 | Parent |
| 1-8 | 107.1 | <0.43 | 1.24 | 1.37 | isomaltase ScIMA1+ |

TABLE 4-2-continued

| | Isomaltose Depletion | | | | |
|---|---|---|---|---|---|
| Strain | Glucose initial (g/L) | Glucose final (g/L) | Isomaltose initial (g/L) | Isomaltose final (g/L) | Strain Description |
| 1-4 | 107.1 | <0.43 | 1.24 | <0.46 | transporter ScMAL11+, isomaltase ScIMA1+, maltase ScMAL12+ |
| 3-1 | 107.1 | <0.43 | 1.24 | <0.46 | isomaltase ScIMA1+, transporter ScMAL11 |

Yeast strains 1-4 and 3-1 containing the gene encoding the maltose/isomaltose transporter, as well as the gene encoding the isomaltase show improved depletion of isomaltose when compared to their parent strain (Strain E) as well as when compared with a strain containing the gene encoding the isomaltase but lacking the gene encoding the maltose/isomaltose transporter (strain 1-8).

Example 5: Demonstrate in Shake Flask that Transformation of a Yeast with an Isomaltase and an Isomaltose Transporter Enables Consumption of Isomaltose in an Ethanol Producing Yeast Shake Flask Evaluation for Ethanol Production The strains listed in Table 5-3 are streaked out for single colonies on a YPD plate and incubated at 34° C. until single colonies are visible (1-2 days). Cells from the YPD plate are scraped into sterile shake flask medium and the optical density ($OD_{600}$) is measured. Optical density is measured at wavelength of 600 nm with a 1 cm pathlength using a model Genesys20 spectrophotometer (Thermo Scientific).

A shake flask is inoculated with the cell slurry to reach an initial $OD_{600}$ of 0.1-0.3. Immediately prior to inoculating, 50 mL of shake flask medium is added to a 125 mL baffled shake flask. The shake flask medium is a filter sterilized, pH 6.0 aqueous solution of urea (2.27 g/L), magnesium sulfate heptahydrate (0.50 g/L), potassium phosphate monobasic (3.00 g/L), 1 mL/L of the trace element solution described in table 5-1, and 1 mL/L of the vitamin solution described in table 5-2, 95DE sugar (300 mL/L), and 2-(N-Morpholino) ethanesulfonic acid (IVIES) (19.5 g/L).

The inoculated flask is incubated at 34° C. with shaking in an orbital shake at 125 rpm for 72 hours. Samples are taken and analyzed for ethanol and glucose concentrations in the broth during fermentation by high performance liquid chromatography with refractive index detector. Maltose, isomaltose and panose are determined by high performance liquid chromatography with evaporative light scattering detector.

The results of the shake flask, shown in Table 5-3, demonstrate an improvement in isomaltose and panose depletion when both the genes encoding for the maltose/isomaltose transporter (ScMAL11) and encoding for the isomaltase (ScIMA1) are present.

TABLE 5-1

| Trace element solution | |
|---|---|
| Component | g/L |
| EDTA | 15.0 |
| Zinc Sulfate heptahydrate | 4.5 |
| Manganese chloride | 1.0 |
| Cobalt(II) chloride hexahydrate | 0.3 |
| Copper (II) sulphate pentahydrate | 0.3 |
| Disodium molybdenum dehydrate | 0.4 |
| Calcium chloride dehydrate | 4.5 |
| Iron sulphate heptahydrate | 3.0 |
| Boric acid | 1.0 |
| Potassium iodide | 0.1 |

TABLE 5-2

| Vitamin solution | | | | |
|---|---|---|---|---|
| Chemicals | Formula | MW | gram/L | Product code |
| Biotin (D−) | C10H16N2O3S | 244.31 | 0.05 | Sigma B4639 |
| Ca D(+) panthotenate | C18H32CaN2O10 | 476.54 | 1 | Sigma C8731 |
| Nicotinic acid | C6H5NO2 | 123.11 | 5 | Sigma N4126 |
| Myo-inositol (for microbiology) | C6H12O6 | 180.16 | 25 | Sigma I7508 |
| Thiamine hydrochloride | C12H18C12N4OS•xH2O | 337.27 | 1 | Sigma T4625 |
| Pyridoxine hydrochloride | C8H12ClNO3 | 205.64 | 1 | Sigma P9755 |
| p-Aminobenzoic acid | C7H7NO2 | 137.14 | 0.2 | Sigma A9878 |

Tables 5-3—Glucose and Oligosaccharide Levels Before and after Fermentation.

The sugar concentrations shown in tables 5.3a and 5.3b are the results of the same shake flask experiments.

TABLE 5-3a

| Glucose and maltose levels before and after fermentation | | | | | |
|---|---|---|---|---|---|
| Strain | Glucose initial (g/L) | Glucose final (g/L) | Maltose initial (g/L) | Maltose final (g/L) | Strain Description |
| Strain F | 106.5 | <0.43 | 1.462 | 1.416 | parent |
| 2-1 | 106.5 | <0.43 | 1.462 | 1.235 | transporter ScMAL11+ |
| 2-3 | 106.5 | <0.43 | 1.462 | 0.371 | transporter ScMAL11+, iIsomaltase ScIMA1+ |

TABLE 5-3a-continued

Glucose and maltose levels before and after fermentation

| Strain | Glucose initial (g/L) | Glucose final (g/L) | Maltose initial (g/L) | Maltose final (g/L) | Strain Description |
|---|---|---|---|---|---|
| 2-4 | 106.5 | <0.43 | 1.462 | <0.36 | transporter ScMAL11+, isomaltase ScIMA1+, maltase ScMAL12+ |

TABLE 5-3b

Isomaltose and panose levels before and after fermentation

| Strain | Iso-maltose initial (g/L) | Iso-maltose final (g/L) | Panose initial (g/L) | Panose final (g/L) | Strain Description |
|---|---|---|---|---|---|
| Strain F | 1.029 | 1.211 | 1.289 | 1.382 | parent |
| 2-1 | 1.029 | 0.897 | 1.289 | 1.517 | transporter ScMAL11+ |
| 2-3 | 1.029 | <0.46 | 1.289 | 0.458 | transporter ScMAL11+, isomaltase ScIMA1+ |
| 2-4 | 1.029 | <0.46 | 1.289 | 0.843 | transporter ScMAL11+, isomaltase ScIMA1+, maltase ScMAL12+ |

Example 6: Operating a Fermentation in a Fed-Batch Mode Improves Isomaltose Consumption in a Yeast that Produces Lactic Acid as Compared to Straight Batch Fermentation Example 6-1: Straight Batch Fermentations with Lactic Acid Producing Strains 1-4 and Strain E The lactic acid producing yeast strains 1-4 and Strain E are run in fermenters to assess maltose and isomaltose consumption as well as lactic acid production. Glycerol stocks for strains 1-4 and Strain E are prepared according to methods known in the art. The final concentration of glycerol in the glycerol stock is 20% (v/v). The cell concentration in the glycerol stock is between 0.4 and 0.8 g/L cell dry weight. The cryovial containing the glycerol stock is placed in a −80° C. freezer for storage.

Fermentors with a working volume of 20 L are filled with 5379.3 g of a 32% (w/v) solution of 95DE sugar, 1 mL of concentrated (95% w/v) sulfuric acid, and 6533.1 g deionized water and heat sterilized. After sterilization, fermentors are cooled to 34 C. After cooling, the following sterile components are added to the fermentor to generate the fermentor medium: 23.4 g of an aqueous solution of 40% (w/v) urea, 12 g of an aqueous solution of 125 g/L magnesium sulfate heptahydrate, 12.6 g of an APK solution [4.15% (w/v) nitrogen (in the form of ammonium) and 9.35% (w/v) phosphorous (in the form of phosphate), and 8.44% (w/v) potassium], 12 g of the trace element solution described in table 5-1 and 12 g of an aqueous vitamin solution (0.05 g/L biotin), 6 g of an aqueous 10% (w/w) glycerol solution, 10 g of a 1:100 aqueous dilution of Lubrizol antifoam (Lubrizol Corp, part number BCC-627), and a mass of deionized water to bring the total mass of fermentor medium to 12 kg. Cryovials containing glycerol stocks for strains 1-4 and Strain E are warmed by incubation at room temperature until just thawed. Separate fermentors are inoculated with the thawed glycerol stocks for each of the strains. pH in the fermentors is maintained at 4.4 by controlled addition of a 30% suspension of lime (calcium hydroxide) until 620 g of the lime suspension has been added, after which no further pH control occurs. The fermentors are sparged with 1 SLPM (standard liters per minute) air through a sparge ring at the base of the vessel. An oxygen uptake rate of 12-13 mmol $O_2$/(L*h) is achieved by selecting an appropriate agitation speed. These fermentations are operated such that after the cells achieve a sufficient density, oxygen limitation is achieved and subsequently maintained throughout the rest of the fermentation (e.g., dissolved oxygen less than about 10.) Dissolved oxygen is measured using Mettler Toledo INPRO® 6800 sensor (Mettler-Toledo GmbH, Urdorf, Switzerland), calibrated prior to inoculation. 0% is calibrated by unplugging the probe and measuring a null signal, 100% is calibrated using air sparging according to the run conditions in the vessel as detailed above (prior to inoculation).

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific). Unless explicitly noted otherwise, an experimentally derived conversion factor of 1.33 $OD_{600}$ units per 1 g dry cell mass is used to estimate cell dry weight.

Oxygen uptake rate ("OUR") is calculated using methods known to those in the art as described above. For this example, Oxygen, $N_2$ and $CO_2$ values are measured by a mass spectrometer.

Samples are taken immediately after inoculation, at the end of the batch, and periodically throughout the fermentation. Samples are analyzed for biomass growth via $OD_{600}$, lactic acid and glucose concentration by high performance liquid chromatography with refractive index detector and for maltose and isomaltose by high performance liquid chromatography with evaporative light scattering detection (ELSD).

The residual oligosaccharide concentrations resulting from the straight batch fermentations are shown in tables 6-1 and 6-2.

Example 6-2: Fed-Batch Fermentations with Lactic Acid Producing Strains 1-4 and Strain E The lactic acid producing yeast strains 1-4 and Strain E are run in fermenters to assess maltose and isomaltose consumption as well as lactic acid production. Glycerol stocks for strains 1-4 and Strain E are prepared according to methods known in the art. The final concentration of glycerol in the glycerol stock is 20% (v/v). The cell concentration in the glycerol stock is between 0.4 and 0.8 g/L cell dry weight. The cryovial containing the glycerol stock is placed in a −80° C. freezer for storage.

Fermentors with a working volume of 20 L are filled with 1840.0 g of a 32% (w/v) solution of 95DE sugar, 0.5 mL of concentrated (95% w/v) sulfuric acid, and 6533.1 g deionized water and heat sterilized. After sterilization, fermentors are cooled to 34 C. After cooling, the following sterile components are added to the fermentor to generate the fermentor medium: 23.4 g of an aqueous solution of 40% (w/v) urea, 12 g of an aqueous solution of 125 g/L magnesium sulfate heptahydrate, 12.6 g of an APK solution [4.15%

(w/v) nitrogen (in the form of ammonium) and 9.35% (w/v) phosphorous (in the form of phosphate), and 8.44% (w/v) potassium], 12 g of the trace element solution described in table 5-1 and 12 g of an aqueous vitamin solution (0.05 g/L biotin), 6 g of an aqueous 10% (w/w) glycerol solution, 10 g of a 1:100 aqueous dilution of Lubrizol antifoam (Lubrizol Corp, part number BCC-627), and a mass of deionized water to bring the total mass of fermentor medium to 12 kg. Cryovials containing glycerol stocks for strains 1-4 and Strain E are warmed by incubation at room temperature until just thawed. Separate fermentors are inoculated with the thawed glycerol stocks for each of the strains. pH in the fermentors is maintained at 4.4 by controlled addition of a 30% suspension of lime (calcium hydroxide) until 620 g of the lime suspension has been added, after which no further pH control occurs. The fermentors are sparged with 1 SLPM (standard liters per minute) air through a sparge ring at the base of the vessel. An oxygen uptake rate of 12-13 mmol $O_2/(L*h)$ is achieved by selecting an appropriate agitation speed. These fermentations are operated such that after the cells achieve a sufficient density, oxygen limitation is achieved and subsequently maintained throughout the rest of the fermentation (e.g., dissolved oxygen less than about 10%). Dissolved oxygen is measured using Mettler Toledo INPRO® 6800 sensor (Mettler-Toledo GmbH, Urdorf, Switzerland), calibrated prior to inoculation. 0% is calibrated by unplugging the probe and measuring a null signal, 100% is calibrated using air sparging according to the run conditions in the vessel as detailed above (prior to inoculation).

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific). Unless explicitly noted otherwise, an experimentally derived conversion factor of 1.33 $OD_{600}$ units per 1 g dry cell mass is used to estimate cell dry weight.

Oxygen uptake rate ("OUR") is calculated using methods known to those in the art. For this example, Oxygen, $N_2$ and $CO_2$ values are measured by a mass spectrometer. Samples are taken immediately after inoculation, at the end of the batch, and periodically throughout the fermentation. Samples are analyzed for biomass growth via $OD_{600}$; lactic acid and glucose concentration by high performance liquid chromatography with refractive index detector; and for maltose and isomaltose by high performance liquid chromatography with evaporative light scattering detection (ELSD).

A glucose feed solution is prepared. A 4 L glass bottle containing 3539.3 g of a 32% (w/v) solution of 95DE sugar with 0.5 mL of concentrated (95% w/v) sulfuric acid is heat sterilized at 110° C. for 25 minutes.

After inoculation, the fermentation proceeds until the glucose concentration is between 3 and 7 g/L, at which point the glucose feed begins. The glucose feed solution is pumped into the fermentor at an initial flow rate of approximately 150 g/h. Glucose concentration in the fermentor is monitored by YSI analysis of fermentation samples. The flow rate of the feed solution is adjusted to maintain a glucose concentration in the fermentor between 3 and 7 g/L. The feeding continues until the entire 3539.3 g of glucose is added to the fermentor.

In fed batch fermentations, strain 1-4, which contains a maltose/isomaltose transporter gene, a maltase gene, and an isomaltase gene, is compared with the parental strain Strain E, lacking the same three genes for oligomeric sugar consumption. In tables 6-1 and 6-2, it can be observed that strain 1-4 demonstrates improved depletion of both isomaltose and maltose compared with Strain E. The lactic acid production of strain 1-4 remains comparable to that of strain Strain E.

The residual isomaltose concentration, after completion of the feed and at the time of dextrose depletion, is measured for strain 1-4 in straight batch and fed batch fermentations. The results are shown in tables 6-1 and 6-2. The results show that the fed batch fermentation using the described genetically modified yeast results in lower residual isomaltose and lower residual maltose compared with the residual isomaltose and residual maltose in the straight batch.

TABLE 6-1

Isomaltose consumption in straight batch and fed-batch fermentations

| | | Straight batch | | Fed Batch (average of duplicates) | |
|---|---|---|---|---|---|
| Strain | Description | Isomaltose initial (g/L) | Isomaltose final (g/L) | Isomaltose initial (g/L) | Isomaltose final (g/L) |
| Strain E | Parent | N/A | N/A | 0.74 (See note below.) | 1.79 |
| 1-4 | transporter ScMAL11+, isomaltase ScIMA1+, maltase ScMAL12+ | 1.82 | 1.63 | 0.68 (See note below.) | 1.51 |

Note:
In the fed-batch fermentation, only a portion of the 95DE sugar is added up front, while the rest is fed later. So, while the initial isomaltose is lower in the fed-batch, total amount added across the fermentation is the same as in the straight batch.

TABLE 6-2

Maltose consumption in straight batch and fed-batch fermentations

| | | Straight batch | | Fed Batch (average of duplicates) | |
|---|---|---|---|---|---|
| Strain | Description | Maltose initial (g/L) | Maltose final (g/L) | Maltose initial (g/L) | Maltose final (g/L) |
| Strain E | Parent | N/A | N/A | 0.82 (See note below.) | 1.48 |
| 1-4 | transporter ScMAL11+, isomaltase ScIMA1+, maltase ScMAL12+ | 1.94 | 1.63 | 0.81 (See note below.) | 1.11 |

Note:
In the fed-batch fermentation, only a portion of the 95DE sugar is added up front, while the rest is fed later. So, while the initial maltose is lower in the fed-batch, total amount added across the fermentation is the same as in the straight batch.

Example 7: Operating a Fermentation in a Fed-Batch Mode Improves Isomaltose Consumption in a Yeast that Produces Ethanol as Compared to a Straight Batch Fermentation Example 7-1: Straight Batch Fermentations with Ethanol Producing Strains 2-4 and Strain F The ethanol producing yeast strains 2-4 and CD Strain F are run in fermenters to assess maltose and isomaltose consumption as well as ethanol production. Glycerol stocks for strains 2-4 and CD Strain F are prepared according to methods known in the art. The final concentration of glycerol in the glycerol stock is 20% (v/v). The cell concentration in the glycerol stock is between 0.4 and 0.8 g/L cell dry weight. The cryovial containing the glycerol stock is placed in a −80° C. freezer for storage.

Fermentors with a working volume of 20 L are filled with 6724.1 g of a 32% (w/v) solution of 95DE sugar, 1 mL of concentrated (95% w/v) sulfuric acid, and 7620.8 g deionized water and heat sterilized. After sterilization, fermentors are cooled to 34 C. After cooling, the following sterile components are added to the fermentor to generate the fermentor medium: 600 mL of 25× DM Salt solution (56.8 g/L urea, 12.5 g/L magnesium sulfate heptahydrate, and 75 g/L potassium phosphate monobasic in aqueous solution), 15 mL vitamin solution (Table 5-2), 15 mL trace element solution (Table 5-1), 10 g of an aqueous 10% (w/w) glycerol solution, 15 g of a 1:100 aqueous dilution of Lubrizol antifoam (Lubrizol Corp, part number BCC-627), and a mass of deionized water to bring the total mass of fermentor medium to 15 kg.

Cryovials containing glycerol stocks for strains 2-4 and CD Strain F are warmed by incubation at room temperature until just thawed. Separate fermentors are inoculated with the thawed glycerol stocks for each of the strains. pH in the fermentors is maintained at 4.0 by controlled addition of 15% ammonium hydroxide or 2N sulfuric acid. The fermentors are sparged with 2.5 SLPM (standard liters per minute) air into the head space above the liquid. An oxygen uptake rate of 2-3 mmol $O_2$/(L*h) is achieved by selecting an appropriate agitation speed. These fermentations are operated such that after the cells achieve a sufficient density, oxygen limitation is achieved and subsequently maintained throughout the rest of the fermentation (e.g., dissolved oxygen less than about 10%). Dissolved oxygen is measured using Mettler Toledo INPRO® 6800 sensor (Mettler-Toledo GmbH, Urdorf, Switzerland), calibrated prior to inoculation. 0% is calibrated by unplugging the probe and measuring a null signal, 100% is calibrated using air sparging according to the run conditions in the vessel as detailed above (prior to inoculation).

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific).

Oxygen uptake rate ("OUR") is calculated using methods known to those in the art as described above. For this example, Oxygen, $N_2$ and $CO_2$ values are measured by a mass spectrometer.

Samples are taken immediately after inoculation, at the end of the batch, and periodically throughout. Samples are analyzed for biomass growth via $OD_{600}$; ethanol and glucose by high performance liquid chromatography with refractive index detector; and for maltose and isomaltose by high performance liquid chromatography with evaporative light scattering detection (ELSD).

In straight batch fermentations, strain 2-4, which contains a maltose/isomaltose transporter gene, a maltase gene, and an isomaltase gene, is compared with the parental strain Strain F, lacking the same three genes for oligomeric sugar consumption. In tables 7-1 and 7-2, it can be observed that strain 2-4 demonstrates improved depletion of both isomaltose and maltose compared with Strain F. The ethanol production of strain 2-4 remains comparable to that of strain Strain F.

Example 7-2: Fed-Batch Fermentations with Ethanol Producing Strains 2-4 and Strain F The ethanol producing yeast strains 2-4 and CD Strain F are run in fermenters to assess maltose and isomaltose consumption as well as ethanol production. Glycerol stocks for strains 2-4 and CD Strain F are prepared according to methods known in the art. The final concentration of glycerol in the glycerol stock is 20% (v/v). The cell concentration in the glycerol stock is between 0.4 and 0.8 g/L cell dry weight. The cryovial containing the glycerol stock is placed in a −80° C. freezer for storage.

Fermentors with a working volume of 20 L are filled with 2300.0 g of a 32% (w/v) solution of 95DE sugar, 0.5 mL of concentrated (95% w/v) sulfuric acid, and 7620.8 g deionized water and heat sterilized. After sterilization, fermentors are cooled to 34 C. After cooling, the following sterile components are added to the fermentor to generate the fermentor medium: 600 mL of 25×DM Salt solution (56.8 g/L urea, 12.5 g/L magnesium sulfate heptahydrate, and 75 g/L potassium phosphate monobasic in aqueous solution), 15 mL vitamin solution (Table 5-2), 15 mL trace element solution (Table 5-1), 10 g of an aqueous 10% (w/w) glycerol solution, 15 g of a 1:100 aqueous dilution of Lubrizol antifoam (Lubrizol Corp, part number BCC-627), and a mass of deionized water to bring the total mass of fermentor medium to 15 kg.

Cryovials containing glycerol stocks for strains 2-4 and CD Strain F are warmed by incubation at room temperature until just thawed. Separate fermentors are inoculated with the thawed glycerol stocks for each of the strains. pH in the fermentors is maintained at 4.0 by controlled addition of 15% ammonium hydroxide or 2N sulfuric acid. The fermentors are sparged with 2.5 SLPM (standard liters per minute) air into the head space above the liquid. An oxygen uptake rate of 2-3 mmol $O_2$/(L*h) is achieved by selecting an appropriate agitation speed. These fermentations are operated such that after the cells achieve a sufficient density, oxygen limitation is achieved and subsequently maintained throughout the rest of the fermentation (e.g., dissolved oxygen less than about 10%). Dissolved oxygen is measured using Mettler Toledo INPRO® 6800 sensor (Mettler-Toledo GmbH, Urdorf, Switzerland), calibrated prior to inoculation. 0% is calibrated by unplugging the probe and measuring a null signal. 100% is calibrated using air sparging according to the run conditions in the vessel as detailed above (prior to inoculation).

Cell concentration is obtained from an optical density measurement using an established conversion factor between dry cell mass and optical density. Optical density is measured at a wavelength of 600 nm with a 1 cm pathlength using a model Genesys20 spectrophotometer (Thermo Scientific).

Oxygen uptake rate ("OUR") is calculated using methods known to those in the art. For this example, Oxygen, $N_2$ and $CO_2$ values are measured by a mass spectrometer. Samples are taken immediately after inoculation, at the end of the batch, and periodically throughout. Samples are analyzed for biomass growth via $OD_{600}$; ethanol and glucose by high performance liquid chromatography with refractive index detector; and for maltose and isomaltose by high performance liquid chromatography with evaporative light scattering detection (ELSD).

A glucose feed solution is prepared. A 4 L glass bottle containing 4424.1 g of a 32% (w/v) solution of 95DE sugar with 0.5 mL of concentrated (95% w/v) sulfuric acid is heat sterilized at 110° C. for 25 minutes.

After inoculation, the fermentation proceeds until the glucose concentration is between 3 and 7 g/L, at which point the glucose feed begins. The glucose feed solution is pumped into the fermentor at an initial flow rate of approximately 470 g/h. Glucose concentration in the fermentor is monitored by YSI analysis of fermentation samples. The flow rate of the feed solution is adjusted to maintain a glucose concentration in the fermentor between 3 and 7 g/L. The feeding continues until the entire 4424.1 g of glucose is added to the fermentor.

The residual isomaltose concentration, after completion of the feed and at the time of dextrose depletion, is measured for strain 2-4 in straight batch and fed batch fermentations. The results are shown in tables 7-1 and 7-2. The results show that the fed batch fermentation using the described genetically modified yeast results in lower residual isomaltose and lower residual maltose compared with the residual isomaltose and residual maltose in the straight batch.

TABLE 7-1

Isomaltose consumption in straight batch and fed-batch fermentations

| | | Straight batch | | Fed Batch (average of duplicates) | |
|---|---|---|---|---|---|
| Strain | Description | Isomaltose initial (g/L) | Isomaltose final (g/L) | Isomaltose initial (g/L) | Isomaltose final (g/L) |
| Strain F | Parent | 1.80 | 1.91 | N/A | N/A |
| 2-4 | Transporter ScMAL11+, Isomaltase ScIMA1+, Maltase ScMAL12+ | 1.82 | 0.72 | 0.95 (See note below.) | 0.59 |

Note:
In the fed-batch fermentation, only a portion of the 95DE sugar is added up front, while the rest is fed later. So, while the initial isomaltose is lower in the fed-batch, total amount added across the fermentation is the same as in the straight batch. The final volumes in both cases are similar.

TABLE 7-2

Maltose consumption in straight batch and fed-batch fermentations

| | | Straight batch | | Fed Batch (average of duplicates) | |
|---|---|---|---|---|---|
| Strain | Description | Maltose initial (g/L) | Maltose final (g/L) | Maltose initial (g/L) | Maltose final (g/L) |
| Strain F | Parent | 1.92 | 1.95 | N/A | N/A |
| 2-4 | Transporter ScMAL11+, Isomaltase ScIMA1+, Maltase ScMAL12+ | 1.95 | 0.59 | 0.92 (See note below) | 0.53 |

Note:
In the fed-batch fermentation, only a portion of the 95DE sugar is added up front, while the rest is fed later. So, while the initial maltose is lower in the fed-batch, total amount added across the fermentation is the same as in the straight batch. The final volumes in both cases are similar.

Example 8: Shake Flask Characterization Identifies Preferred Transporters for Improving Isomaltose Consumption Strains Strain E, 1-8, 1-4, 3-1, 3-2, 3-3 & 3-4 are streaked out for single colonies on a YPD plate and incubated at 30° C. until single colonies are visible (1-2 days). Cells from plates are scraped into sterile growth medium and the optical density ($OD_{600}$) is measured. Optical density is measured at wavelength of 600 nm with a 1 cm path length using a model Genesys20 spectrophotometer (Thermo Scientific).

A shake flask is inoculated with the cell slurry to reach an initial $OD_{600}$ of 0.1-0.3. Prior to inoculation, the 250 mL non-baffled shake flasks containing 0.18 g/L dry $CaCO_3$ are sterilized. Immediately prior to inoculating, 20 mL of shake flask medium is added to the dry calcium carbonate. The shake flask medium is sterilized, pH to 4.0, and contains 1.95 mL/L of 40% urea, 0.13 g/L magnesium sulfate heptahydrate, 0.91 mL/L of an APK solution [4.15% (w/v) nitrogen (in the form of ammonium) and 9.35% (w/v) phosphorous (in the form of phosphate), and 8.44% (w/v) potassium], 1 mL/L of the trace element solution described in table 8-1 and 1 mL/L of a vitamin solution (0.05 g/L biotin), 100.0 g/L glucose, 0.3 g/L glycerol, 4.0 g/L 2-(N-Morpholino) ethanesulfonic acid (IVIES).

The inoculated flask is incubated at 34° C. with shaking in an orbital shaker at 150 rpm for 72 hours. Samples are taken and analyzed for lactic acid and glucose concentrations in the broth during fermentation by high performance liquid chromatography with refractive index detector. Maltose and isomaltose are determined by high performance liquid chromatography with evaporative light scattering detector. Isomaltose concentrations during the fermentations are shown in FIG. 1.

TABLE 8-1

Trace composition

| Chemicals | Formula | MW | gram/L | Product code |
|---|---|---|---|---|
| EDTA (Titriplex III ®) | $C_{10}H_{14}N_2Na_2O_8 \cdot 2H_2O$ | 372.24 | 15.00 | Sigma I-5134 |
| Zinc sulphate heptahydrate | $ZnSO_4 \cdot 7H_2O$ | 287.54 | 4.50 | Fisher Z68-500 |
| Manganese chloride dihydrate | $MnCl_2 \cdot 2H_2O$ | 161.88 | 1.0 | Sigma M-8530 |
| Copper(II)sulphate pentahydrate | $CuSO_4 \cdot 5H_2O$ | 249.68 | 0.30 | Sigma C-3036 |
| Iron sulphate heptahydrate | $FeSO_4 \cdot 7H_2O$ | 278.02 | 3.00 | Fisher I146-500 |

TABLE 8-2

Oligosaccharide depletion at the time of glucose depletion

| Strain | Glucose initial (g/L) | Glucose final (g/L) | Isomaltose initial (g/L) | Isomaltose final (g/L) | Maltose initial (g/L) | Maltose final (g/L) | Description |
|---|---|---|---|---|---|---|---|
| Strain E | 107.1 | <.040 | 1.24 | 1.40 | 0.97 | 0.90 | Parent |
| 1-8 | 107.1 | <.040 | 1.24 | 1.40 | 0.97 | 0.90 | Isomaltase ScIMA1+, |
| 3-3 | 103.3 | <.040 | 1.3 | 1.16 | 1.05 | 0.64 | Isomaltase ScIMA1+, Transporter DhMAL11 |
| 3-4 | 103.3 | <.040 | 1.3 | 0.91 | 1.05 | 0.51 | Isomaltase ScIMA1+, Transporter TdMAL11 |
| 3-1 | 107.1 | <.040 | 1.24 | 0.95 | 0.97 | 0.64 | Isomaltase ScIMA1+, Transporter ScMAL11 |
| 3-2 | 107.1 | <.040 | 1.24 | 0.81 | 0.97 | 0.52 | Isomaltase ScIMA1+, Transporter (SEQ ID NO: 18) |

Oligomeric sugar concentrations from shake flask experiments performed with strains containing differing maltose/isomaltose transporters. Initial sugar concentrations are measured at the time of inoculation. Final sugar concentrations are measured at the time of glucose depletion.

Strain 3-2 containing the maltose/isomaltose transporter, of SEQ ID NO: 18, shows the fastest depletion of isomaltose

Example 9 Generation of a Lactic Acid Producing Yeast Capable of Intracellular Isomaltose Consumption Strain G Strain E is subjected to four separate rounds of mutagenesis, each round followed by selection on Base Tolerant (BT) plates. Base tolerance plate media is made by adding 10 mL of 5 M KOH to 1 liter of PDA (Potato Dextrose Agar). Isolates from the BT plates are then patched onto three separate PDA plates containing 75, 80 and 85 g/L lactic acid respectively, for further selection. The best performing single colony isolates from the lactic acid containing PDA plates are identified through screening in shake flasks using the shake flask method of Example 4 with the following change: the sugar in the shake flask medium is the quantity of 95DE sugar required to result in a glucose concentration of 160 g/L. The best performing single colony isolates are pooled together and moved forward to the next round of mutagenesis. Improved isolates are subjected to one final round of mutagenesis followed by selection on PDA plates containing 85 & 90 g/L lactic acid and screened as above. A single colony isolate from this process which is shown to be improved in lactic acid production is designated 14548.

Sisu14548 is then subjected to a selection for stability by serial cultivation in aerobic shake flasks containing YPD media for ~50 generations. When this strain is plated for single colonies, a white/yellow phenotype is observed. Five of each of the colored colonies are run in shake flasks. The rate of the yellow colonies are superior to the white colonies. One of the best performing yellow colonies is entered into the culture collection as Strain G.

Strain 9-1

Strain G is transformed with SEQ ID NO: 8. SEQ ID NO: 8 contains: i) an expression cassette for the selectable marker gene melibiase from S. cerevisiae (ScMEL5) flanked by LoxP sites; ii) an expression cassette for an isomaltase gene from S. cerevisiae (ScIMA1), encoding the amino acid sequence SEQ ID NO: 9; and iii) flanking DNA for targeted chromosomal integration into integration locus B. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YNB plates containing 2% lactic acid containing 32 µg/ml x-alpha-gal. A single blue colony is selected. Correct integration of SEQ ID NO: 8 into the selected blue colony is verified by PCR. A PCR verified isolate is designated Strain 9-1.

Strain 9-2

Strain 9-1 is transformed with SEQ ID NO: 10 (pVL16). SEQ ID NO: 10 contains: i) an expression cassette for the selectable marker gene CYB2A from I. orientalis (IoCYB2A) flanked by LoxP sites; ii) an expression cassette for an isomaltase gene from S. cerevisiae (ScIMA1), encoding the amino acid sequence SEQ ID NO: 9; and iii) flanking DNA for targeted chromosomal integration into integration locus B. Transformants are selected on YNB plates containing 2% lactic acid as sole carbon source. Resulting transformants are streaked for single colony isolation on YNB plates containing 2% lactic acid as sole carbon source. A single colony is selected. Correct integration of SEQ ID NO: 10 into the selected colony is verified by PCR. A PCR verified isolate is designated Strain 9-2.

Strain 9-3

Strain 9-2 is transformed with the plasmid of SEQ ID NO: 11. SEQ ID NO: 11 contains: i) an expression cassette for the selectable marker gene invertase from S. cerevisiae (ScSUC2); and ii) an expression cassette for CRE recombinase gene to recycle the selectable markers ScMEL5 & IoCYB2A. Transformants are selected on YNB plates containing 2% sucrose as sole carbon source and 32 µg/ml x-alpha-gal which provides colorimetric indication of the absence of the ScMEL5 marker gene. Resulting transformants are streaked for single colony isolation on YPD containing 32 µg/ml x-alpha-gal. A single white colony is selected. Loss of ScMEL5 and IoCYB2A from the selected white colony is verified by PCR. A PCR verified isolate is designated Strain 9-3.

Strain 9-4

Strain 9-3 is transformed with SEQ ID NO: 17. SEQ ID NO: 17 contains: i) a maltose/isomaltose transporter gene, encoding the amino acid sequence SEQ ID NO: 18; and ii) flanking DNA for targeted chromosomal integration into integration locus A. Transformants are selected on YNB plates containing 2% isomaltose as sole carbon source. Resulting transformants are streaked for single colony isolation on YNB plates containing 2% isomaltose as sole carbon source. A single colony is selected. Correct integration of SEQ ID NO: 17 into the selected colony is verified by PCR. A PCR verified isolate is designated Strain 9-4.

Strain 9-5

Strain 9-4 is transformed with SEQ ID NO: 23 & 24. SEQ ID NO: 23 contains: i) an expression cassette for the selectable marker gene melibiase from S. cerevisiae (ScMEL5) flanked by LoxP sites; and ii) the first 174 bp of a maltose/isomaltose transporter gene, encoding the amino acid sequence SEQ ID NO: 18; and iii) flanking DNA for targeted chromosomal integration into integration to the upstream portion of locus A. SEQ ID NO: 24 contains: i) the last 1831 bp of a maltose/isomaltose transporter gene, encoding the amino acid sequence SEQ ID NO: 18; and ii) flanking DNA for targeted chromosomal integration into the downstream portion of locus A. SEQ ID NO: 23 & 24 contain 153 bp of homology allowing for integration via homologous recombination. Transformants are selected on YNB plates containing 2% melibiose as sole carbon source and 32 µg/ml x-alpha-gal which provides colorimetric indication of the presence of the ScMEL5 marker gene. Resulting transformants are streaked for single colony isolation on YNB plates containing 2% isomaltose as sole carbon source and 32 µg/ml x-alpha-gal for single colonies. A single blue colony is selected. Correct integration of SEQ ID NO: 23 & 24 into the selected colony is verified by PCR. A PCR verified isolate is designated Strain 9-5.

Strain 9-6

Strain 9-5 is transformed with the plasmid of SEQ ID NO: 11. SEQ ID NO: 11 contains: 1) an expression cassette for the selectable marker gene invertase from *S. cerevisiae* (ScSUC2); and ii) an expression cassette for CRE recombinase gene to recycle the selectable marker ScMEL5. Transformants are selected on YNB plates containing 2% sucrose as sole carbon source and 32 µg/ml x-alpha-gal which provides colorimetric indication of the absence of the ScMEL5 marker gene. Resulting transformants are streaked for single colony isolation on YPD containing 32 µg/ml x-alpha-gal. A single white colony is selected. Loss of ScMEL5 from the selected white colony is verified by PCR. A PCR verified isolate is designated Strain 9-6.

Strain 9-7

Strain 9-4 is transformed with SEQ ID NO: 23 & 24. SEQ ID NO: 23 contains: i) an expression cassette for the selectable marker gene melibiase from *S. cerevisiae* (ScMEL5) flanked by LoxP sites; and ii) the first 174 bp of a maltose/isomaltose transporter gene, encoding the amino acid sequence SEQ ID NO: 18; and iii) flanking DNA for targeted chromosomal integration into integration to the upstream portion of locus A. SEQ ID NO: 24 contains: i) the last 1831 bp of a maltose/isomaltose transporter gene, encoding the amino acid sequence SEQ ID NO: 18; and ii) flanking DNA for targeted chromosomal integration into the downstream portion of locus A. SEQ ID NO: 23 & 24 contain 153 bp of homology allowing for integration via homologous recombination. Transformants are selected on YNB plates containing 2% melibiose as sole carbon source and 32 µg/ml x-alpha-gal which provides colorimetric indication of the presence of the ScMEL5 marker gene. Resulting blue colony transformants are then patched onto YNB plates containing 2% isomaltose and screened for improved growth on isomaltose. Improved isolates are streaked for single colony isolation on YNB plates containing 2% isomaltose as sole carbon source and 32 µg/ml x-alpha-gal for single colonies. A single blue colony is selected. Correct integration of SEQ ID NO: 23 & 24 into the selected colony is verified by PCR. A PCR verified isolate is designated Strain 9-7.

TABLE 9-1

Lactic acid producing yeast

| Strain | Description | Parent |
|---|---|---|
| Strain A | Wild Type | N/A |
| Strain B | Chemostat evolved wild type | Strain A |
| Strain C | IoPDCΔ, LhLDH+ | Strain B |
| Strain D | Mutagenesis and selection for lactic acid resistance, cyb2AΔ, cyb2BΔ, IoGPDΔ | Strain C |
| Strain E | Mutagenesis and selection for lactic acid resistance | Strain D |
| Strain G | Mutagenesis and selection for lactic acid resistance | Strain E |
| 9-1 | ScIMA1+(single copy), ScMEL5+ | Strain G |
| 9-2 | ScIMA1+, ScMEL5+, IoCYB2A+ | 9-1 |
| 9-3 | ScIMA1+ | 9-2 |
| 9-4 | ScIMA1+, gene encoding for SEQ ID NO: 18 (single copy) | 9-3 |
| 9-5 | ScIMA1+, gene encoding for SEQ ID NO: 18, ScMEL5+ | 9-4 |
| 9-6 | ScIMA1+, gene encoding for SEQ ID NO: 18 | 9-5 |
| 9-7 | ScIMA1+, gene encoding for SEQ ID NO: 18, ScMEL5+ | 9-4 |

Example 10: Operating a Fermentation in a Fed-Batch Mode Improves Isomaltose Consumption as Compared to Straight Batch Fermentation with a Yeast that is Engineered to be Capable of Consuming Starch Based Dimers of Glucose and Produce an Organic Acid Example 10-1: Straight Batch Fermentations with Lactic Acid Producing Strain 9-6

The lactic acid producing yeast strain 9-6 is run in fermenters to assess maltose and isomaltose consumption as well as lactic acid production.

The transglucosidase used is based on the TG-L2000 product available from DuPont Biosciences, with the following differences: 1) the final glycerol composition is less than 1%; 2) traces of NaCl are present in the product but <0.1%; 3) the following additional preservatives and stabilizers are added—Glucose (20-30% w/w) and sodium benzoate (0.2-0.4% w/w).

The fermentation broth consists of water as well as sufficient nutrients required to enable cell growth. The fermentation broth also contains an anti-foam agent to control foaming in the fermentation.

A fermentor is partially filled to its of volumetric operating capacity with the components of the fermentation broth as well all of the desired glucose. The glucose source 95DE sugar. The temperature is controlled at 34° C. The fermentor is then inoculated with the yeast 9-6 that is engineered to be capable of consuming starch based dimers of glucose and produce lactic acid. The pH is maintained at pH 4.4 by the addition of calcium hydroxide until the lactic acid concentration reaches 35% of the final target lactic acid concentration. After this time, no further calcium hydroxide is added to the fermentation.

As the fermentation proceeds, the glucose, maltose and isomaltose are converted into lactic acid. The glucose concentration is monitored by a near infrared spectroscopy system (NIR) (Brueker—Matrix F model). When the glucose has been reduced to less than 20 g/L as measured by NW (approximately 30 hours after inoculation), the transglucosidase enzyme is added to the fermentation at a dose of 0.017% (volume enzyme solution/volume fermentation broth). The fermentation is then allowed to proceed until the glucose is reduced below 0.5 g/L.

Figure 2:
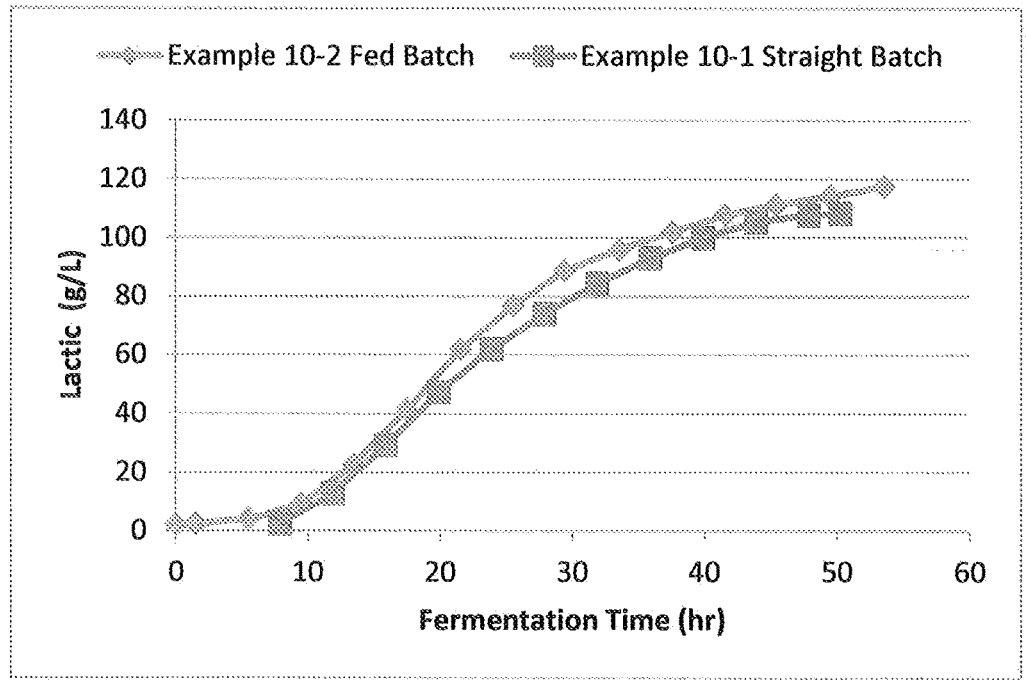
FIG. 2 is a graph showing lactic acid production during the fermentations of Example 10.

The residual oligosaccharide concentrations resulting from the straight batch fermentation are shown in tables 10-1. The lactic acid concentrations during the fermentation are shown in FIG. 2.

Example 10-2: Fed Batch Fermentations with Lactic Acid Producing Strain 9-6

The transglucosidase used is the same transglucosidase preparation of Example 10-1.

The fermentation broth consists of water as well as sufficient nutrients required to enable cell growth. The fermentation broth also contains an anti-foam agent to control foaming in the fermentation.

A fermentor is partially filled to 72% of volumetric operating capacity with the components of the fermentation broth as well as 70% of the total glucose to be added. The glucose source is 95DE sugar. The temperature is controlled at 34° C. The fermentor is then inoculated with the yeast 9-6. The pH is maintained at pH 4.4 by the addition of calcium hydroxide until the lactic acid concentration reaches 35% of the final target lactic acid concentration. After this time, no further calcium hydroxide is added to the fermentation.

As the fermentation proceeds, the glucose, maltose and isomaltose are converted into lactic acid. The glucose concentration is monitored by a near infrared spectroscopy system (NIR) (Brueker—Matrix F model). When the glucose has been reduced to less than 20 g/L as measured by NIR (approximately 20 hours after inoculation), the transglucosidase enzyme is added to the fermentation at a dose of 0.017% (volume enzyme solution/volume fermentation broth).

The fermentation is then allowed to further proceed until the glucose concentration reaches 10 g/L. The remaining 30% of the total glucose is then gradually added to the fermentor at a rate controlled to maintain the glucose between 8 g/L and 12 g/L as measured by the NIR.

Once 100% of the target dextrose has been added, the glucose feed is stopped and the fermentation proceeds until the glucose is reduced below 0.5 g/L.

titer, and fermentation yield of fermentation product from glucose) in fed-batch fermentations as with batch fermentation, with the additional benefit of more effectively reducing the dimer, trimer (and while not shown tretamer) oligomers of glucose when utilizing a fed-batch fermentation.

Example 11: Operating a Fermentation with Yeast 9-6 that is Engineered to be Capable of Consuming Starch Based Dimers of Glucose and Produce Lactic Acid Allows a Fermentation to be Operated Will a Lower Dose of Transglucosidase Enzyme while Still Achieving a Similar Final Isomaltose Concentration Comparative Example 11-1: Fed Batch Fermentations with Lactic Acid Producing Strain G, that has not been Engineered for the Consumption of Isomaltose and Maltose with Transglucosidase Added to 0.035%

A fermentation is operated as in example 10-2, with the following changes. When the fermenter is inoculated, it is inoculated with the yeast strain G. Also, when the transglucosidase enzyme is added to the fermentation, it is added at a dose of 0.035% (volume enzyme solution/volume fermentation broth). This fermentation is repeated several times. The mean results from the fermentation are shown in Table 11-1.

Comparative Example 11-2: Fed Batch Fermentations with Lactic Acid Producing Yeast Strain G, that has not been Engineered for the Consumption of Isomaltose and Maltose with Transglucosidase Added to 0.025%

A fermentation is operated as in example 10-2, with the following changes. When the fermenter is inoculated, it is inoculated with the yeast strain G. Also, when the transglucosidase enzyme is added to the fermentation, it is added at a dose of 0.025% (volume enzyme solution/volume fermentation broth). This fermentation is repeated several times. The mean results from the fermentation are shown in Table 11-1.

TABLE 10-1

Final metabolite concentrations in batch and fed batch fermentations of examples 10-1 and 10-2. Concentrations are in (g/L)

| | | | Enzyme | | Final Concentrations (g/L) | | | | |
| --- | --- | --- | --- | --- | --- | --- | --- | --- | --- |
| | Strain | Enzyme | Dose (v/v) | Lactic acid | Glucose | Isomaltose | Maltose | Maltotriose | Panose |
| Straight batch 10-1 | 9-6 | TG | 0.017% | 119.6 | 0.31 | 0.76 | 0.00 | 0.00 | 0.27 |
| Fed batch 10-2 | 9-6 | TG | 0.017% | 113.1 | 0.18 | 0.45 | 0.00 | 0.01 | 0.02 |

Table 10-1 shows that for fermentations performed using the yeast 9-6 that is engineered to be capable of consuming starch based dimers of glucose and produce lactic acid, the fed-batch fermentation results in a lower final concentration of isomaltose compared with the straight batch fermentation. Additionally, as can be shown in FIG. 2, the lactic acid production from the batch and fed batch fermentations are similar using the yeast of the invention. Therefore, with the invention, similar fermentation performance in the manufacture of fermentation products (as described earlier) can be achieved (e.g. fermentation product production rate, product Example 11-3: Fed Batch Fermentations with Lactic Acid Producing Strain 9-6 that has been Engineered for the Consumption of Isomaltose and Maltose with Transglucosidase Added to 0.021%

A fermentation is operated as in example 10-2, with the following change. When the transglucosidase enzyme is added to the fermentation, it is added at a dose of 0.021% (volume enzyme solution/volume fermentation broth). This fermentation is repeated several times. The mean results from the fermentation are shown in Table 11-1.

TABLE 11-1

Final metabolite concentrations from batch fermentations operated according to comparative examples 11-1, 11-2 and example 11-3. Concentrations are in (g/L).

| Example | Strain | Enzyme Dose (v/v) | Lactic acid | Glucose | Isomaltose | Maltose | Maltotrios | Panose |
|---|---|---|---|---|---|---|---|---|
| 11-2 | Strain G | 0.025% | 121.0 | 0.48 | 0.67 | 0.09 | 0.00 | 0.00 |
| 11-1 | Strain G | 0.035% | 119.9 | 0.27 | 0.35 | 0.02 | 0.00 | 0.00 |
| 11-3 | 9-6 | 0.021% | 117.1 | 0.21 | 0.33 | 0.00 | 0.00 | 0.01 |

FIG. 11-1 demonstrates that when operating a fermentation with the yeast strain G that has NOT been engineered for maltose and isomaltose consumption, a reduction in the dose of transglucosidase results in an increase in the final isomaltose concentration. Further, according to example 11-3, when a similar fermentation is operated with the yeast 9-6 and a reduced dose of transglucosidase, the final isomaltose concentration is similar to the fermentation operated with strain G and the original dose of transglucosidase. Therefore, using the inventive genetically engineered microorganism of the invention, equivalent reduction in oligomers of glucose can be achieved with less external enzyme being added; or greater reduction in oligomers of glucose can be achieved using similar amounts of external enzyme added.

Example 12: Operating a Fermentation with Yeast Strain 9-6 that is Engineered to be Capable of Consuming Starch Based Dimers of Glucose and Produce an Organic Acid Allows a Fermentation to be Operated with a Less Expensive Enzyme (DuPont Distillase SSF (Comprising Primarily a Glucoamylase)) at a Lower Dose while Still Achieving a Similar (or Better) Final Isomaltose Concentration as Obtained Using a Transglucosidase Added Externally with a Yeast that has not been Modified in Accordance with the Invention The glucoamylase (GA) enzyme used is the DuPont Distillase SSF product available from DuPont Biosciences.

Example 12-1: Fed Batch Fermentations with Lactic Acid Producing Strain 9-6 of the Invention with Glucoamylase Added to 0.017%

A fermentation is operated as in example 10-2, with the following change. When the enzyme is added to the fermentation, the glucoamylase is added instead of the transglucosidase, and it is added at a dose of 0.017% (volume enzyme solution/volume fermentation broth). This fermentation is repeated eight times. The mean fermentation results are shown in Table 12-1

TABLE 12-1

Final lactic acid and sugar concentrations for batch fermentations of Comparative Example 11-2 and Example 12-1. Concentrations are in (g/L).

| Example | Strain | Enzyme | Dose (v/v) | Lactic acid | Glucose | Isomaltose | Maltose | Maltotrios | Panose |
|---|---|---|---|---|---|---|---|---|---|
| Comparative 11-2 | Strain G | TG | 0.025% | 121.0 | 0.48 | 0.67 | 0.09 | 0.00 | 0.00 |
| 12-1 | 9-6 | GA | 0.017% | 116.9 | 0.28 | 0.51 | 0.03 | 0.05 | 0.03 |

The mean residual isomaltose concentration for the batches of Example 12-1 were lower than for the batches of Comparative Example 11-2. This lower residual isomaltose concentration was achieved even using the less expensive GA enzyme of Example 12-1 as well as using the GA enzyme at a lower dose compared with the TG does of Comparative Example 11-2.

Example 13: Addition of a Transglucosidase to a Fermentation with Yeast 9-6 of the Invention Results in Lower Residual Concentrations of Longer Chain Oligomers of Glucose (DP3 and Longer)

Example 13-1: Fed Batch Fermentations with Lactic Acid Producing Strain 9-6 with No External Enzyme Additions to the Fermentation The lactic acid producing yeast strain 9-6 is run in fermenters to assess residual final concentrations of longer chain (DP3+) oligomers of glucose.

Fermentors with a working volume of 1.5 L are filled with 569.9 g of a 34% (w/v) solution of 95DE sugar, 0.2 mL of concentrated (95% w/v) sulfuric acid, 926.4 g deionized water, 1.5 mL of a 1:100 aqueous dilution of antifoam (Emerald Performance Materials BCC-627) and 0.19 g of MgSO4 then heat sterilized. After sterilization, the fermenters are cooled to 34° C. The following sterile components are then added: 3.1 g of an aqueous solution of 40% (w/v) urea, 1.5 g of an aqueous APK solution [4.15% (w/v) nitrogen (in the form of ammonium), and 9.35% (w/v) phosphorous (in the form of phosphate), and 8.44% (w/v) potassium], 1.5 mL of a 0.1 g/L D-biotin solution, and 1.5 mL of a trace minerals package (containing 4.5 g/L ZnSO4, 3 g/L FeSO4, 1 g/L, and 0.3 g/L CuSO4).

The glycerol stock containing cryovials for strain 9-6 are warmed by incubation at room temperature until just thawed. The fermentation is started by inoculation with the thawed glycerol stocks for each of the strains. The pH in the fermentors is maintained at 4.4 by controlled addition of a 30% (w/w) suspension of lime (calcium hydroxide) until approximately 77 g of the lime suspension has been added.

The fermentors are sparged with 0.25 SLPM (standard liters per minute) air through a sparge ring at the base of the fermentor vessel. An oxygen uptake rate of 12-13 mmol O2/(L*h) is achieved by selecting an appropriate agitation speed. These fermentations are operated such that after the cells achieve a sufficient density, oxygen limitation is achieved and subsequently maintained throughout the rest of the fermentation (e.g. dissolved oxygen at less than 5% of atmospheric air saturation.)

Dissolved oxygen is measured using Mettler Toledo INPRO 6800 sensor (Mettler-Toledo GmbH, Urdorf, Switzerland), calibrated prior to inoculation. 0% is calibrated by sparging 100% nitrogen into the vessel and 100% is calibrated using air sparging according to the run condition as in the vessel as detailed above (prior to inoculation).

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific). Unless explicitly noted otherwise, an experimentally derived conversion factor of 1.33 OD600 units per 1 g dry cell mass is used to estimate cell dry weight.

Oxygen uptake rate ("OUR") is calculated using methods known to those in the art. For this example, oxygen, nitrogen and carbon dioxide values are measured by an off gas analyzer (oxygen measured using paramagnetic alternating pressure method and CO2 using infrared components).

Samples are taken immediately after inoculation, at the end of the batch, and periodically throughout the fermentation. Samples are analyzed for biomass growth via optical density, lactic acid and glucose concentration by high performance liquid chromatography with refractive index detector or YSI analysis, and for maltose and isomaltose by high performance liquid chromatography with evaporative light scattering detection (ELSD).

78.8 g of a 61% (w/v) 95DE sugar is prepared in a feed bottle. When YSI analysis indicates the fermentation glucose concentration has reached 10 g/L, glucose feed is started. The glucose feed is performed at a constant rate such that it takes approximately 12 hours for the entire feed volume to be added to the fermentor. The fermentation results are shown in Table 13-1.

Example 13-2: Fed Batch Fermentations with Lactic Acid Producing Strain 9-6 with Transglucosidase Added to 0.025%

The transglucosidase used is the same transglucosidase preparation of Example 10-1.

A fermentation is carried out according to the method of example 13-1 with the difference that a dose of transglucosidase is added to the fermentation at the time that the feed of additional glucose is commenced. The transglucosidase is added at a dose of 0.025% (volume enzyme solution/volume fermentation broth).

Example 13-3: Fed Batch Fermentations with Lactic Acid Producing Strain 9-6, with Distillase (a Glucoamylase) Added to 0.025%

The glucoamylase (GA) enzyme used is the DuPont Distillase SSF product available from DuPont Biosciences.

A fermentation is carried out according to the method of example 13-1 with the difference that a dose of glucoamylyase is added to the fermentation at the time that the feed of additional glucose is commenced. The glucoamylase is added to a concentration of 0.025% (volume enzyme solution/volume fermentation broth).

TABLE 13-1

Final lactic acid and sugar concentrations from Examples 13-1, 13-2, and 13-3. Concentrations are in (g/L).

| | | | Enzyme | Concentrations (g/L) | | | | | | | |
|---|---|---|---|---|---|---|---|---|---|---|---|
| | | | Dose | Lactic | Glucose | Isomaltose | | Maltose | | Panose | |
| Strain | Example | Enzyme | (v/v) | Final | Final | Initial | Final | Initial | Final | Initial | Final |
| 9-6 | 13-3 | TG | 0.025% | 131.2 | 0.8 | 1.7 | 1.1 | 2.2 | 0.0 | 1.1 | 0.1 |
| 9-6 | 13-2 | GA | 0.025% | 129.9 | 1.3 | 1.6 | 1.2 | 2.3 | 0.4 | 1.1 | 0.4 |
| 9-6 | 13-1 | None | NA | 124.8 | 1.8 | 1.7 | 1.3 | 2.4 | 1.1 | 1.1 | 1.2 |

Table 13-1 shows that when a fermentation is performed with a yeast such as 9-6 engineered for the consumption of lactic acid and no enzymes are added, as in Example 13-1, The panose concentration is not significantly reduced. By contrast, when either the GA or TG enzyme is added, as in Examples 13-2 and 13-3, the panose concentration is significantly reduced. And, while the fermentation utilizing the TG enzyme performed slightly better than the fermentation utilizing the GA enzyme, the GA enzyme is significantly simpler enzyme system than the TG enzyme and more readily available at lower costs per quantity. Therefore, using the GA enzyme at similar concentration as the TG enzyme would result in a more cost effective fermentation for similar fermentation results achieved.

Example 14. The Isomaltose/Maltose Transporter from *Saccharomyces mikatae*

Strain 14-1 is similar to strain 9-6 with only a single copy of the gene encoding for SEQ ID NO: 18 (a maltose/isomaltose transporter gene).

Strain 14-2 is similar to strain 14-1 with the following difference. In place of the gene encoding SEQ ID NO: 18, strain 14-2 has a single copy of the SmMAL11 maltose/isomaltose transporter gene from *S. mikatae*, which encodes for the polypeptide of SEQ ID NO: 25.

A shake flask fermentation is performed according Example 4 with the following change. The sugar used to prepare the shake flask medium is the quantity of 95DE sugar required to result in 160 g/l, glucose. The results are shown in Table 14-1

TABLE 14-1

Initial and final lactic acid and sugar concentrations from the shake flask fermentations of Example 14. Concentrations are in (g/L). 0 hour samples represent initial concentrations and 93 h samples represent final concentrations.

| Strain | time after inoculation (h) | Glucose | Lactic Acid | Maltose | Isomaltose | Panose |
|---|---|---|---|---|---|---|
| Strain G | 0 | 160.3 | 0.0 | 1.1 | 2.1 | 0.91 |
|  | 93 | 3.3 | 122.6 | 0.0 | 2.1 | 0.74 |
| 14-1 | 0 | 160.3 | 0.0 | 1.1 | 2.1 | 0.91 |
|  | 93 | 6.9 | 120.5 | 0.0 | 1.3 | 0.69 |
| 14-2 | 0 | 160.3 | 0.0 | 1.1 | 2.1 | 0.91 |
|  | 93 | 10.0 | 118.5 | 0.0 | 0.3 | 0.40 |

Table 14-1 shows that in shake flask fermentations, strain 14-2, containing the gene encoding the maltose/isomaltose transporter gene from *S. mikatae* consumes more isomaltose compared with the comparable strain 14-1 containing the gene encoding the maltose/isomaltose transporter of SEQ ID NO: 18.

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A fermentation process for fermenting a starch hydrolysate containing 60-98 weight percent of glucose based on total carbohydrate and 0.3-5% weight percent of isomaltose based on total carbohydrate to a non-ethanol fermentation product, the method comprising:
 a) forming a fermentation broth containing the starch hydrolysate and a genetically modified yeast containing
  i) an exogenous gene encoding a transporter capable of transporting isomaltose, wherein the transporter is a polypeptide with an amino acid sequence having greater than 90% sequence identity to the amino acid sequence of SEQ ID NO: 7, SEQ ID NO: 20, SEQ ID NO: 22, or SEQ ID NO: 25; and
  ii) an exogenous gene encoding an enzyme isomaltase capable of converting isomaltose to glucose, wherein the gene encodes for a polypeptide having greater than 90% sequence identity to the amino acid sequence of SEQ ID NO: 9;
 b) fermenting the starch hydrolysate in the fermentation broth to produce a non-ethanol fermentation product, wherein the non-ethanol fermentation product is an organic acid; and
 c) isolating the organic acid from the fermentation broth.

2. A batch fermentation process for fermenting a starch hydrolysate containing 60-98 weight percent of glucose based on total carbohydrate and 0.3-5% weight percent of isomaltose based on total carbohydrate to a non-ethanol fermentation product, the method comprising:
 a) forming a fermentation broth containing a first portion of a total amount of the starch hydrolysate to be fermented and a genetically modified yeast containing
  i) an exogenous gene encoding a transporter capable of transporting isomaltose, wherein the transporter is a polypeptide with an amino acid sequence having greater than 90% sequence identity to the amino acid sequence of SEQ ID NO: 7, SEQ ID NO: 20, SEQ ID NO: 22, or SEQ ID NO: 25; and
  ii) an exogenous gene encoding an enzyme isomaltase capable of converting isomaltose to glucose, wherein the gene encodes for a polypeptide having greater than 90% sequence identity to the amino acid sequence of SEQ ID NO: 9;
 b) fermenting the first portion of the starch hydrolysate in the fermentation broth in an initial fermentation step to produce a fermentation product;
 c) feeding the remaining portion of the total amount of the starch hydrolysate to be fermented containing 60-98 weight percent of glucose based on total carbohydrate and 0.3-5% weight percent of isomaltose based on total carbohydrate into the fermentation broth, wherein the fermentation broth on average has a glucose concentration of 50 g/l or less during this step (c);
 d) producing a final fermentation broth containing the fermentation product, wherein the fermentation product is an organic acid; and
 e) isolating the organic acid from the fermentation broth.

3. The fermentation process of claim 2, wherein the fermentation broth during step (c) on average has a glucose concentration of from about 5 to about 15 g/L.

4. The fermentation process of claim 1, wherein the genetically modified yeast contains an exogenous gene encoding an enzyme that catalyzes the formation of a product other than ethanol.

5. The fermentation process of claim 1, wherein the genetically modified yeast is a crabtree negative yeast.

6. The fermentation process of claim 5, wherein the genetically modified yeast is a yeast of the genus *Kluyveromyces* or *Issatchenkia*.

7. The fermentation process of claim 5, wherein the genetically modified yeast is a yeast of the *I. orientalis/P. fermentans* clade.

8. The fermentation process of claim 1, wherein the genetically modified yeast contains a heterologous gene encoding transporter capable of transporting isomaltose and a heterologous gene encoding an enzyme capable of converting isomaltose to glucose.

9. The fermentation process of claim 1, wherein the genetically modified yeast comprises a PDC deletion.

10. The fermentation process of claim 1, wherein the enzyme generated by the genetically modified yeast for converting isomaltose to glucose is also active for the conversion of maltose into glucose.

11. The fermentation process of claim 1, wherein the fermentation broth has a pH of less than 4.8 during the active fermentation process.

12. The fermentation process of claim 1, wherein the fermentation broth has a pH of less than 3.5 during the active fermentation process.

13. The fermentation process of claim 2, wherein during the feeding step, the remaining portion of the total amount of starch hydrolysate in step c) is fed into the fermentation broth using a variable rate addition system.

14. The fermentation process of claim 2, further comprising the addition of at least one active enzyme that converts isomaltose into glucose during step c).

15. The fermentation process of claim 1, further comprising the addition of at least one active enzyme that converts isomaltose into glucose.

16. The fermentation process of claim 1 and, further comprising the addition of at least one active enzyme that is capable of converting DP3 and DP4 oligomers of glucose containing 1,4 ether linkages to glucose.

17. The fermentation process of claim 16, wherein the at least one active enzyme comprises glucoamylase.

18. The fermentation process of claim 1, wherein one active copy of the exogenous gene encoding a transporter capable of transporting isomaltose is present in the genome of the genetically engineered yeast.

* * * * *